(12) United States Patent
Zhang et al.

(10) Patent No.: US 9,133,177 B2
(45) Date of Patent: Sep. 15, 2015

(54) AMBIPOLAR SMALL MOLECULE HOSTS FOR PHOSPHORESCENT GUEST EMITTERS

(75) Inventors: Yadong Zhang, Alpharetta, GA (US);
Carlos Zuniga, Atlanta, GA (US);
Gaelle Deshayes, Atlanta, GA (US);
Julie Leroy, Brussels (BE); Stephen Barlow, Atlanta, GA (US); Seth R. Marder, Atlanta, GA (US); Xuyang He, Atlanta, GA (US); Sung-Jin Kim, Atlanta, GA (US); Bernard Kippelen, Decatur, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 713 days.

(21) Appl. No.: 13/379,595

(22) PCT Filed: Jun. 21, 2010

(86) PCT No.: PCT/EP2010/058732
§ 371 (c)(1),
(2), (4) Date: Mar. 19, 2012

(87) PCT Pub. No.: WO2010/149622
PCT Pub. Date: Dec. 29, 2010

(65) Prior Publication Data
US 2012/0168732 A1 Jul. 5, 2012

Related U.S. Application Data

(60) Provisional application No. 61/220,116, filed on Jun. 24, 2009.

(51) Int. Cl.
| | | |
|---|---|---|
| H01L 51/54 | (2006.01) | |
| C07D 271/107 | (2006.01) | |
| C07D 413/10 | (2006.01) | |
| C07D 413/14 | (2006.01) | |
| C08F 12/14 | (2006.01) | |
| C08F 120/36 | (2006.01) | |
| C08F 220/36 | (2006.01) | |
| C08F 232/08 | (2006.01) | |
| C08G 61/08 | (2006.01) | |
| H01L 51/00 | (2006.01) | |
| H05B 33/20 | (2006.01) | |
| H01L 51/50 | (2006.01) | |

(52) U.S. Cl.
CPC ............ *C07D 413/10* (2013.01); *C07D 413/14* (2013.01); *C08F 12/14* (2013.01); *C08F 120/36* (2013.01); *C08F 220/36* (2013.01); *C08F 232/08* (2013.01); *C08G 61/08* (2013.01); *H01L 51/004* (2013.01); *H01L 51/0043* (2013.01); *H05B 33/20* (2013.01); *C08G 2261/149* (2013.01); *C08G 2261/418* (2013.01); *H01L 51/007* (2013.01); *H01L 51/0072* (2013.01); *H01L 51/5016* (2013.01)

(58) Field of Classification Search
CPC .. C07D 413/10; C07D 413/14; C08F 120/36; C08F 12/14; C08F 220/36; C08F 232/08; C08G 2261/149; C08G 2261/418; C08G 61/08; H01L 51/004; H01L 51/0043; H01L 51/007; H01L 51/0072; H01L 51/5016; H01L 51/50; H05B 33/20; H05B 33/14; C09K 11/00
See application file for complete search history.

(56) References Cited

U.S. PATENT DOCUMENTS

| | | | | |
|---|---|---|---|---|
| 8,580,396 B2* | 11/2013 | Liu et al. | | 428/690 |
| 2002/0135296 A1* | 9/2002 | Aziz et al. | | 313/504 |
| 2003/0215669 A1* | 11/2003 | Kathirgamanathan et al. | | 428/690 |
| 2004/0247933 A1 | 12/2004 | Thoms | | |
| 2007/0222376 A1* | 9/2007 | Ohsawa et al. | | 313/506 |
| 2008/0149923 A1* | 6/2008 | Ohsawa et al. | | 257/40 |
| 2008/0230747 A1* | 9/2008 | Nomura et al. | | 252/301.16 |
| 2014/0175400 A1* | 6/2014 | Liu et al. | | 257/40 |

Typical Multi-layer Configuration of OLED Devices

FOREIGN PATENT DOCUMENTS

| | | | |
|---|---|---|---|
| CN | 1854136 | * | 11/2006 |
| CN | 101314635 A | * | 12/2008 |
| EP | 1 972 625 A1 | | 9/2008 |
| JP | 2002-302516 | | 10/2002 |
| WO | WO-2009/026235 | | 2/2009 |
| WO | WO-2009/080797 | | 7/2009 |
| WO | WO-2009/080799 | | 7/2009 |

OTHER PUBLICATIONS

Translation of CN 1854136 A (publication date Nov. 2006).*
Translation of CN 101314635 A (publication date Dec. 2008).*
Zhang et al., Chem. Mater., (2008), vol. 20, pp. 7324-7331.*
Zhang et al., Macromolecular Rapid Communications, (2008), vol. 29, pp. 1817-1822.*
Boyd, T. et al. "Electroluminescence from New Polynorbornenes That Contain Blue-Light-Emitting and Charge-Transport Side Chains", Macromolecules, 1997, vol. 30, pp. 3553-3559.
Cacialli, F. et al. "Light-emitting diodes based on poly(methacrylates) with distyrylbenzene and oxadiazole side chains", Synthetic Metals, 1995, vol. 75, pp. 161-168.
Domercq, B. et al. "Photo-Patternable Hole-Transport Polymers for Organic Light-Emitting Diodes", Chem. Mater., 2003, vol. 15, pp. 1491-1496.
Furstner, A. "Olefin Metathesis and Beyond", Angewandte Chemie International Addition, 2000, vol. 39, Issue 17, pp. 3013-3043.
Guan et al. "High-performance blue electroluminescent devices based on 2-(4-biphenylyl)-5-(4-carbazol-9-yl)phenyl-1, 3, 4-oxadiazole", Chemical Communications—Chemcom, Royla Society of Chemistry, Jan. 1, 2003, No. 21, pp. 2708-2709.
Hreha, R. et al. "Synthesis of Photo-Crosslinkable Hole-Transport Polymers with Tunable Oxidation Potentials and Their Use in Organic Light-Emitting Diodes", Synthesis, Mar. 2002, No. 9,pp. 1201-1212.
International Search Report in PCT/EP2010/058732 dated Sep. 15, 2010.
Jiang, X. et al. "Effect of carbazole-oxadiazole excited-state complexes on the efficiency of dye-doped light-emitting diodes", Journal of Applied Physcis, May 15, 2002, vol. 91, No. 10, p. 6717-6724.
Kraft, A. et al. "Electroluminescent Conjugated Polymers-Seeing Polymers in a New Light", Angew. Chem. Int. Ed., 1998, vol. 37, pp. 402-428.
Lehman, E. et al. "Admet Polymerization", In Handbook of Metathesis, 2003, vol. 3, pp. 283-353.

Office Action in U.S. Appl. No. 13/379,599 dated Feb. 27, 2013.
Suzuki, M. et al. "Highly efficient polymer light emitting devices using ambipolar phosphorescent polymer", Applied Physics Letters, 2005, vol. 86, p. 103507.
Trnka, T. et al. "The Development of L2X2Ru=CHR Olefin Metathesis Catalysts: An Organometallic Success Story", Acc. Chem. Res., 2001, vol. 34, pp. 18-29.

* cited by examiner (Continued)

*Primary Examiner* — Dawn Garrett
(74) *Attorney, Agent, or Firm* — Pabst Patent Group LLP

(57) ABSTRACT

The inventions describe disclosed and described herein relate to ambipolar small molecule host materials for guest phosphorescent metal complexes. Methods of making the ambipolar small molecules are also described. These ambipolar small molecules, which comprise both an oxadiazole and one or more carbazole groups, can be used to make the emission layers of unexpectedly efficient OLED devices containing the materials of the inventions, wherein (I) at least one of the $R^1$, $R^2$ and $R^3$ groups is an optionally substituted carbazole group.

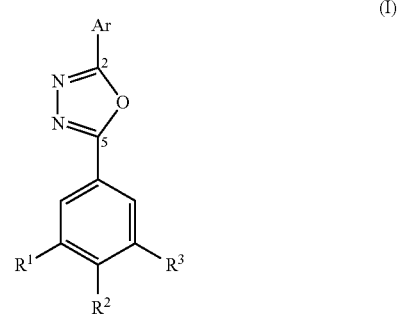

15 Claims, 21 Drawing Sheets

Figure 2. Typical Multi-layer Configuration of OLED Devices (I₁): R₁ = R₃ = H; R₂ = Carbazole
(I₂): R₁ = R₃ = Carbazole; R₂ = H
(I₃): R₁ = R₂ = H; R₃ = Carbazole (II₁): R₁ = R₃ = H; R₂ = Carbazole
(II₂): R₁ = R₃ = Carbazole; R₂ = H
(II₃): R₁ = R₂ = H; R₃ = Carbazole (III$_1$) : R$_1$ = R$_3$ = H; R$_2$ = Carbazol; x = 5
(III$_2$) : R$_1$ = R$_3$ = Carbazol; R$_2$ = H; x = 5
(III$_3$) : R$_1$ = R$_2$ = H; R$_3$ = Carbazol; x = 1

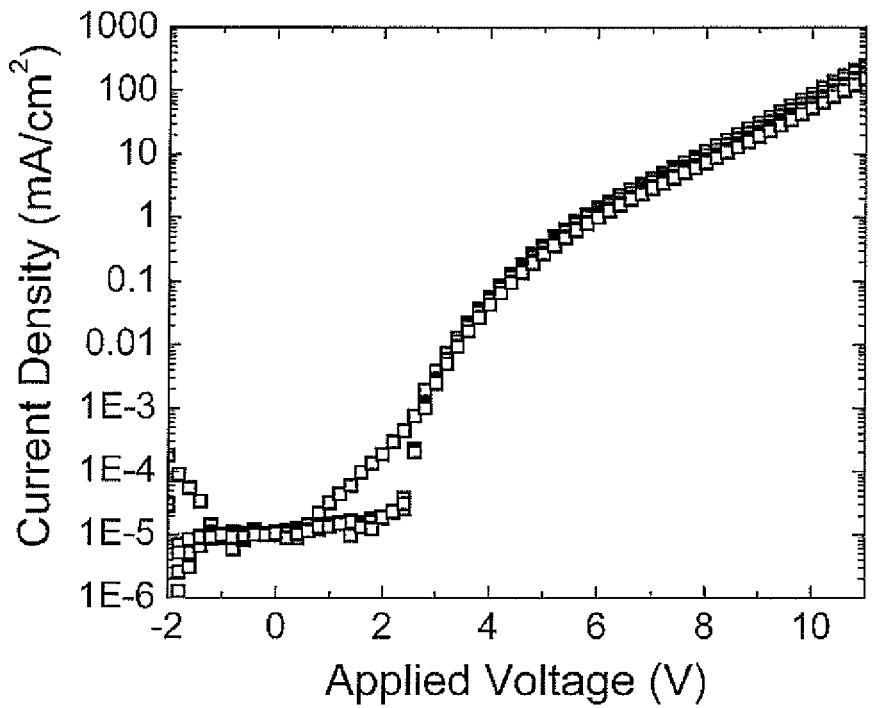
Figrue 19a
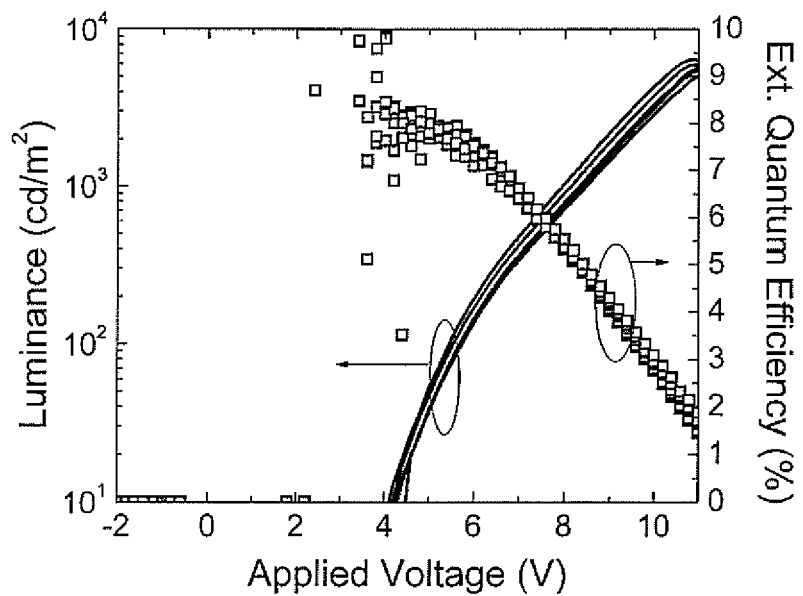
Figure 19b

AMBIPOLAR SMALL MOLECULE HOSTS FOR PHOSPHORESCENT GUEST EMITTERS

RELATED APPLICATIONS

This application claims the priority of U.S. Provisional Application No. 61/220,116 filed 24 Jun. 2009. The entire disclosure is hereby incorporated herein by reference in its entirety.

STATEMENT OF GOVERNMENT LICENSE RIGHTS

The inventors received partial funding support through the STC Program of the National Science Foundation under Agreement Number DMR-020967 and the Office of Naval Research through a MURI program, Contract Award Number 68A-1060806. The Federal Government may retain certain license rights in this invention.

TECHNICAL FIELD OF THE INVENTION

The inventions disclosed and described herein relate to polymeric ambipolar host materials that can transport all of electrons, holes, and/or excitons to guest phosphorescent materials so as to form the emission layers of organic light emitting diodes (OLEDs). Methods of making the ambipolar polymers or copolymers from novel monomeric ambipolar materials, and ambipolar small molecules are also described, as are unexpectedly efficient OLED devices containing the ambipolar host materials.

BACKGROUND OF THE INVENTION

Considerable research has been directed toward the synthesis of organic light-emitting diodes (OLEDs), in view their potential applications in full-color flat panel displays and solid state lighting. Such OLEDs often contain a light emissive layer comprising a luminescent material as a guest, dispersed and/or dissolved in a mixture of host/carrier materials capable of transporting holes, electrons, and/or excitons into contact with the luminescent guest. The luminescent guest is excited by the electrons, holes, and/or excitons, and then emits light. The light emissive layer is typically disposed between an anode and cathode. Single layer OLED devices are known, but typically exhibit very low quantum efficiencies, for a variety of reasons. Efficiency has been dramatically improved in some cases by employing additional layers of materials in the OLED devices, such as an additional layer comprising a material whose properties are optimized for transporting holes into contact with the emission layer, and/or an additional electron transport layer comprising a material whose properties are optimized for carrying electrons into contact with the emission layer. Upon application of voltage/current across the OLED devices, holes and electrons are transported through the intermediate layers and into the emissive layer, where they combine to form excitons and/or stimulate the formation of excited states of the luminescent guest material.

The luminescent guest materials can either be fluorescent materials that emit from a singlet excited state, or phosphorescent materials that emit light from a triplet excited state. While phosphorescent triplet emitters can potentially produce significantly enhanced quantum efficiencies as compared with singlet fluorescent emitters, the use of materials that emit from triplet states imposes additional requirements on the other materials of the OLED devices. In phosphorescent OLEDs, in order to reduce the excited state quenching often associated with relatively long exciton lifetimes and triplet-triplet annihilations, etc., the triplet guest emitters of the emission layers are typically inserted as guests into host materials. All the materials should be selected to optimize efficient injection of charges from the electrodes, in the form of holes, electrons, and the formation of singlet and triplet excitons, that are transferred as efficiently as possible by the host materials to the luminescent guest material.

In order to maximize energy transfer from the host materials to the guest phosphors, the energies of both the singlet and triplet states of the hole and/or electron carrying materials in the host should be higher than the energies of the corresponding singlet and triplet states of the guest phosphors. See FIG. 1. Furthermore, the conjugation length of the host materials should be limited, in order to provide a triplet energy level higher than that of the guest phosphors. Such triplet energy requirements become particularly challenging when designing host molecules that also provide the large charge (hole and/or electron) transport mobilities that are desired.

Thus, development of effective host materials for transporting holes, electrons, and excitons is as important as developing guest phosphors for the production of efficient OLEDs.

High-performance phosphorescent OLEDs with good short term luminescence and efficiency have been reported, but most such prior art devices have been fabricated by expensive multilayer vacuum thermal evaporation of small molecule electron or hole transport materials, to provide multilayer OLED devices, as shown in FIG. 2. For example, host materials comprising carbazoles have been utilized as hole transporter and/or electron blocking materials in OLED applications. Examples of known small molecule carbazole-based hole-carrying materials are shown below. Polymeric carbazoles such as PVK are also known for use in the hole carrying layers of OLED devices.

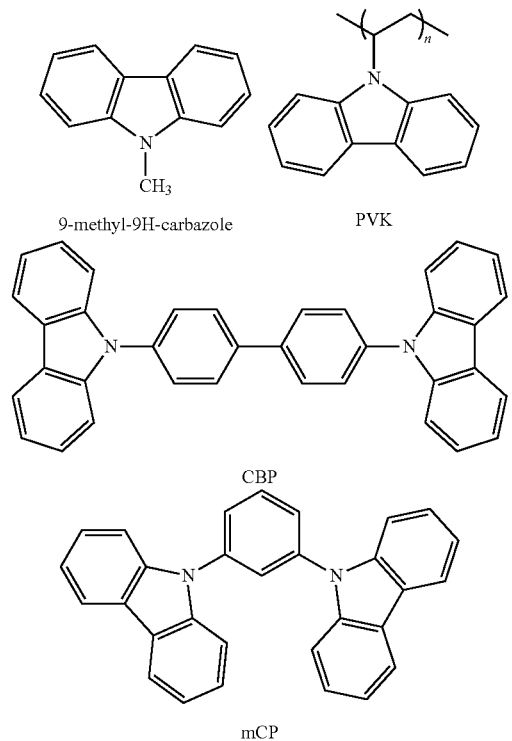

-continued

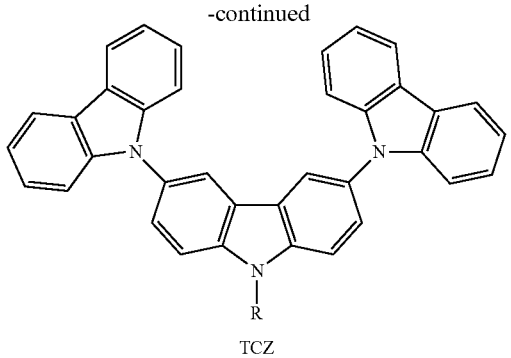

TCZ

Similarly, small-molecule 2,5-diaryl oxadiazoles such as those shown below (PBD and OXD-7) are known as suitable electron carrying materials for use in making electron carrying layers for OLED devices. Polymeric oxadiazole based electron transporting polymers have also been reported, such as for example PCT Application Serial No. PCT/EP/20008 068119 filed 19 Dec. 2008, claiming the priority of U.S. Provisional Application 61/015,777 filed 21 Dec. 2007, both of which are hereby incorporated herein by reference for their disclosures relating to monomeric oxadiazoles useful for preparing the disclosed polymers.

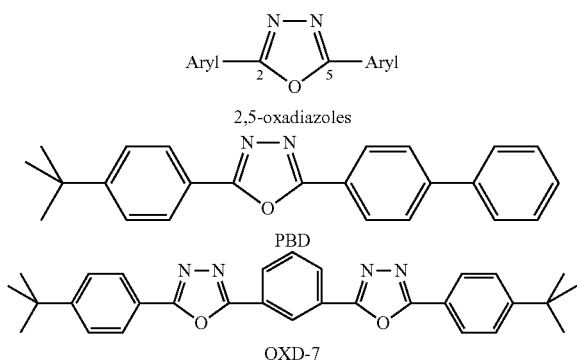

Furthermore, the use of "ambipolar" mixtures of hole carrying and electron carrying materials to form a mixed host material for phosphorescent guests in the emissions layers of multi-layer OLEDs are known. Nevertheless, devices based on mixtures of hole carrying and electron carrying materials in their emission layers, whether based on mixtures of small molecules and/or polymers tend to undergo phase separations, undesirable partial crystallizations, and/or otherwise degrade upon extended OLED device heating, decreasing OLED device efficiency and/or lifetimes over time.

Accordingly, there remains a need in the art for improved "ambipolar" host materials that can efficiently transport holes, electrons, and/or excitons into contact with phosphorescent guests in emission layers, without undergoing phase separations, crystallization, or thermal or chemical degradation. Furthermore, if a single "ambipolar" amorphous and polymeric host material could be used to transport holes, electrons, and/or excitons into contact with phosphorescent guests, it is possible that one or more of the electron carrying or hole carrying layers of the multi-layer OLED devices could be omitted, simplifying device design and manufacture, and lowering fabrication costs, especially if high cost vacuum deposition techniques could be replaced with lower cost solution processing techniques.

It is to that end that the various embodiments of the ambipolar polymers, copolymers, and materials and methods for their preparation described below are directed.

SUMMARY OF THE INVENTION

The various inventions and/or their embodiments disclosed herein relate to and include "ambipolar" polymers, "ambipolar" copolymers, and ambipolar small molecules having both hole carrying and electron carrying groups bound thereto, and the use of such ambipolar polymers, copolymers, and/or small molecules as host materials for carrying holes, electrons, and/or excitons into contact with guest light emitters, for use in the emissive layers of electronic devices such as organic light emitting diodes.

Some embodiments of the inventions described and/or claimed herein relate to "ambipolar" homopolymers or copolymers that have at least one hole carrying group and at least one electron carrying group bound to the same subunit of the homopolymer or copolymer backbone. A related but different class of ambipolar copolymers have the hole carrying groups and the electron carrying groups bound to different subunits of the polymer or copolymer backbone. Many of these classes of ambipolar homopolymers and copolymers are readily soluble in common organic solvents, and therefore can be readily processed in solution (via processes like spin coating or printing) to make layers in organic electronic devices, such as, when co-deposited with phosphorescent metal complexes, emissive layers of OLED devices.

Many different types of polymer and/or copolymer backbones derived from polymerizable monomers can be employed to make the homopolymers and copolymers described herein, including for example polymerized styrenes, acrylates, methacrylates, and the like, epoxides, hydroxyacids for forming polyesters, aminoacids for forming polyamides, isocyanides for forming polyisocyanates, and the like, as well as ring opening metathesis polymerization, ROMP, polymerized cyclic olefins such as polynorbornenyl polymer backbones.

Furthermore, some embodiments of the inventions described and/or claimed herein relate to "ambipolar" "small molecules" that have at least one hole carrying group and at least one electron carrying group, which can either be solution processed or vacuum sublimed to form organic electronic devices.

Examples of suitable hole carrying groups bound and/or linked to the ambipolar monomers, polymers, copolymers, and/or small molecules include but are not limited to variously substituted carbazole groups having the basic carbazole ring structure shown below:

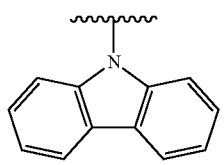 [SMILES: *n1c2ccccc2c2ccccc21]

Examples of suitable electron carrying groups bound and/or linked to the ambipolar small molecules, monomers, polymers and/or copolymer include but are not limited to variously substituted 2,5-diaryl-1,3,4-oxadiazole groups (often referred to below as "oxadiazole" groups). Further details regarding suitable carbazole and oxadiazole groups are provided below.

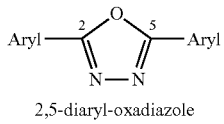

2,5-diaryl-oxadiazole

In many embodiments, the inventions relates to monomers, polymers or copolymers wherein at least one of the polymer or copolymer subunits is linked to at least one carbazole group and also at least one oxadiazole group.

To provide non-limiting examples, some embodiments of the inventions relate to ambipolar polymers or copolymers having at least one, or more, polymerized styrene (i.e. class (I)), acrylate or methacrylate (class (II)), or norbornene (class (III)) subunits in their polymer backbones, wherein at least some of the polymer or copolymer subunits is linked to at least one carbazole group and also at least one oxadiazole group.

In additional embodiments, ambipolar norbornenyl copolymers of a different class (IV) contain hole carrying groups such as carbazoles and electron carrying groups such as for example oxadiazole groups linked to different norbornenyl subunits within the polymer or copolymer backbone. Ambipolar norbornenyl copolymers of class (IV) can also comprise optional additional subunits derived from a wide variety of additional polymerizable monomers. In such embodiments, the ambipolar copolymers described herein can comprise a. at least one first norbornenyl subunit linked to at least one optionally substituted carbazole group; and
 b. at least one second norbornenyl subunit linked to an optionally substituted 2-phenyl-5-phenyl-1,3,4-oxadiazole group; and
 c. optionally one or more additional polymer subunits.

For example, in some embodiments, ambipolar copolymers of class (IVa) shown immediately below are norbornenyl copolymers that have at least some, subunits having each of the structures shown below:

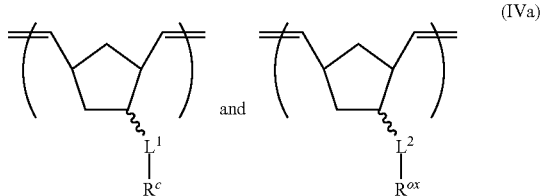

(IVa)

wherein
 a. $L^1$ and $L^2$ are independently selected $C_1$-$C_{20}$ organic linking groups,
 b. $R^c$ comprises at least one carbazole group, and
 c. $r^{ox}$ comprises at least one 2-phenyl-5-phenyl-1,3,4-oxadiazole group.

As disclosed above, the copolymers of inventions, including copolymers of classes (I), (II), (III), and (IV), can also comprise one or more additional copolymer subunits as desired. In some such embodiments, the additional copolymer subunits can comprise linkages to crosslinkable groups, or luminescent groups, such as suitable organic phosphors or phosphorescent metal complexes.

The ambipolar polymers and copolymers of the inventions can be prepared by any of a variety of polymerization methods as would be obvious to one of ordinary skill in the art in view of the disclosures herein. For example, norbornenyl copolymers wherein some subunits are linked to carbazole groups and other subunits are linked to oxadiazole subunits can be prepared by a process comprising the steps of a. mixing
  i. at least one first norbornene monomer comprising a norbornene group linked to a carbazole group; and
  ii. at least one second norbornene monomer comprising a norbornene group linked to an optionally substituted 2-phenyl-5-phenyl-1,3,4-oxadiazole group; and
  iii. optionally one or more additional optionally substituted norbornene monomers; and
 b. polymerizing the mixture of norbornene monomers in the presence of a ROMP catalyst, to produce the copolymer.

In other embodiments, ambipolar copolymers comprising subunits that each are linked to both a carbazole subunit and an oxadiazole subunit can be prepared by polymerization (in some case radical in others living) or copolymerization of suitable monomer compounds, such as substituted styrene monomers (Ia), substituted acrylate or methacrylate monomers (IIa) or substituted norbornene monomers (IIIa)

Other embodiments of the inventions disclosed herein relate to methods for preparing compounds (Ia), (IIa), or (IIIa), as well as certain novel intermediates used for their synthesis.

Further detailed description of preferred embodiments of the various ambipolar polymers and copolymers and methods and materials for their preparation broadly outlined above will be provided in the Detailed Description section below.

BRIEF DESCRIPTION OF THE FIGURES

FIG. 18a shows the current density versus voltage characteristics of an OLED device comprising an emissive layer comprising 2-(3,5-Dicarbazol-9-ylphenyl)-5-(3-methoxyphenyl)-1,3,4-oxadiazole as a hole and electron carrying host and FIrpic as an emissive guest, and PVK as a hole-transmission layer, as described in Example 7a.

FIG. 19a shows the current density versus voltage characteristics of an OLED device comprising an emissive layer comprising 2-(3,5-Dicarbazol-9-ylphenyl)-5-(3-methoxyphenyl)-1,3,4-oxadiazole and 6% FIrpic as an emissive guest, and TCZ as a hole-transmission layer, as described in Example 7a. FIG. 19b shows the luminescence and external quantum efficiency versus voltage performance of the OLED device.

FIG. 20 shows a generic synthetic scheme for making a series of 2-(3,5-Dicarbazol-9-ylphenyl)-5-(substituted-phenyl)-1,3,4-oxadiazoles as reported in Example 7a.

DETAILED DESCRIPTION OF THE INVENTION

Figure 1:
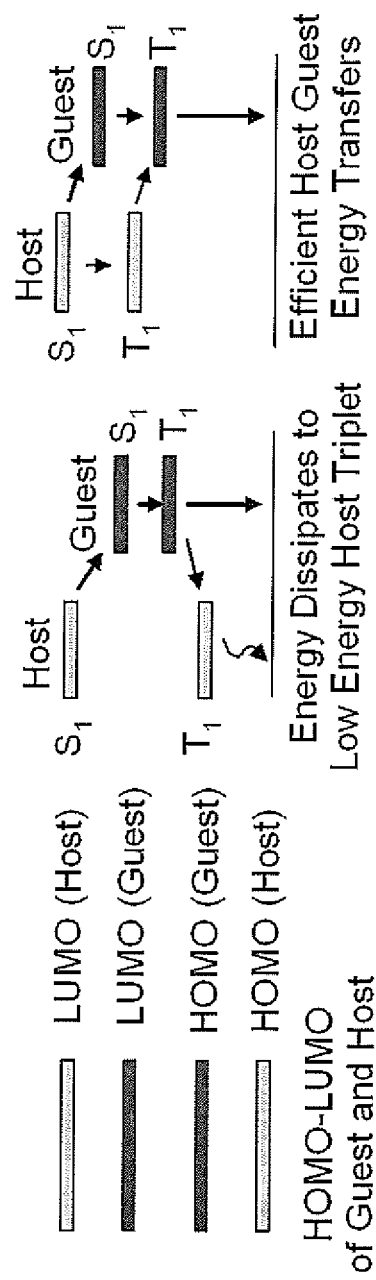
FIG. 1 shows a schematic diagram of the energetics of the HOMOs and LUMOs and their corresponding singlet and triplet excited states for both host and guest materials used the emission layers of OLED devices, and how they can be matched to produce good energy transfer to the phosphorescent guests, or mismatched so as to provide pathways for energy dissipation.
Figure 2:
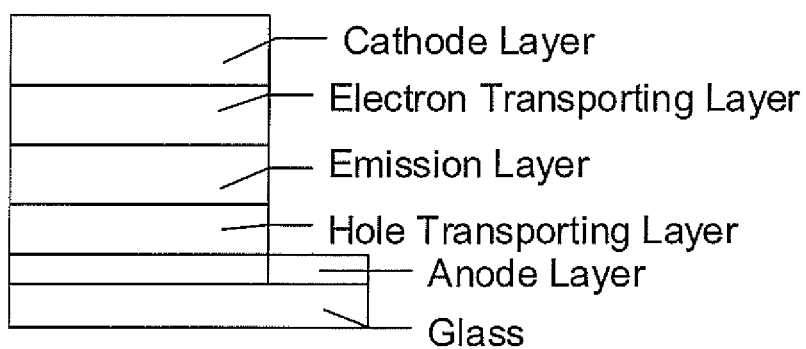
FIG. 2 shows a common physical configuration of multilayer OLED devices.

The various inventions and/or their embodiments disclosed herein relate to and include "ambipolar" polymers and copolymers that are bound and/or linked to both hole carrying and electron carrying groups. Those ambipolar polymers and/or copolymers are useful as host materials for luminescent guests, and are capable of carrying holes, electrons, and excitons into contact with the guests. The combined host/guest combinations comprising the polymers and/or copolymers described herein are useful as materials for making the emissive layers of electronic devices such as organic light emitting diodes (OLEDs).

Ambipolar Small Molecules, Polymerizable Monomers, and/or Polymers or Copolymers Some embodiments of the inventions described and/or claimed herein relate to "ambipolar" small molecules, polymerizable monomers, and polymers and/or copolymers that have polymer subunits, each of which have at least one hole carrying group and at least one electron transporting group bound and/or bonded into or linked thereto.

At least one and sometimes more hole carrying groups are chemically and/or covalently bound into the ambipolar small molecules, polymerizable monomers, and/or linked to the subunits of the polymer and copolymer chains. Examples of suitable hole-carrying groups bound and/or linked to the polymer subunits include but are not limited to variously substituted carbazole groups having the basic ring structure shown below:

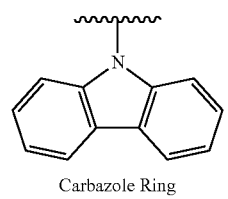 [SMILES: *n1c2ccccc2c2ccccc21]

Carbazole Ring

Examples of suitable electron transporting groups also bound into the ambipolar small molecules and polymerizable monomers, and/or linked to the polymer and/or copolymer backgrounds include but are not limited to variously substituted 2,5-diaryl-1,3,4-oxadiazole groups (shown below and typically referred to herein as "oxadiazole" groups).

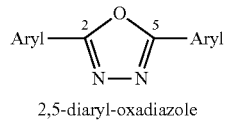

2,5-diaryl-oxadiazole

In many embodiments, the ambipolar small molecules, polymerizable monomers, and/or polymers and/or copolymers of the invention comprise at least one optionally substituted carbazole group and at least one optionally substituted 2,5-diaryl-1,3,4-oxadiazole group.

Accordingly, in many embodiments, the inventions described and/or claimed herein relate to ambipolar small molecules, polymerizable monomers, and the polymers and copolymers derived therefrom, that comprise an electron transporting 1,5-diaryl 1,3,4-oxadiazole group that is bonded to a carbazole group and also linked to an aryl or heteroaryl "Ar" group, a polymerizable group, or a polymer or copolymer derived therefrom, as shown below:

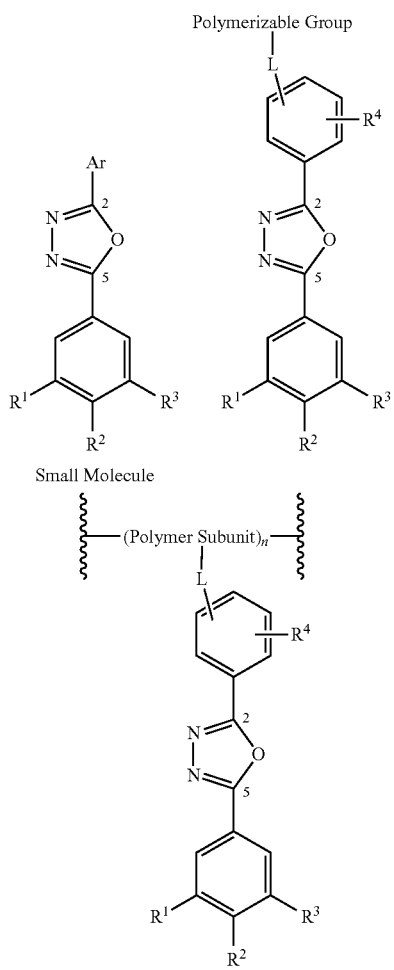

wherein Ar is an optionally substituted aryl or heteroaryl group, n is an integer representing the number of polymer subunits, L is a linking group connecting the monomeric polymerizable group or polymer subunit(s) to the 2-phenyl ring of the oxadiazole group, and at least one of the $R^1$, $R^2$ and $R^3$ groups is an optionally substituted carbazole group having the structure

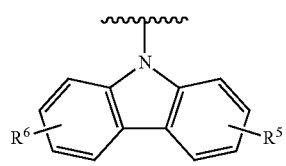

wherein the various embodiments of the remaining $R^1$, $R^2$, $R^3$, and optional $R^4$, $R^5$, and $R^6$ groups are described below.

Such ambipolar small molecules, monomers and the polymers or copolymers derived therefrom can be unexpectedly effective as hole and/or electron transport compounds and/or exciton forming and transporting compounds and can be used to make highly efficient and stable OLED devices. Moreover, the ambipolar small molecules, monomers and/or polymers or copolymers derived therefrom can have unexpectedly superior physical properties, such as high solubility and processability, and/or high resistance to crystallization and/or thermal degradation during OLED operation.

Ambipolar Small Molecules

In some embodiments, the inventions described and/or claimed herein include certain ambipolar "small molecules", for example a compound comprising an optionally substituted aryl or heteroaryl group bonded to a 1,3,4-oxadiazole group having one or more carbazole groups bound thereto, the compound having the formula:

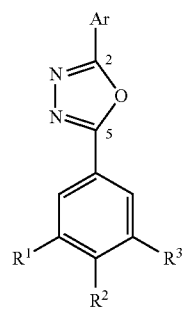

wherein
a. Ar is a $C_1$-$C_{30}$ aryl or heteroaryl group optionally comprising one to five substitutent groups;
b. at least one of the $R^1$, $R^2$ and $R^3$ groups is an optionally substituted carbazole group, and the remaining $R^1$, $R^2$ or $R^3$ groups are independently selected from hydrogen, fluoride, cyano, or an alkyl, perfluoroalkyl, alkoxide, and perfluoroalkoxide groups, and optionally one or more additional optionally substituted carbazole groups;

wherein the optionally substituted carbazole groups can have the structure

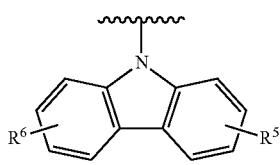

wherein $R^5$ and $R^6$ can be independently selected from hydrogen, fluoride, cyano, and an organic group selected from alkyls, perfluoroalkyls, alkoxides, and perfluoroalkoxides.

The ambipolar small molecules shown above comprise an Ar group that can be an aryl or heteroaryl group optionally substituted with one to five substituent groups. Any suitable optionally aryl or heteroaryl group can be employed, such as for example optionally substituted phenyl, biphenyl, napthyl, fluorenyl, anthracenyl, pyridyl, bipyridyl, thiophenyl, furanyl, or pyrolyl groups. In many embodiments, the optionally substituted aryl or heteroaryl group can be a $C_1$-$C_{30}$, $C_2$-$C_{20}$, or $C_5$-$C_{20}$ group, including the optional substituents. The optional substitutents can be independently selected from non-polymerizable groups such as hydrogen, hydroxyl, fluoride, cyano, or $C_1$-$C_{20}$ alkyl, perfluoroalkyl, alkoxide, or perfluoroalkoxide groups.

Some embodiments of the inventions relate to ambipolar small molecules having the structure

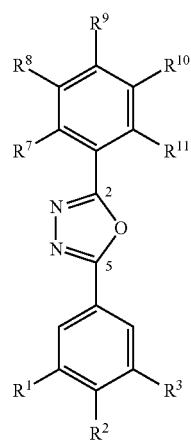

wherein $R^7$-$R^{11}$ are independently selected from hydrogen, fluoride cyano, and a $C_1$-$C_{20}$ alkyl, perfluoroalkyl, alkoxide, or perfluoroalkoxide group.

In many embodiments of the ambipolar small molecules described above (as well as polymerizable monomers, polymers, and copolymers), at least one of the $R^1$, $R^2$ and $R^3$ groups is an optionally substituted carbazole group, and the remaining $R^1$, $R^2$ or $R^3$ groups are independently selected from hydrogen, fluoride, cyano, or a $C_1$-$C_{20}$ alkyl, perfluoroalkyl, alkoxide, or perfluoroalkoxide groups, and optionally one or more additional optionally substituted carbazole groups.

Both the first optionally substituted carbazole group, as well as any additional optionally substituted carbazole groups bound to the first carbazole group, can have the structure

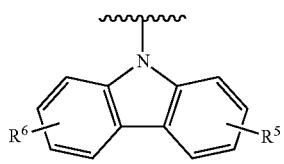

wherein $R^5$ and $R^6$ are independently selected from hydrogen, fluoride, cyano, and a $C_1$-$C_6$ organic group selected from alkyls, perfluoroalkyls, alkoxides, and perfluoroalkoxides. In some embodiments, one of the $R^1$, $R^2$ and $R^3$ groups comprises an optionally substituted carbazole group, and the remaining $R^1$, $R^2$ or $R^3$ groups are hydrogen. In other related embodiments, one of the $R^1$ and $R^2$ groups has the unsubstituted structure

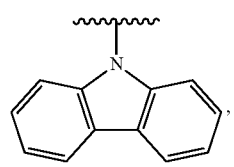 [SMILES: *n1c2ccccc2c2ccccc21]

and the remaining $R^1$, $R^2$ or $R^3$ groups are hydrogen.

Examples of such "monocarbazole" compounds include compounds having the structure

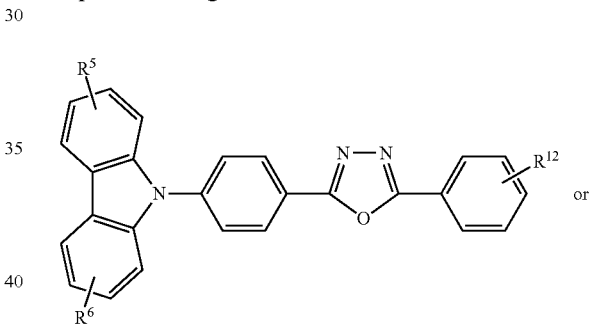

or

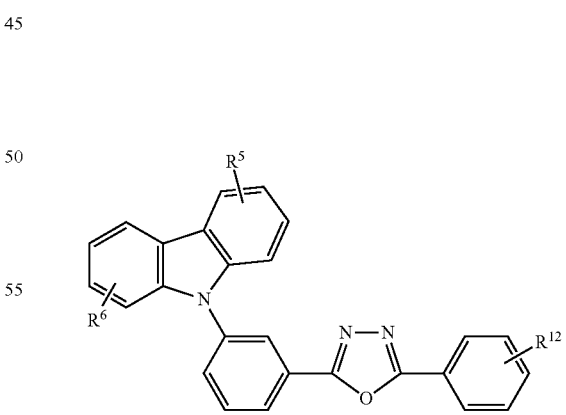

wherein $R^5$, $R^6$, and $R^{12}$ are independently selected from hydrogen, fluoride, hydroxide, cyano, and a $C_1$-$C_6$ organic group selected from alkyls, perfluoroalkyls, alkoxides, and perfluoroalkoxides. Examples of species compounds having these structures whose synthesis is described in the examples include

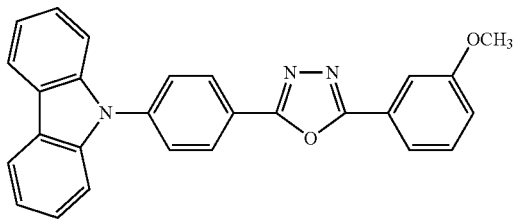

or

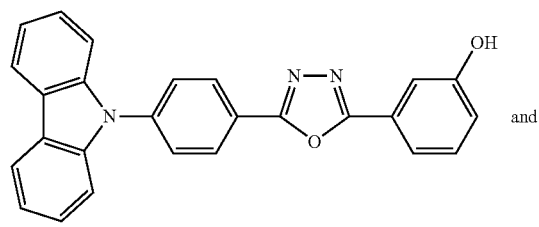

and

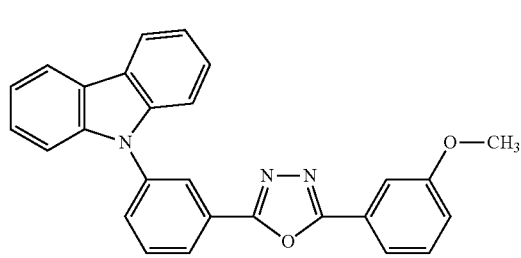

or

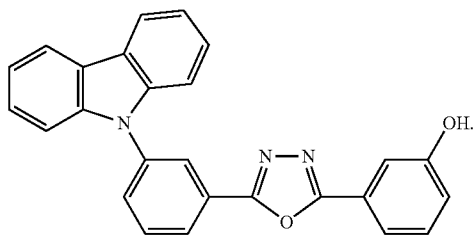

In other embodiments, both the $R^1$ and $R^3$ groups have the structure

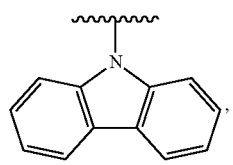 [SMILES: *n1c2ccccc2c2ccccc21]

and $R^2$ is hydrogen. Examples of such compounds include compounds having the structure

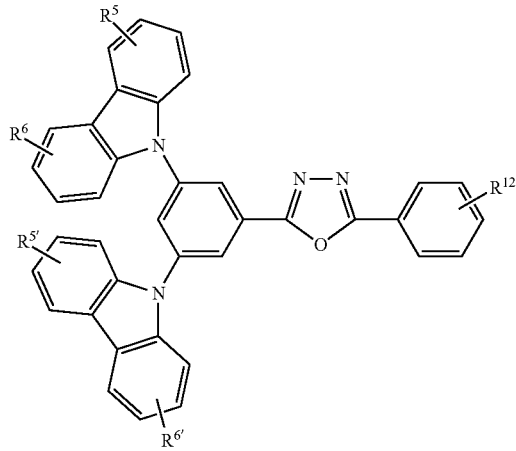

wherein $R^5$, $R^{5'}$, $R^5$, $R^{6'}$, and $R^{12}$ are independently selected from hydrogen, fluoride, cyano, and a $C_1$-$C_6$ organic group selected from alkyls, perfluoroalkyls, alkoxides, and perfluoroalkoxides. An example of a species compound whose synthesis is described in the examples include

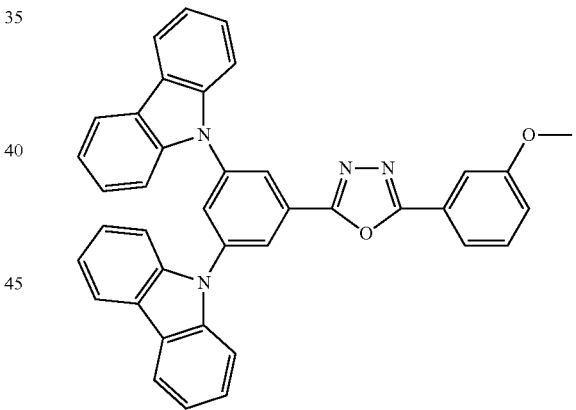

This small molecule compound has been used to form very high efficiency emissive layers in several OLEDs, see Example 7 and FIGS. 17-19.

In yet additional related embodiments, one of the $R^1$, $R^2$ and $R^3$ groups is first optionally substituted carbazole group having "additional" optionally substituted carbazole group bound thereto, such as for example the "tricarbazole groups having the structure

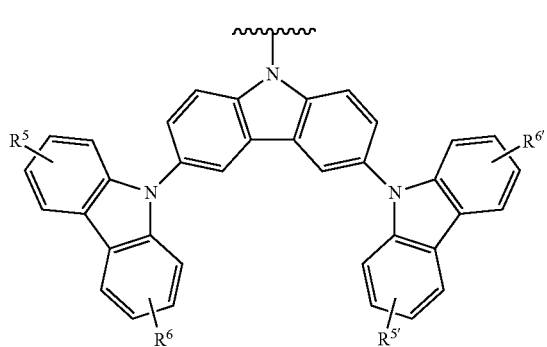

and the remaining $R^1$, $R^2$ or $R^3$ groups are hydrogen. Examples of such compounds include compounds having the structures

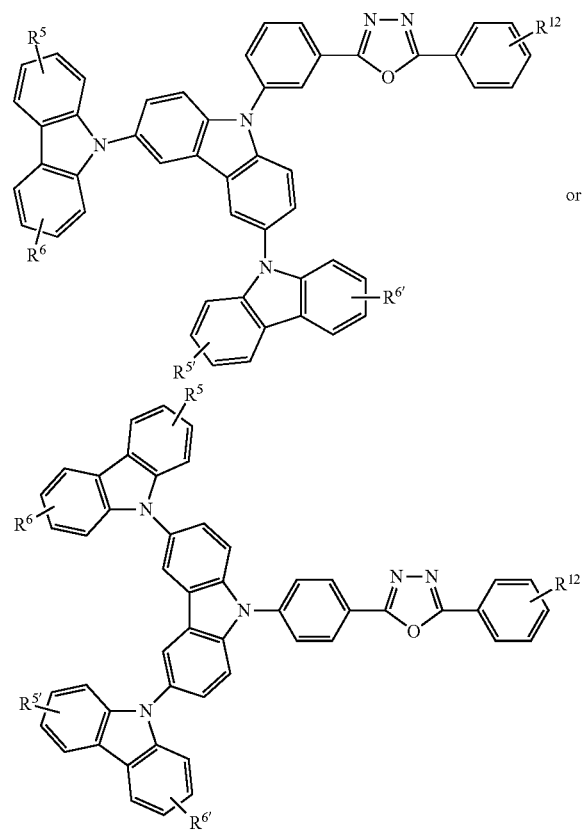

wherein $R^5$, $R^{5'}$, $R^5$, $R^{6'}$, and $R^{12}$ are independently selected from hydrogen, fluoride, cyano, and a $C_1$-$C_6$ organic group selected from alkyls, perfluoroalkyls, alkoxides, and perfluoroalkoxides.

In many embodiments of the optionally substituted carbazole groups, $R^5$, $R^{5'}$, $R^6$, and $R^{6'}$ are hydrogen or t-butyl.

Many of the ambipolar small molecules described above are either sublimable under high vacuum or readily soluble in common organic solvents, and therefore can be readily processed to form compositions useful in organic electronic devices, especially when mixed and/or co-deposited with phosphors, to form the emission layers of organic light emitting diodes.

Furthermore, many of the ambipolar small molecules described above, especially those with hydroxyl or methoxy substituent groups on their Ar rings, can be used as synthetic precursors of ambipolar monomers, polymers, or copolymers described below. It should be understood that any of the disclosures above with respect to the oxadiazole groups, carbazole groups, or their $R^1$-$R^{11}$ substituents are intended to also apply with respect to the teachings below regarding ambipolar monomers, polymers, or copolymers.

Ambipolar Polymers of Classes (I), (II), and (III)

Many embodiments of the inventions described and/or claimed herein relate to "ambipolar" polymerizable monomers, and polymers and/or copolymers linked to ambipolar groups comprising both oxadiazole and carbazole groups.

Many types of polymer and/or copolymer subunits can be bound to ambipolar groups having structures equivalent to those of the ambipolar small molecules described above. For example, polymer backbones comprising subunits derived from styrenes, acrylate esters, methacrylate esters, norbornenes, and the like can be employed, so long as the polymerized chains are resistant to both oxidation by holes, and reduction by electrons present during the operation of electronic devices such as OLEDs. To provide illustrative and non-limiting examples, the "ambipolar polymers and/or copolymers typically have at least one subunit having the structure shown below:

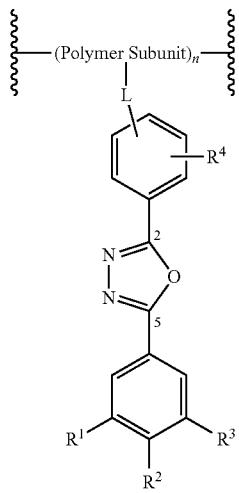

wherein Ar is an optionally substituted aryl or heteroaryl group, n is a positive integer representing the number of polymer subunits, L is a linking group connecting the monomeric polymerizable group or polymer subunit(s) to the 2-phenyl ring of the oxadiazole group, and at least one of the $R^1$, $R^2$ and $R^3$ groups is an optionally substituted carbazole group having the structure

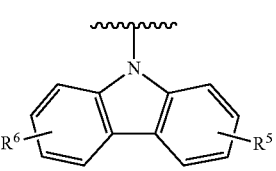

wherein the various embodiments of the remaining $R^1$, $R^2$, $R^3$, and optional $R^4$, $R^5$, and $R^6$ groups are described below.

Such polymers and copolymers can comprise at least one polymerized styrenyl, acryl or methacryl, or norbornenyl subunit having the formulas (I), (II), or (III) illustrated below:

(I)

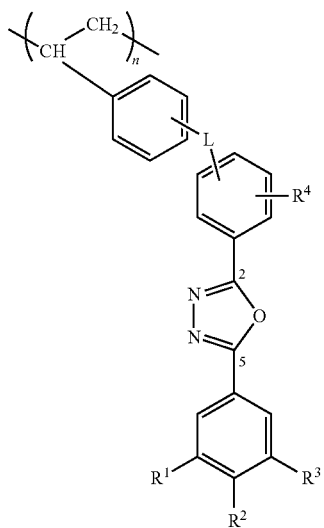

or (II)

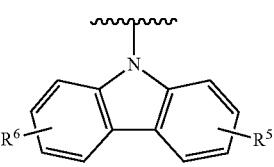

(III)

wherein n is an integer representing the number of polymer subunits, L is a linking group connecting the styrenyl, acryl or methacryl, or norbornenyl subunit(s) to the 2-phenyl ring of the oxadiazole group, and at least one of the $R^1$, $R^2$ and $R^3$ groups is an optionally substituted carbazole group having the structure wherein the identities of the remaining $R^1$, $R^2$, $R^3$, and optional $R^4$, $R^5$, and $R^6$ groups are described above and below, and $R^7$ is hydrogen (acrylate groups) or methyl (methacrylate) groups.

For example, styrenyl compounds of formula (I) having only one carbazole group can have one of the isomeric structures shown below:

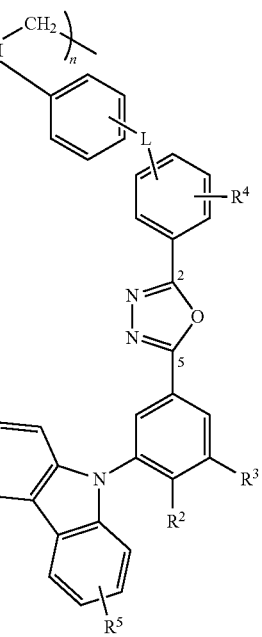

or

-continued

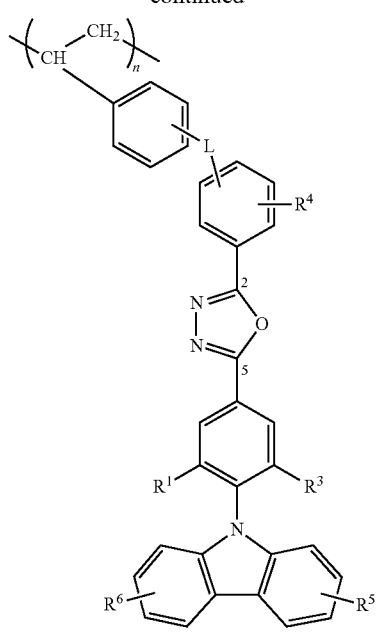

The remaining $R^1$, $R^2$ or $R^3$ groups of the compounds of formulas (I) (II), or (III) can be independently selected from hydrogen and various other substituents as further described above and below, including an additional and optionally substituted carbazole group. If an additional optionally substituted carbazole group is present, such a polymeric styrenyl derivative could have subunits having the exemplary structures such as those shown below:

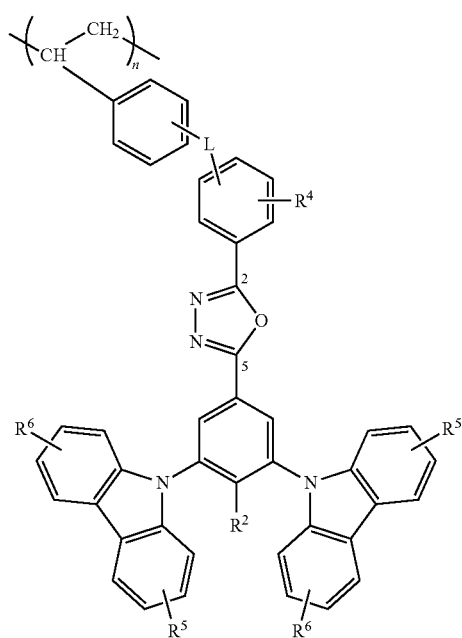

-continued

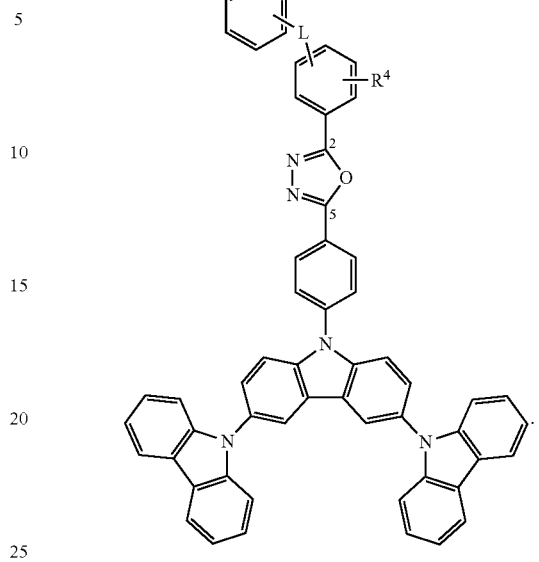

Analogous polyacrylate, polymethacrylate, and/or polynorbornenyl polymers can have at least one subunit having the structures:

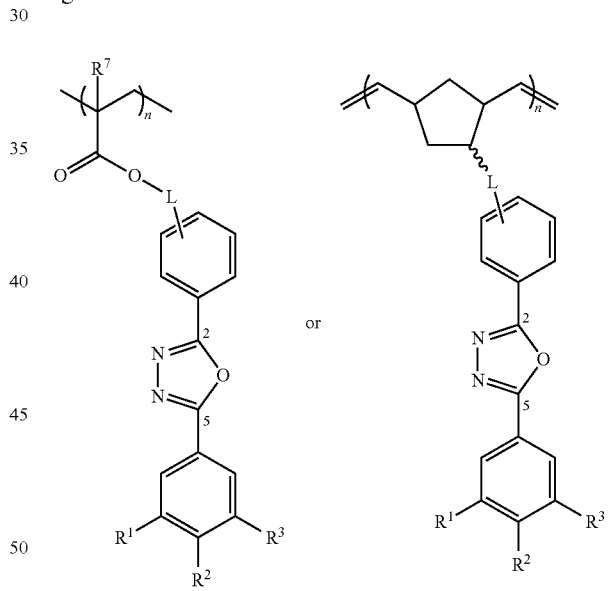

The polymers or copolymers having one or more subunits having formulas (I), (II), or (III) can have a widely varying number of total subunits, as defined by the index n, which can be any integer between 1 and 10000. In some embodiments, n is an integer between 5 and 5000, or between about 20 and 50000. Copolymers having one or more subunits having formulas (I), (II), or (III) can be either random or block copolymers, and the drawings herein and/or "n" indices should not be interpreted as indicating whether the copolymers are random or block unless clearly indicted to the contrary.

The "L" groups of polymer subunits of formulas (I), (II), or (III) link the subunits of the polymer or copolymer backbone to the 2-phenyl rings of the oxadiazole groups. L can be any chemical group that covalently and stably links the polymer or copolymer backbone to the 2-phenyl rings of the oxadiazole groups, such as inorganic atoms or groups such an oxygen or sulfur atom, a sulfate, sulfone, or sulfoxy group, etc, but in many embodiments L is $C_1$-$C_{20}$ organic group, or preferably a $C_1$-$C_4$ or $C_1$-$C_{10}$ organic group which may optionally comprise heteroatoms such as halogens (especially fluoride), O, N, or S. Preferably the L linking group is effectively resistant to oxidation by holes or reduction by electrons under the operating conditions of OLED devices. Examples of L groups are alkylene or alkyleneoxy groups, such as for example wherein L has the structure:

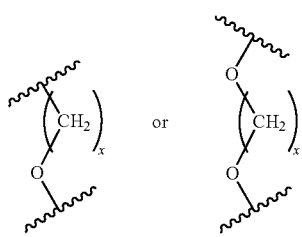

wherein x is an integer from 1 to 20, or from 1 to 12, or from 1 to 4. In some embodiments, L is a methyleneoxy group having the structure:

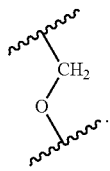 [SMILES: *CO*]

Further examples of L groups include alkylene ester groups as those illustrated below:

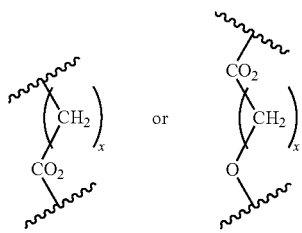

wherein x is an integer from 1 to 20, or from 1 to 12, or from 1 to 4.

The identities of the optional $R^1$, $R^2$, $R^3$, $R^4$, $R^5$, and/or $R^6$ substituent groups for the compounds of formulas (I) and (II) can vary widely, and can include inorganic substituent groups such as hydrogen or halogen (especially fluorine), or $C_1$-$C_{20}$ organic groups, $C_1$-$C_{12}$ organic groups, or $C_1$-$C_6$ organic groups. Examples of preferred organic groups include alkyl, cyano, perfluoroalkyl, alkoxide, or perfluoroalkoxide groups The various embodiments of the $R^1$, $R^2$, $R^3$, $R^4$, $R^5$, $R^6$, and/or $R^7$ groups of the polymers and copolymers can be the same as any of the variety of embodiments of those substituents described above in connection with the ambipolar small molecules. The identities of the $R^1$, $R^2$, $R^3$, $R^4$, $R^5$, and $R^6$, substituent groups can also be rationally varied so as to "tune" the physical and electronic properties of the polymers and/or copolymers to help optimize the efficient transfer of holes, electrons, and/or holes to a luminescent host in the emission layer of an OLED device, and/or provide for improved physical properties and/or lost cost solution processing, and/or application of the polymers during OLED construction, and/or minimize undesirable crystallization, phase separation, and/or thermal decomposition during device operation.

The $R^7$ substituent of the backbones of the polymers and/or copolymers of formula (II) can be any of the substituents disclosed above, but in many embodiments are either hydrogen (polymers or copolymers derived from acrylate esters) or $CH_3$ (polymers or copolymers derived from methacrylate esters).

In some embodiments, the invention relates to styrene-based polymers or copolymers having at least one subunit having the structure

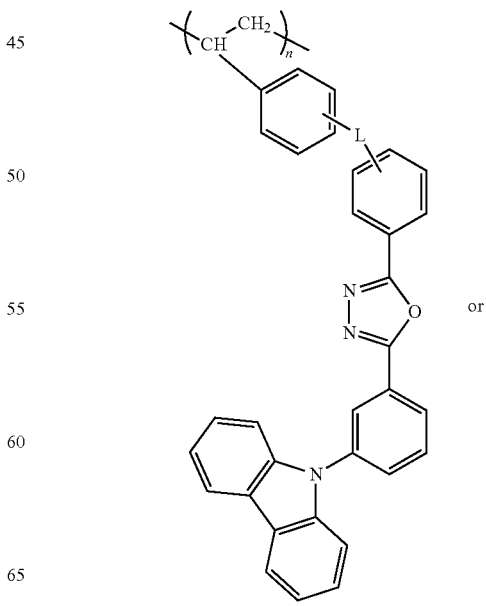

or

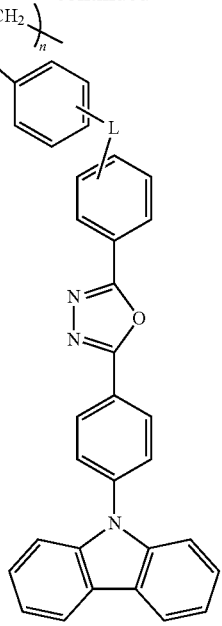
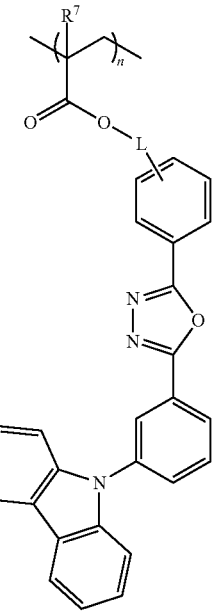
or
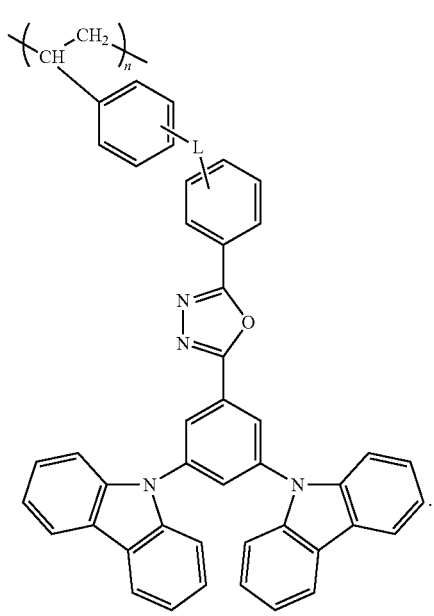
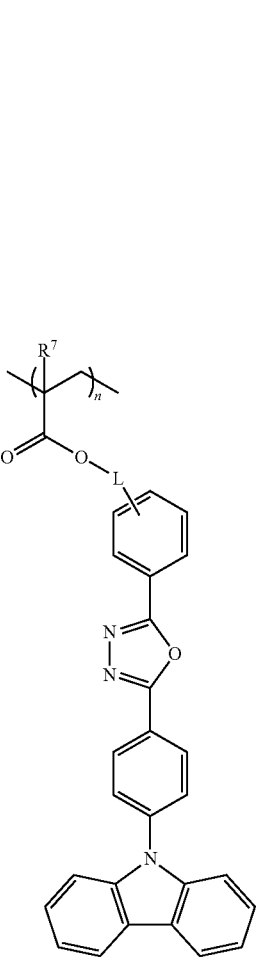
or
In other embodiments, the invention relates to polyacrylate or polymethacrylate-based polymers or copolymers having at least one subunit having the structure

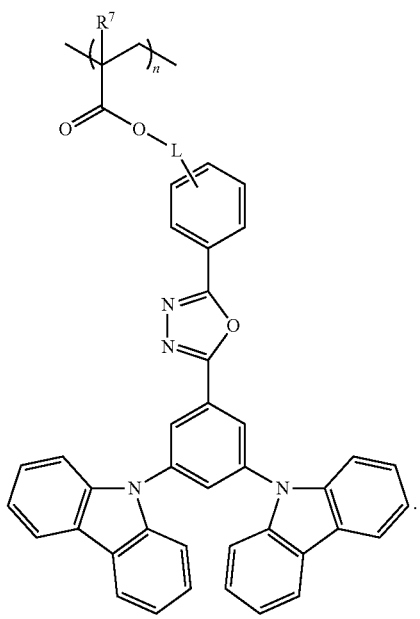

In other embodiments, the invention relates to polynorbornenyl polymers or copolymers having at least one subunit having the structure

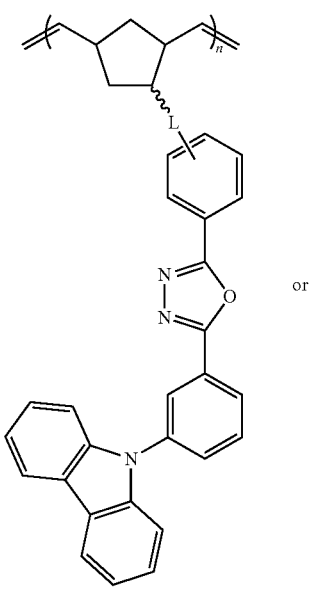

or

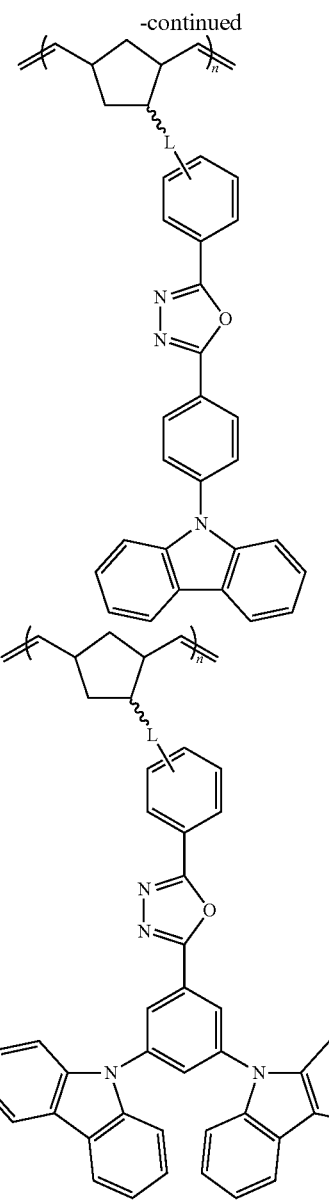

Ambipolar Copolymers of Class (IV)

In additional embodiments of the inventions described herein, ambipolar copolymers of a different class (IV) contain hole carrying groups such as carbazoles and electron carrying groups such as oxadiazole groups linked to different copolymer subunits within the copolymer chains. Copolymers of class (IV) can also contain additional and optional polymerized subunits derived from a wide variety of additional polymerizable monomers, including various optionally substituted vinyl, styrenyl, acryl, methacryl, and/or norbornenyl monomers that can be linked to luminescent groups, such as luminescent metal complexes. In such embodiments, the ambipolar Copolymers of class (IV) described herein can comprise a. at least one first norbornenyl subunit linked to at least one optionally substituted carbazole group; and
b. at least one second norbornenyl subunit linked to an optionally substituted 2-phenyl-5-phenyl-1,3,4-oxadiazole group; and
c. optionally one or more additional polymer subunits.

For example, in some embodiments, ambipolar norbornenyl copolymers of class IVa shown immediately below have at least some subunits having each of the structures shown below:

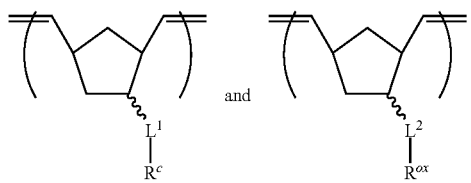

(IVa)

and wherein
a. $L^1$ and $L^2$ are independently selected $C_1$-$C_{20}$ organic linking groups,
b. $R^c$ comprises at least one optionally substituted carbazole group, and
c. $R^{ox}$ comprises at least one optionally substituted 2-phenyl-5-phenyl-1,3,4-oxadiazole group.

Possible structures for the $L^1$ and $L^2$ groups, and possible substituents optionally substituted carbazole groups and optionally substituted 2-phenyl-5-phenyl-1,3,4-oxadiazole groups can be the same as described above for the similar substituent groups of compound classes (I), (H), and (Ill). Some examples of the synthesis of suitable carbazole or oxadiazole monomers for making the copolymers of class (IVa) are provided below, and additional examples were disclosed in PCT Application Serial Nos. PCT/EP/2008 068119 filed 19 Dec. 2008 claiming the priority of U.S. Provisional Application Ser. No. 61/015,777 filed 21 Dec. 2007, and PCT Application Serial No. PCT/EP/2008 068124 filed 19 Dec. 2008 claiming the priority of U.S. Provisional Application Ser. No. 61/015,641 filed 20 Dec. 2007, both of which are hereby incorporated by reference.

For example, the $R^c$ carbazole groups can have exemplary structures such as those shown below:

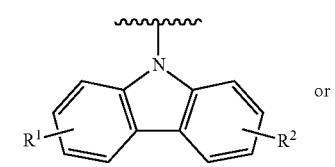

or

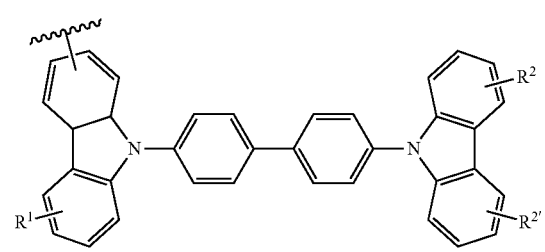

or

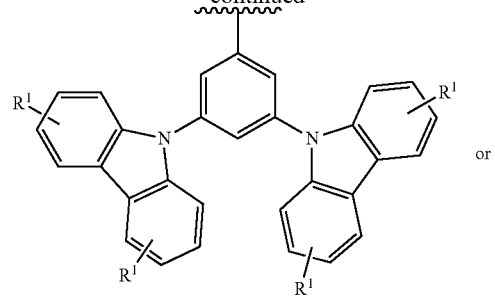

or

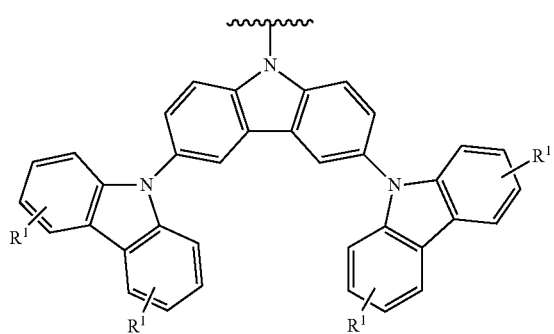

wherein $R^1$ is selected from hydrogen, fluoride, and a $C_1$-$C_6$ organic group selected from alkyls, cyano, perfluoroalkyls, alkoxides, and perfluoroalkoxides.

Similarly, the $R^{ox}$ carbazole groups can have exemplary structures such as those shown below:

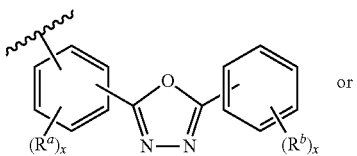

or

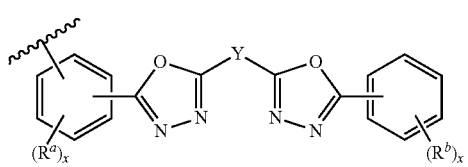

wherein Y is an aryl group, including a phenyl group, and each optional $R^a$ or $R^b$ group is independently selected from hydrogen, fluoride, or one or more $C_{1-20}$ alkyl, cyano, perfluoroalkyl, alkoxy, or perfluoroalkoxy groups, and each x is an independently selected integer 0, 1, 2, 3 or 4.

Specific examples of such ambipolar copolymers can include at least some subunits having the structures shown below

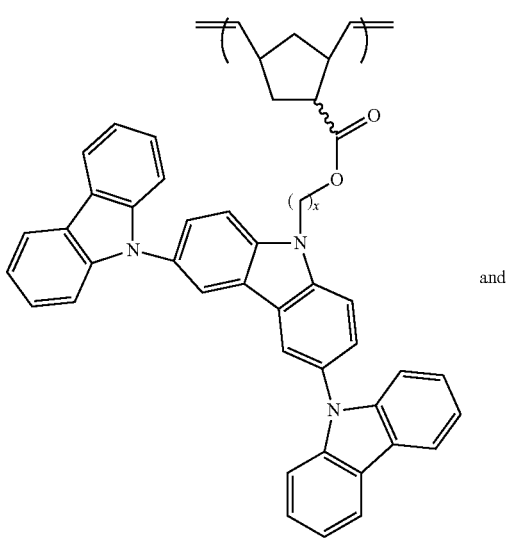

and

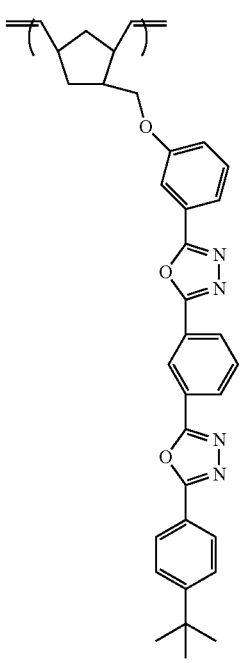

wherein x is an integer from 1 to 20.

As disclosed above, copolymers of class IV can also comprise one or more additional polymer subunits as desired. In some such embodiments, the additional monomers can comprise linkages to luminescent groups, such as suitable organic phosphors or phosphorescent metal complexes. A disclosure of suitable norbornenes linked to phosphorescent Iridium complexes can be found in PCT publication WO 2009/026235 published Feb. 26, 2009, which is incorporated herein by reference for its disclosures of such norbornene-linked phosphorescent Iridium and similar metal complexes.

Polymerizable Ambipolar Monomers

In some aspects, the inventions described herein relate to ambipolar monomers that comprise a polymerizable group linked to both hole carrying and electron carrying groups. For example, in some embodiments, the inventions relate to a monomer comprising a polymerizable group linked to a 2-phenyl-5-phenyl-1,3,4-oxadiazole group having one or more carbazole groups bound thereto, the monomer having the formula:

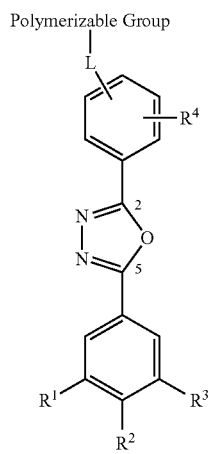

wherein
- a. L is a $C_1$-$C_{20}$ organic group linking the polymerizable group to the 2-phenyl ring of the oxadiazole group;
- b. at least one of the $R^1$, $R^2$ and $R^3$ groups is an optionally substituted carbazole group, and the remaining $R^1$, $R^2$ or $R^3$ groups are independently selected from hydrogen, fluoride, a $C_1$-$C_6$ alkyl, cyano, perfluoroalkyl, alkoxide, or perfluoroalkoxide groups, and optionally one or more additional optionally substituted carbazole groups; wherein the optionally substituted carbazole groups have the structure

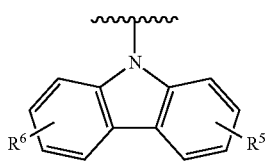

wherein $R^5$ and $R^6$ are independently selected from hydrogen, fluoride, and a $C_1$-$C_6$ organic group selected from alkyls, cyano, perfluoroalkyls, alkoxides, and perfluoroalkoxides;
- c. $R^4$ is selected from hydrogen, fluoride, and a $C_1$-$C_6$ alkyl, perfluoroalkyl, alkoxide, or perfluoroalkoxide group.

Such monomers and the homopolymers and copolymers derived from them are useful as host materials for the manufacture of emission layers of OLED devices, and are capable of transporting holes, electrons, and/or excitons into contact with guest luminescent materials, so as to excite and/or induce luminescence from such guest luminescent materials.

Thus, in some embodiments, the inventions disclosed herein include substituted styrene monomers (Ia), substituted acrylate or methacrylate monomers (IIa), or the substituted norbornene monomers (IIIa) whose structures are shown below:

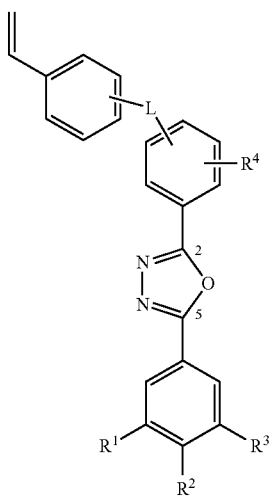

(Ia)

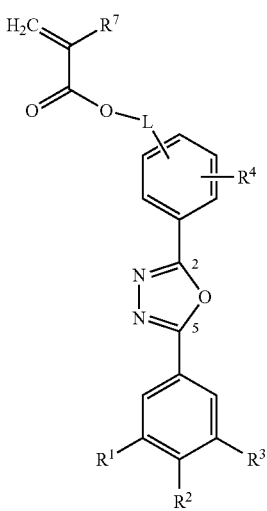

(IIa)

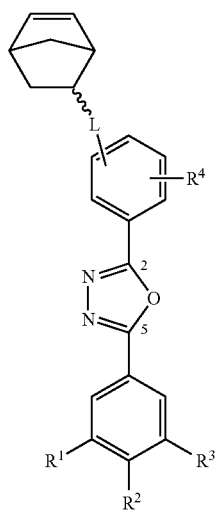

(IIIa)

wherein one or two of the $R^1$, $R^2$ and $R^3$ groups is an optionally substituted carbazole group having the structure

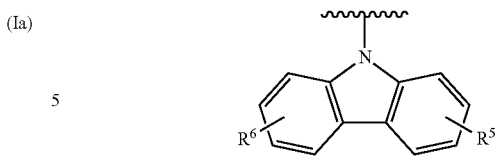

and wherein the index n and the L, $R^1$, $R^2$, $R^3$, $R^4$, $R^5$, $R^6$, and/or $R^7$ groups of one or all of compounds of formula (Ia), (IIa), or (IIIa) can have any of the meanings described above in connection with the corresponding ambipolar small molecules described above, or polymer, or copolymer subunits (I), (II), or (III).

Specific examples of polymerizable ambipolar monomeric styrene compounds of formula (Ia) include compounds having the structures:

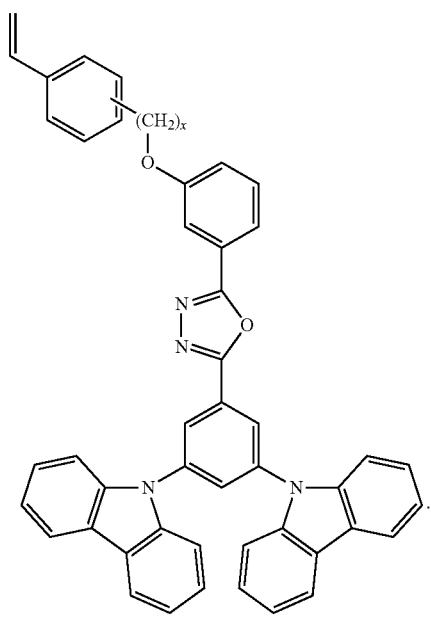

wherein x is an integer between 1 and 20, or 1 and 10.

Specific examples of related polymerizable ambipolar monomeric acrylate or methacrylate compounds of formula (IIa) include compounds having the structures:

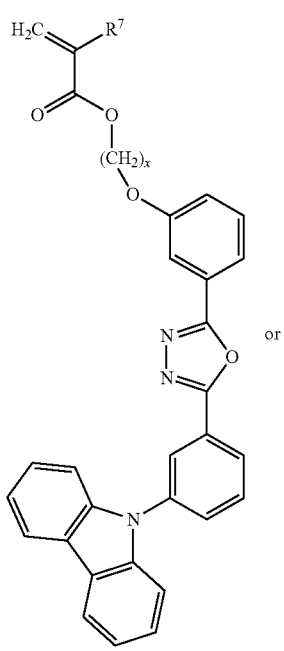

or

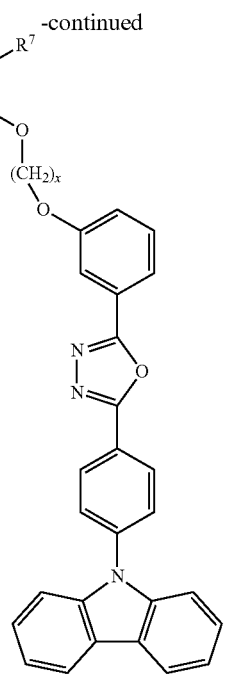

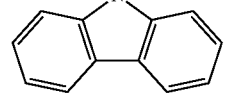

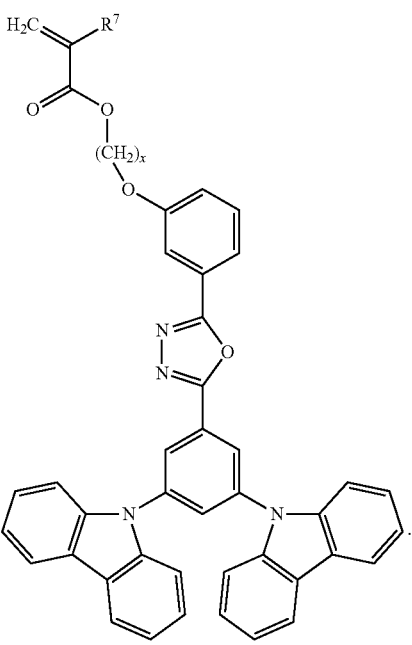

wherein $R^7$ can be hydrogen or $CH_3$.

Specific examples of polymerizable ambipolar monomeric norbornene compounds of formula (IIa) include compounds having the structures:

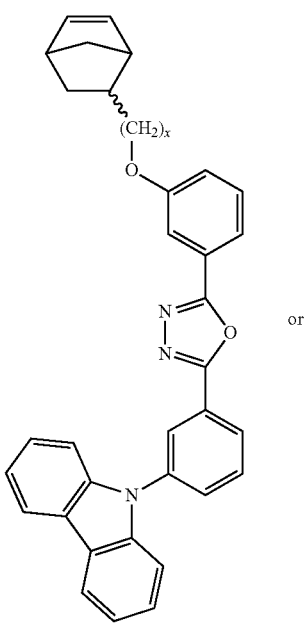

or

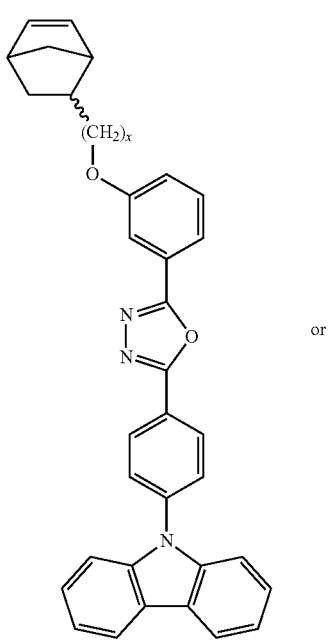

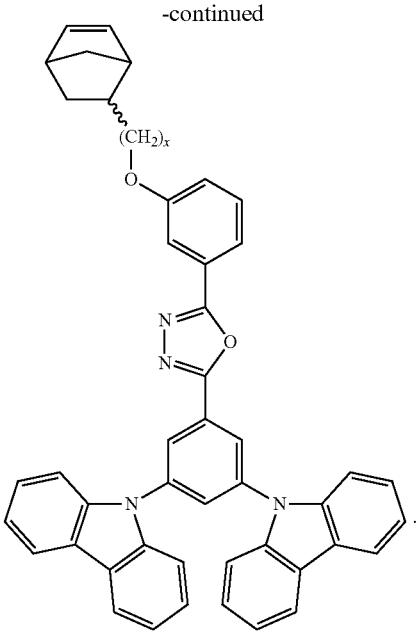

or

Generic schemes for the synthesis of the carbazole/oxadiazole precursors of the phenolic ambipolar monomers above are diagramed in FIGS. 3-8 attached herewith, and specific examples of such syntheses are provided below. Such "ambipolar" precursor compounds are novel, and if the phenolic group is appropriately modified to increase its resistance to oxidation or reduction (by the attachment of appropriate "protecting groups" such as alkyls, aryls, acyls, etc, the resulting intermediate compound can be transformed to be useful as small molecule host materials for the production of OLEDs. Such materials can have the unexpected property of providing a single host material that is capable of transporting holes, electrons, and/or excitons into contact with other guest materials, such as luminescent guest materials.

Furthermore, the phenolic carbazole/oxadiazole precursor compounds disclosed in FIGS. 3-5 can be chemically linked to various polymerizable monomeric groups such as styrenes, acrylates, methacrylates, and norbornenes, as is disclosed in FIGS. 6-8, and specifically exemplified below.

Homopolymerization of Monomers (Ia), (IIa), and (IIIa)

Figure 9A:
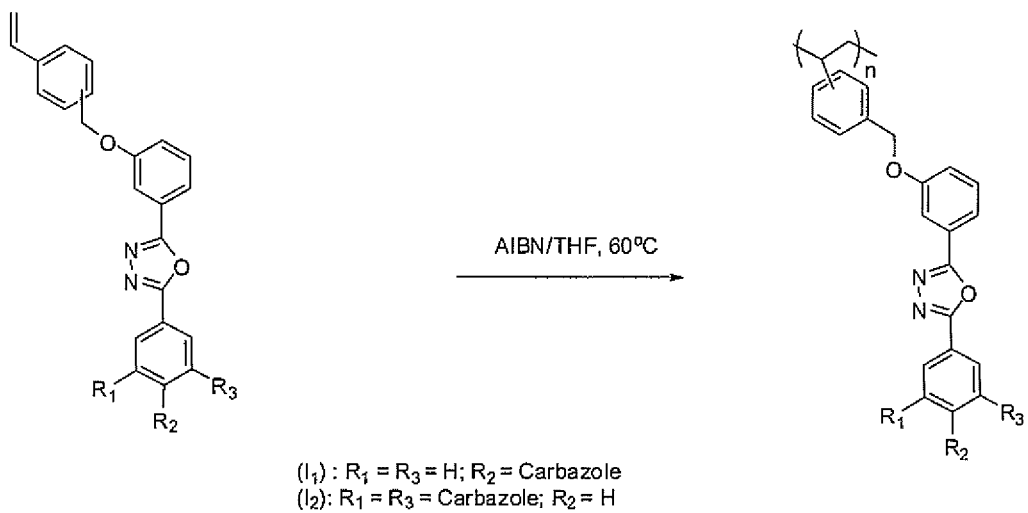
FIG. 9a schematically illustrates the preparation of three ambipolar homopolymers of class (I) by free radical polymerizations of styrene linked ambipolar monomers of classes (Ia).
Figure 9B:
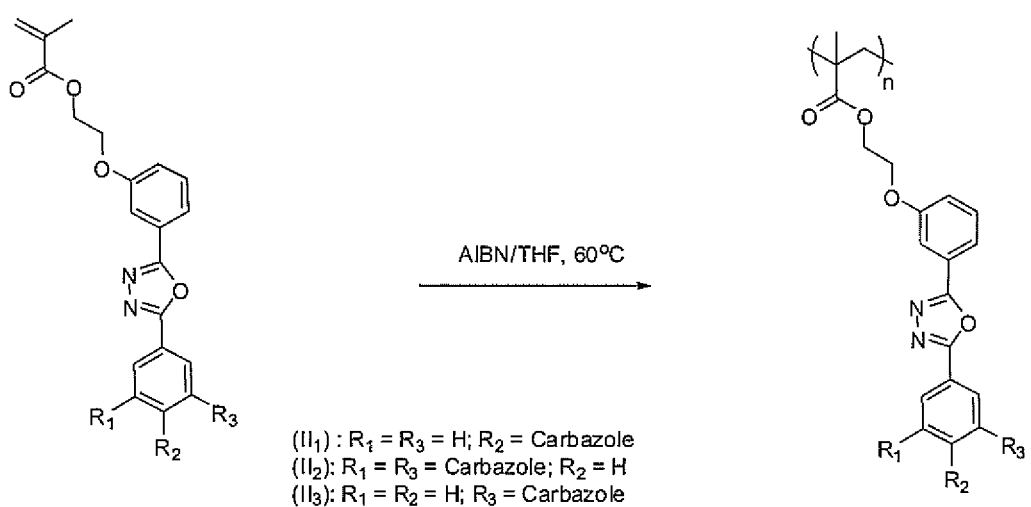
FIG. 9b schematically illustrates the preparation of three=bipolar homopolymers of class (II) by free radical polymerizations of three different methacrylate linked monomers of classes (IIa).
Figure 10:
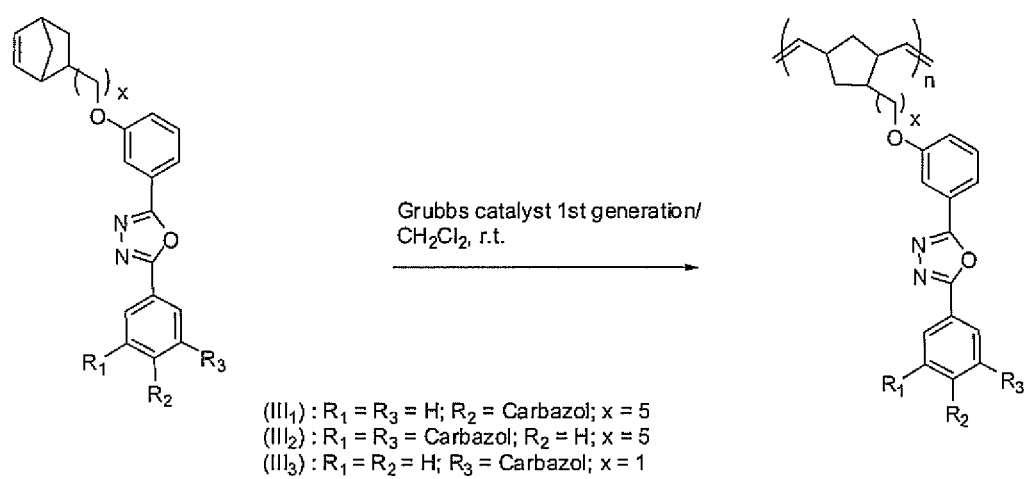
FIG. 10 schematically illustrates the preparation of three ambipolar homopolymers of class (III) as carried out by ROMP initiated polymerizations of norbornenyl based monomers of classes (IIIa). See Example 3.
Figure 11A:
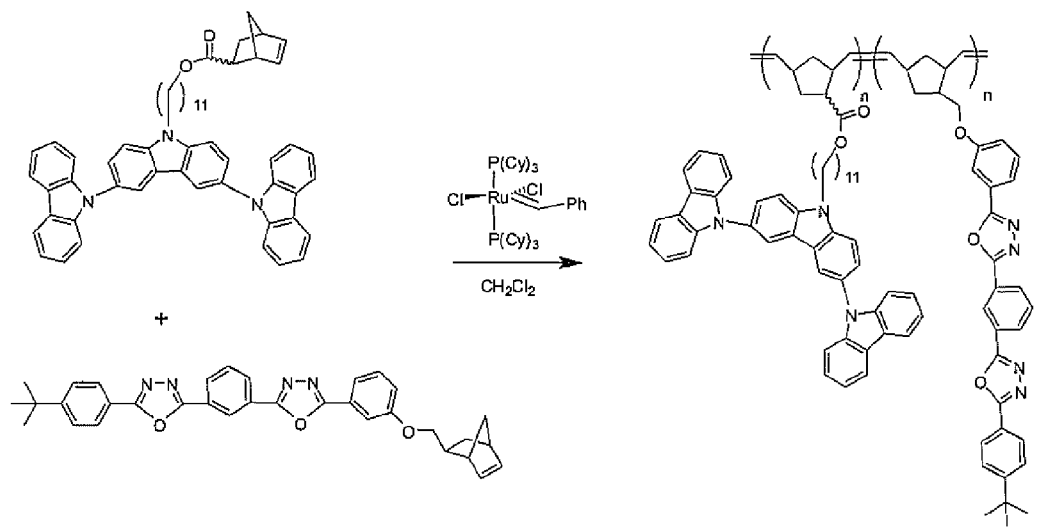
FIG. 11a illustrates a ROMP copolymerization reaction described in Example 4 that produced a copolymer of class (IV).
Figure 11B:
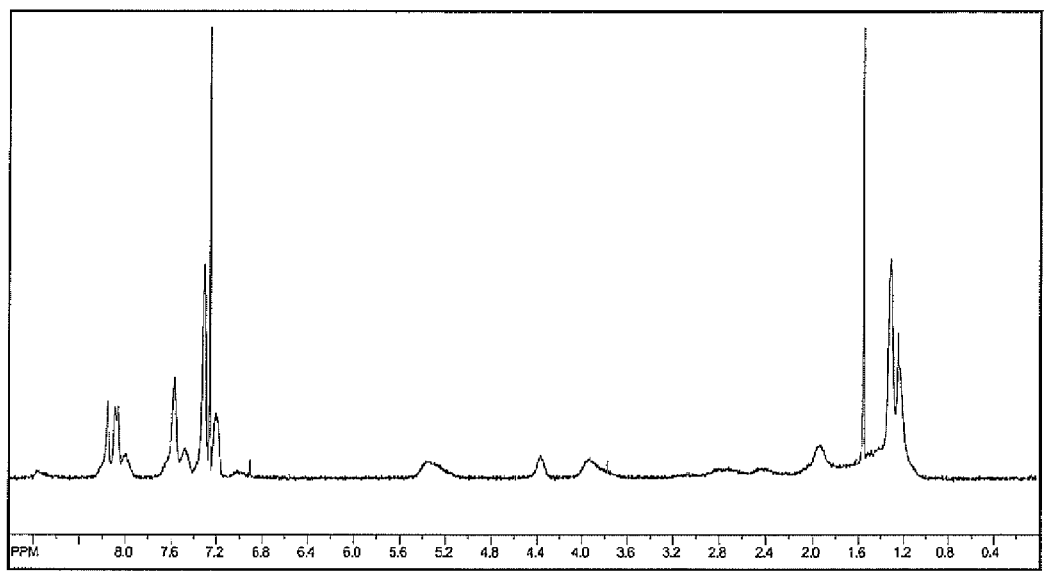
FIG. 11b shows the $^1$H NMR spectrum of the ambipolar copolymer of class (IV) prepared by the copolymerization reaction of FIG. 11a. See Example 4.

Homopolymerization of nine examples of monomers (Ia), (IIa), and (IIIa) were carried out as disclosed in FIGS. 9-11 and exemplified in Example 3. Six homopolymers were prepared by free radical polymerization based on styrene (FIG. 9a) and methacrylate (FIG. 9b) polymerizable ambipolar monomers using AIBN as thermal free radical initiator. Initiator concentrations used for methacrylate is 1.5% (mol ratio) and for styrene is 2.5% in mol ratio. For methacrylate polymerization, high yields (over 90%) could be obtained after 3 day polymerization at 60° C. For styrene polymerization, low yield (46%) was obtained after 3 day polymerization at 60° C. However, polymers were obtained in good yield (over 80%) after 7 day polymerization. All the resulting polymers were purified by multiple dissolution/precipitation. $CH_2Cl_2$/ethanol was used for polymethacrylate and polynorbornene purification and $CH_2Cl_2$/acetone was used for polystyrene purification. All polymers were characterized by $^1$H-NMR, EA and GPC.

Three homopolymers were prepared by ROMP polymerization of three monomers of formula (IIIa) using Grubbs catalyst 1$^{st}$ generation as a catalyst in 1% mol ratio. (See Example 4 and FIG. 10)

It is well known in the art that cyclic olefins, including norbornenes, can be polymerized via ring-opening metathesis polymerization (ROMP), a living polymerization method resulting in polymers with controlled molecular weights, low polydispersities, and which also allows for the easy formation of either random or block co-polymers. See, for example, Fürstner, A. *Angew. Chem., Int. Ed* 2000, 39, 3013; T. M. Trnka, T. M.; Grubbs, R. H. *Acc. Chem. Res.* 2001, 34, 18; *Olefin Metathesis and Metathesis Polymerization,* 2nd Ed.; Ivin, J., Mol, I. C., Eds.; Academic: New York, 1996; and *Handbook of Metathesis, Vol. 3—Application in Polymer Synthesis*; Grubbs, R. H., Ed.; Wiley-VCH: Weinheim, 2003, each of which is respectively incorporated herein by reference for their teachings regarding methods and catalysts for ROMP polymerizations. Catalysts (also termed initiators) commonly used by those skilled in the art include Grubb's ruthenium catalysts (below).

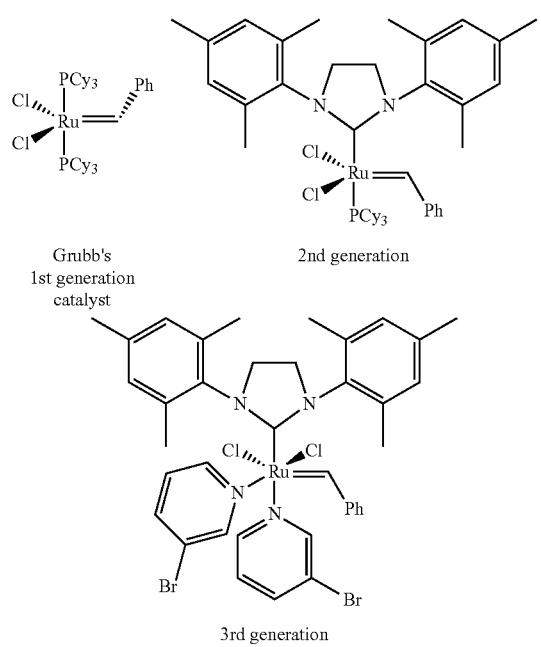

Grubb's 1st generation catalyst

2nd generation

3rd generation

Ruthenium-based ROMP initiators are highly functional-group tolerant, allowing for the polymerization of norbornene monomers linked to fluorescent and phosphorescent metal complexes. ROMP polymerizations can also be carried out with molybdenum or tungsten catalysts such as those described by Schrock (*Olefin Metathesis and Metathesis Polymerization,* 2nd Ed.; Ivin, J., Mol, I. C., Eds.; Academic: New York which is respectively incorporated herein by reference for its teachings regarding molybdenum or tungsten catalysts for ROMP polymerizations).

Copolymerizations of Carbazole and Oxadiazole Monomers to Yield Ambipolar Copolymers of Formula (IV)

Accordingly, in some embodiments the inventions relate to a process for preparing norbornenyl copolymers of class (IV) comprising the steps of
a. mixing
i. at least one first norbornene monomer comprising a norbornene group linked to a carbazole group; and
ii. at least one second norbornene monomer comprising a norbornene group linked to an optionally substituted 2-phenyl-5-phenyl-1,3,4-oxadiazole group; and
iii. optionally one or more additional optionally substituted norbornene monomers; and
b. polymerizing the mixture of norbornene monomers in the presence of a ROMP catalyst, to produce the copolymer.

A norbornenyl monomer linked to a trimeric carbazole group was copolymerized with the norbornenyl monomer linked to an oxadiazole monomer via ring opening metathesis as described in Example 4 below, to form a copolymer of class (IV). The copolymer was synthesized using a 1:1 molar ratio of the monomers. No steps were taken to control the polymer morphology therefore the copolymer was likely random although no information about the reactivity ratios of the monomers was available that would have lead to an expectation of the formation of a copolymer with a morphology other than random. The copolymer was purified by multiple re-precipitations using methanol to obtain. 0.261 g (53.4% isolated yield)) of a light cream colored powder. The $^1$H NMR of the soluble powder in CDCl$_3$ (See FIG. 11) is consistent with the formation of a copolymer of the starting monomers. The copolymer was also successfully characterized by gel permeation chromatography and elemental analysis.

It should also be noted that such copolymerizations can also be carried out the presence of other norbornenyl co-monomers linked to other functional groups, such as cinnamate groups that can used to induce photocrosslinking of the polymers, or phosphorescent "guest" groups such as 3rd row transition metal complexes.

Organic Electronic Devices Comprising the Ambipolar Polymers and Copolymers

Some aspects of the present inventions relate to novel organic electronic devices, including light emitting diodes and OLED devices that comprise the various ambipolar compounds, homopolymers, copolymers described above. As further described below, the various ambipolar compounds, homopolymers, copolymers are readily soluble in common organic solvents and can be mixed with compounds that can serve as guest phosphorescent emitters, and the mixture solution processed and/or spin coated onto appropriate substrates to form the emission layer of an OLED device.

In some embodiments, light emitting diodes and/or OLED devices comprise an anode layer, a hole transporting layer, an emission layer, an electron transporting layer, and a cathode layer.

Accordingly, in many embodiments of the OLED devices disclosed herein, the OLEDs comprise the following layers:
a. an anode layer,
b. a hole transporting layer,
c. an emissive layer,
d. an electron transporting layer, and
e. a cathode layer.

In many embodiments of the OLED devices disclosed herein, the emissive layer comprises at least some of the compound.

Indium tin oxide (ITO) is an example of a suitable material for the anode layers, and is often applied by vacuum deposition in a layer over an inert and transparent substrate such as glass.

Many materials are potentially useful as hole transporting layers, including monomeric or polymeric carbazole compounds such as polyvinyl carbazole (PVK). Poly-TPD-F (structure shown below, see Zhang, et al., *Synthesis* 2002, 1201 and Domercq, et al., *Chem. Mater.* 2003, 15, 1491, both of which are incorporated herein by reference in their entirety) is especially useful because it is photo cross-linkable and can be used to produce photo-patterned hole transporting layers.

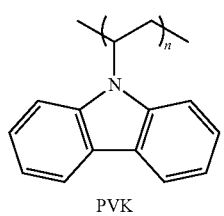

PVK

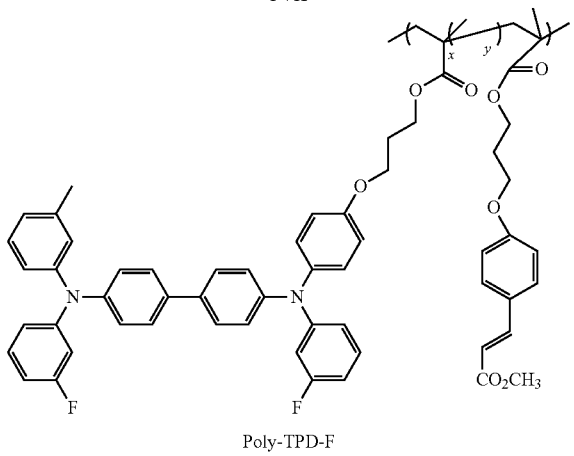

Poly-TPD-F

Many materials are suitable as electron transporting and/or hole blocking materials, such as bathocuproine (BCP=2,9-dimethyl-4,7-diphenyl-1,10-phenanthroline, BCP, or structure shown below) which can be readily applied to the devices via vacuum/thermal deposition techniques.

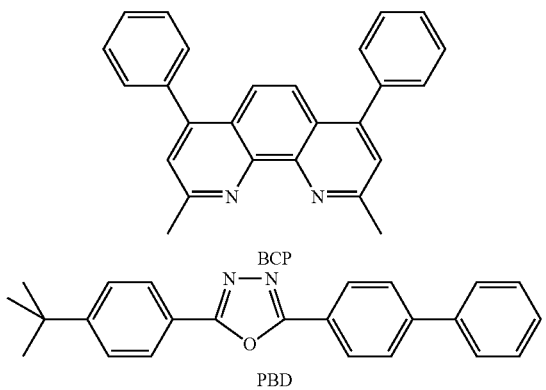

BCP

PBD

Many materials can be suitable as cathode layers, one example being a combination of lithium fluoride (LIE) as an electron injecting material coated with a vacuum deposited layer of Aluminum.

As already previously noted above, the ambipolar polymers or copolymers of the current inventions can transport both holes and electrons, and therefore function as an efficient host for phosphorescent guests, such as well known Iridium complexes such as Ir(ppy) (ppy=2-phenylpyridine) and Platinum complexes exemplified below.

It is also worth noting that the ambipolar polymers or copolymers of the current inventions can transport both holes and electrons, and therefore can also potentially be used as a substitute for the hole transporting material in the hole transporting layer, or the electron transporting material of the electron transporting layer. When the emission layer of the device comprises the ambipolar polymers or copolymers of the current inventions, it is also possible to simply omit the hole or electron transporting layers.

Electroluminescent Properties of the OLED Devices

A number of exemplary OLED devices comprising the ambipolar polymers or copolymers of the current inventions as guests for Platinum and Iridium complexes as phosphorescent guests are described in the Examples below, which describe the particular photoluminescence properties measured for those exemplary devices. See Examples 5 and 6, and FIGS. 12-16. In most examples, same device structure was fabricated from different host polymers (as shown in FIG. 5).

EXAMPLES

The various inventions described above are further illustrated by the following specific examples, which are not intended to be construed in any way as imposing limitations upon the scope of the invention disclosures or claims attached herewith. On the contrary, it is to be clearly understood that resort may be had to various other embodiments, modifications, and equivalents thereof which, after reading the description herein, may suggest themselves to one of ordinary skill in the art without departing from the spirit of the present invention or the scope of the appended claims.

General—All experiments with air- and moisture-sensitive intermediates and compounds were carried out under an inert atmosphere using standard Schlenk techniques. NMR spectra were recorded on either a 400 MHz Varian Mercury spectrometer or a 400 MHz Bruker AMX 400 and referenced to residual proton solvent. UV-vis absorption spectra were recorded on a Varian Cary 5E UV-vis-NIR spectrophotometer, while solution and thin-film PL spectra were recorded on a Fluorolog III ISA spectrofluorimeter. Lifetime measurements were taken using a PTI model C-72 fluorescence laser spectrophotometer with a PTI GL-3300 nitrogen laser. Cyclic voltammograms were obtained on a computer controlled BAS 100B electrochemical analyzer, and measurements were carried out under a nitrogen flow in deoxygenated DMF solutions of tetra-n-butylammonium hexafluorophosphate (0.1M). Glassy carbon was used as the working electrode, a Pt wire as the counter electrode, and an Ag wire anodized with AgCl as the pseudo-reference electrode. Potentials were referenced to the ferrocenium/ferrocene ($FeCp_2^{+/0}$) couple by using ferrocene as an internal standard. Gel-permeation chromatography (GPC) analyses were carried out using a Waters 1525 binary pump coupled to a Waters 2414 refractive index detector with methylene chloride as an eluent on American Polymer Standards 10 μm particle size, linear mixed bed packing columns. The flow rate used for all measurements was 1 ml/min, and the GPCs were calibrated using poly (styrene) standards. Differential scanning calorimetry (DSC) data were collected using a Seiko model DSC 220C. Thermal gravimetric analysis (TGA) data were collected using a Seiko model TG/DTA 320. Inductively coupled plasma-mass spectrometry (ICP-MS) for platinum and ruthenium was provided by Bodycote Testing Group. $^1$H-NMR and $^{13}$C-NMR spectra (300 MHz $^1$H NMR, 75 MHz $^{13}$C NMR) were obtained using a Varian Mercury Vx 300 spectrometer. All spectra are referenced to residual proton solvent. Abbreviations used include singlet (s), doublet (d), doublet of doublets (dd), triplet (t), triplet of doublets (td) and unresolved multiplet (m). Mass spectral analyses were provided by the Georgia Tech Mass Spectrometry Facility. The onset of thermal degradation for the polymers was measured by thermal gravimetric analysis (TGA) using a Shimadzu TGA-50. UV/vis absorption measurements were taken on a Shimadzu UV-2401 PC recording spectrophotometer. Emission measurements were acquired using a Shimadzu RF-5301 PC spectrofluorophotometer. Lifetime measurements were taken using a PTI model C-72 fluorescence laser spectrophotometer with a PTI GL-3300 nitrogen laser. Elemental analyses for C, H, and N were performed using Perkin Elmer Series II CHNS/O Analyzer 2400. Elemental analyses for iridium were provided by Galbraith Laboratories.

Unless otherwise noted, cited reagents and solvents were purchased from well-known commercial sources (such as Sigma-Aldrich of Milwaukee Wis. or Acros Organics of Geel Belgium, and were used as received without further purification.

Example 1 Synthesis of Precursors of Ambipolar Monomers

Figure 3:
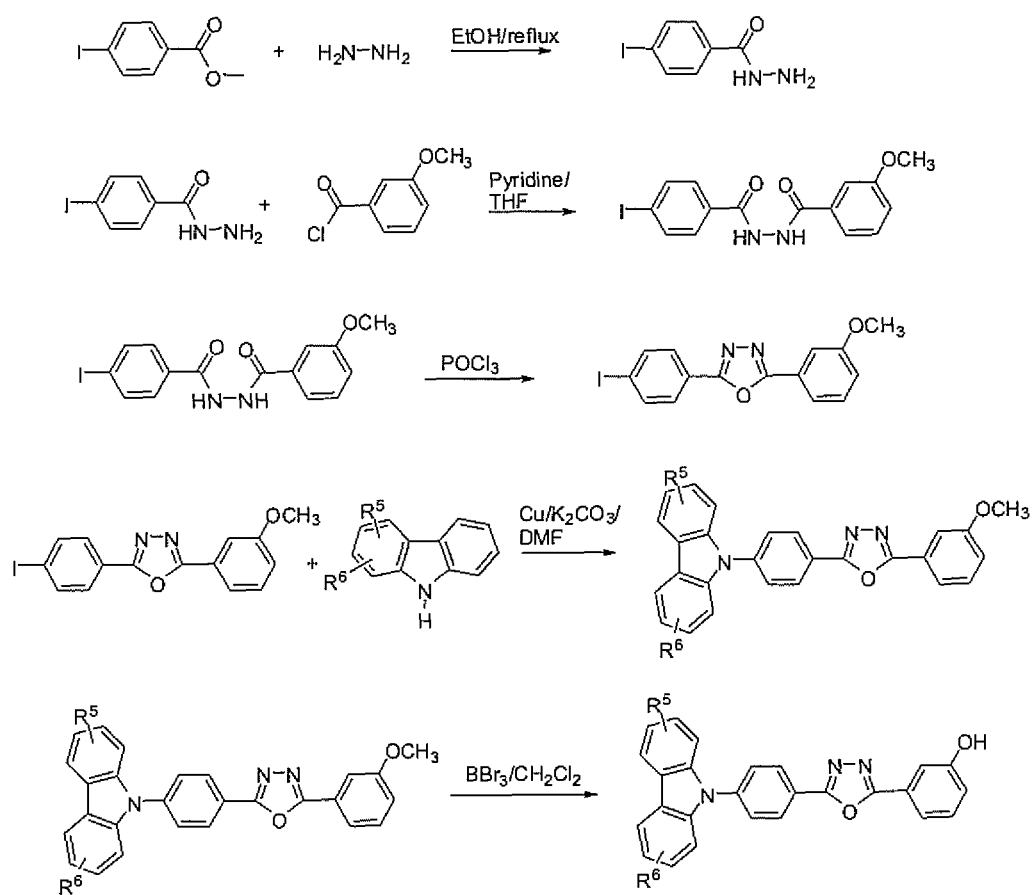
FIG. 3 discloses a generic scheme for the synthesis of certain "linear" isomers of ambipolar compounds comprising both one carbazole and one oxadiazole group, which can serve as synthetic precursors of ambipolar monomers, as further described elsewhere herein and specifically exemplified in Example 1.
Figure 4:
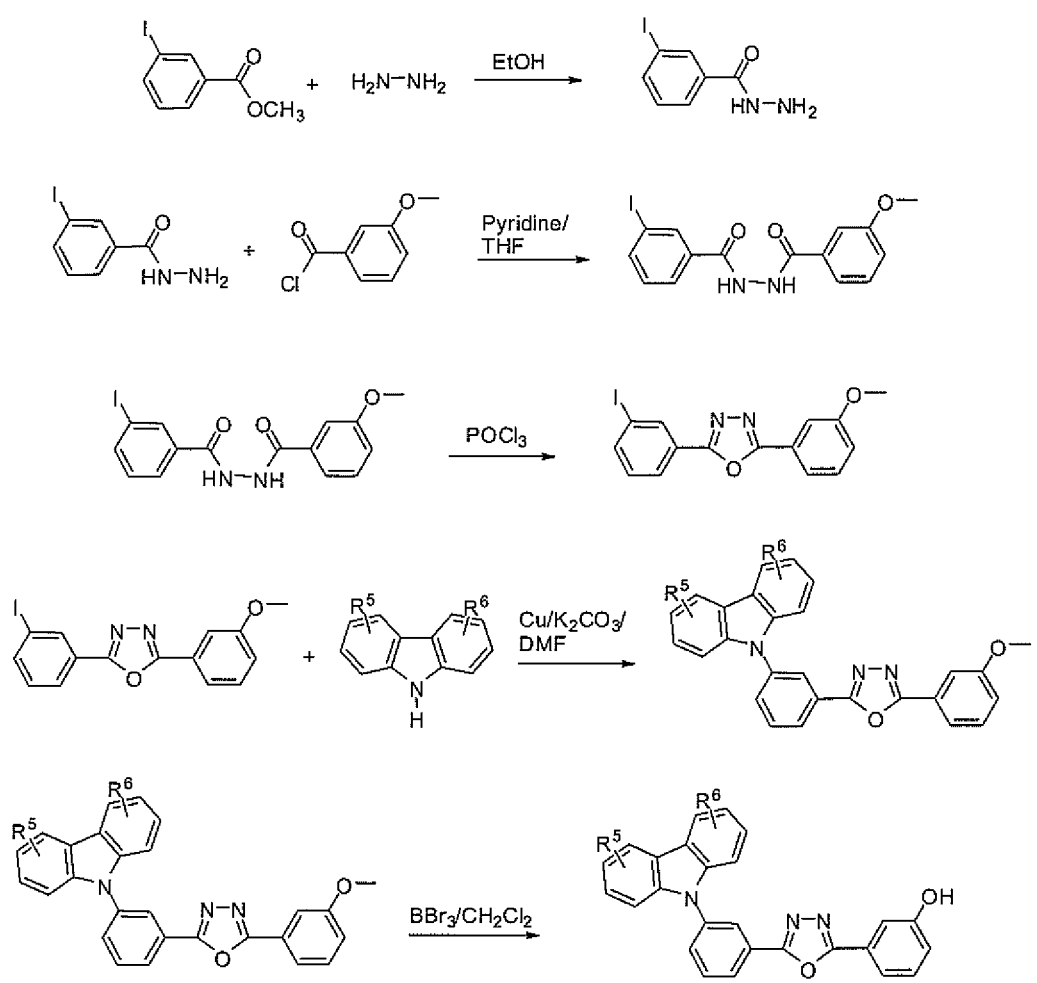
FIG. 4 discloses a generic scheme for the synthesis of certain "non-linear" isomers of ambipolar compounds comprising both one carbazole and one oxadiazole group, which can serve as synthetic precursors of ambipolar monomers, as further described elsewhere herein and specifically exemplified in Example 1.
Figure 5:
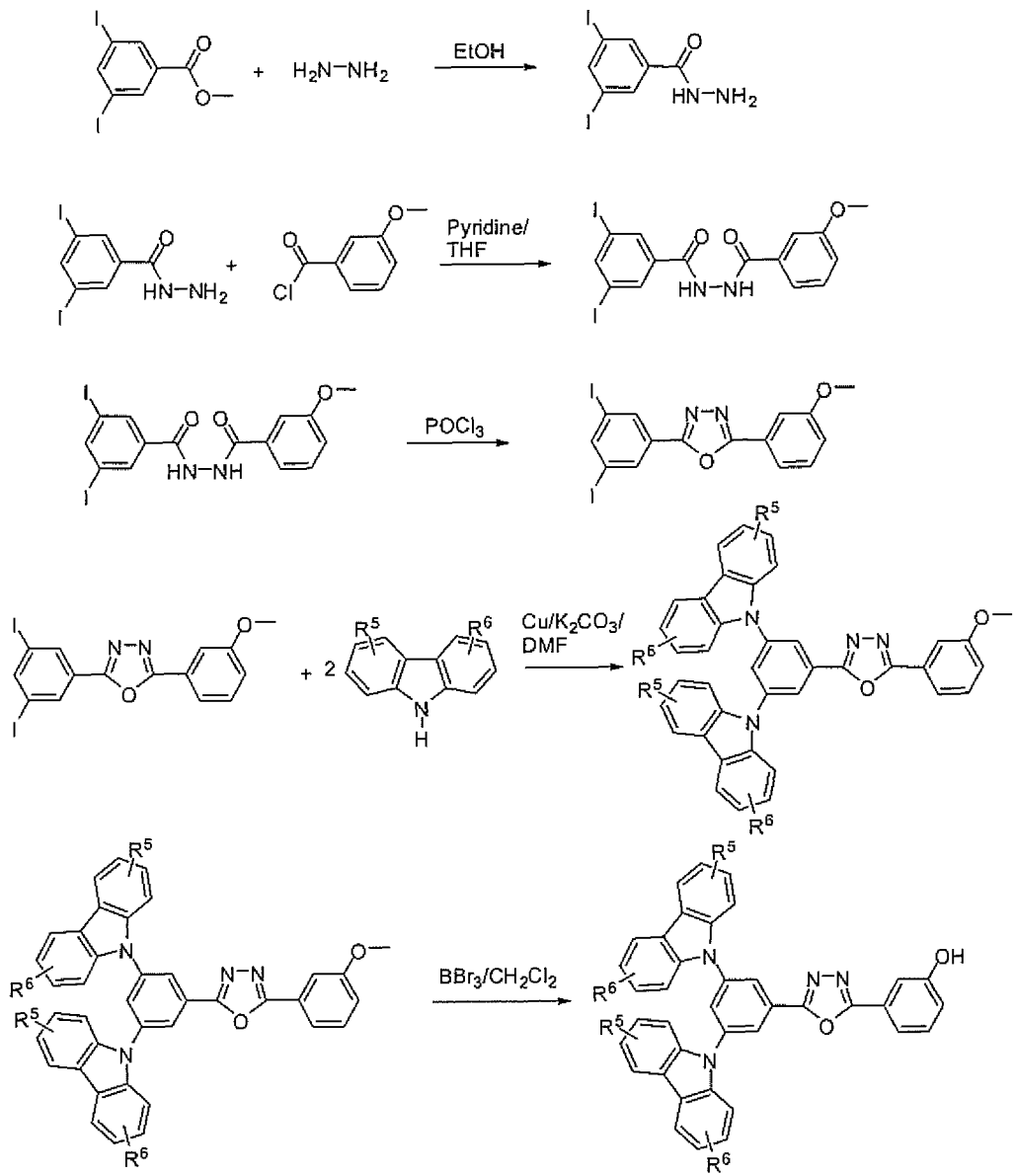
FIG. 5 discloses a generic scheme for the synthesis of ambipolar compounds comprising both two carbazole and one oxadiazole groups, which can serve as synthetic precursors of ambipolar monomers, as further described elsewhere herein and specifically exemplified in Example 1.

See FIGS. 3-5

Synthesis of 4-Iodobenzohydrazide

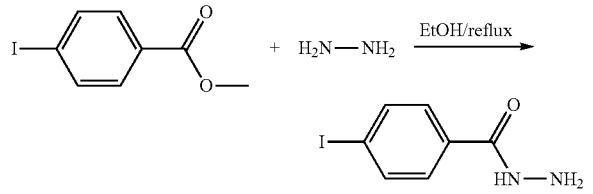

To Methyl 4-iodobenzoate (30.0 g, 114 mmol) in ethanol (180.0 ml) was added hydrazine hydrate (30.0 g, 599 mmol). The reaction mixture was reflux for 22.5 hours. Heating was stopped and then water (300.0 ml) was added. After cooling down to room temperature, white solid was appeared. The white product solid was collected by filtration. The product was washed with water and dried under vacuum. Final white pure product was obtained in 26.0 g (86.7%). $^1$H NMR (400 MHz, DMSO-$d_6$, δ): 9.84 (s, 1H, NH), 7.82 (d, J=8.4 Hz, 2H), 7.59 (d, J=8.4 Hz, 2H), 4.50 (s, 2H, NH$_2$).

Synthesis of N'-(4-iodobenzoyl)-3-methoxy benzohydrazide

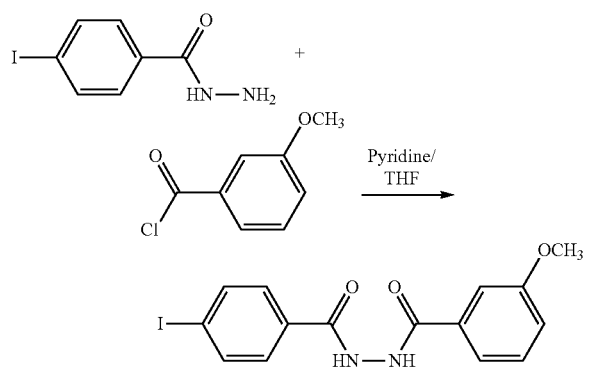

To a solution of 4-Iodobenzohydrazide (5.0 g, 19.1 mmol) in dry THF (80.0 ml) was slowly added 3-methoxybenzoyl chloride (3.5 g, 20.5 mmol) at 0° C. under nitrogen. During addition of 3-methoxybenzoyl chloride the white solid was appeared. After addition of 3-methoxybenzoyl chloride, the reaction was warmed up to room temperature. The reaction mixture was stirred for 18 hours at room temperature and then pyridine (5.0 ml) was added and stirred for additional 2 h. Water (300.0 ml) was added to reaction mixture. The white solid was obtained and collected by filtration. After dried under vacuum, product was obtained as white powder in 7.2 g (94.7%). $^1$H NMR (400 MHz, DMSO-$d_6$, δ): 10.60 (s, 1H, NH), 10.52 (s, 1H, NH), 7.91 (d, J=8.0 Hz, 2H), 7.68 (d, J=8.0 Hz, 2H), 7.50 (d, J=8.0 Hz, 1H), 7.45 (d, J=2.4 Hz, 1H), 7.41 (d, J=8.0 Hz, 1H), 7.15 (dd, $J_1$=8.0 Hz, $J_2$=2.4 Hz, 1H), 3.81 (s, 3H, OCH$_3$).

Synthesis of 2-(4-Iodophenyl)-5-(3-methoxyphenyl)-1,3,4-oxadiazole

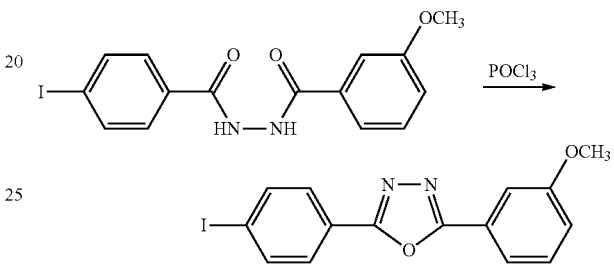

N'-(4-iodobenzoyl)-3-methoxybenzohydrazide (7.0 g, 17.67 mmol) was suspended in POCl$_3$ (40.0 ml) and heating was started. The reaction was kept at 100° C. During heating white solid of starting materials dissolved into a clear solution and the reaction was monitor by thin layer chromatography. After 1 h, the reaction mixture was brought to room temperature and was carefully dropped into ice-water (500.0 ml). White solid precipitated out was collected by filtration and washed with water. After dry, the crude product was purified by silica gel column chromatography eluting with dichloromethane and ethyl acetate in 25:1 ratio. After evaporating solvent the white solid was recrystallized from acetone/water and finally dried under vacuum. Pure product was obtained as white solid in 5.8 g (86.8%) yield. $^1$H NMR (400 MHz, CDCl$_3$, δ): 7.86 (d, J=8.4 Hz, 2H), 7.83 (d, J=8.4 Hz, 2H), 7.67 (dt, $J_1$=8.0 Hz, $J_2$=1.2 Hz, 1H), 7.63 (m, 1H), 7.42 (t, J=8 Hz, 1H), 7.07 (m, 1H), 3.88 (s, 3H, OCH$_3$). $^{13}$C NMR (100 MHz, CDCl$_3$, δ): 164.66, 164.00, 159.92, 138.32, 130.23, 128.21, 124.73, 123.26, 119.29, 118.26, 111.56, 98.60, 55.52.

Synthesis of 2-(4-Carbazol-9-ylphenyl)-5-(3-methoxyphenyl)-1,3,4-oxadiazole

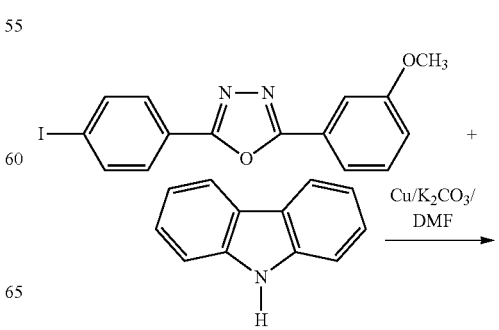

-continued

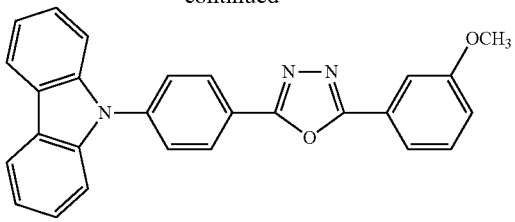

To a solution of 2-(4-iodophenyl)-5-(3-methoxyphenyl)-1,3,4-oxadiazole (3.0 g, 7.93 mmol), carbazole (1.5 g, 8.97 mmol), Cu (2.0 g, 31.47 mmol) in DMF (20.0 ml) was added potassium carbonate (4.0 g, 28.94 mmol) under nitrogen and stirring. Heating was started. The reaction was carried out at 150° C. for 4 h. After cooling, the reaction mixture was filtrated. The solid residues were carefully washed with THF. THF was evaporated from the combined filtration solution, Water (200.0 ml) was added, the yellow solid product was obtained by filtration. The crude product was purified by silica gel column chromatography using dichloromethane/ethyl acetate (9.5:0.5) as eluent. After evaporating solvent, the white solid was recrystallized from acetone/water and finally dried under vacuum. Pure product was obtained as white solid in 3.2 g (96.7%) yield. $^1$H NMR (400 MHz, CDCl$_3$, δ): 8.38 (m, 2H), 8.16 (d, J=8.0 Hz, 2 Hz), 7.81-7.72 (m, 4H), 7.52-7.43 (m, 5H), 7.33 (m, 2H), 7.12 (m, 1H). $^{13}$C NMR (100 MHz, CDCl$_3$, δ): 164.72, 164.02, 159.99, 140.90, 140.21, 130.28, 128.58, 127.21, 126.21, 124.88, 123.76, 122.40, 120.57, 120.48, 119.33, 118.29, 111.61, 109.68, 94.23, 55.55. [M]$^+$ calcd for C$_{27}$H$_{19}$N$_3$O$_2$, 417.2. found 417.1.

Synthesis of 3-(5-(4-carbazol-9-ylphenyl)-1,3,4-oxadiazol-2-yl)phenol

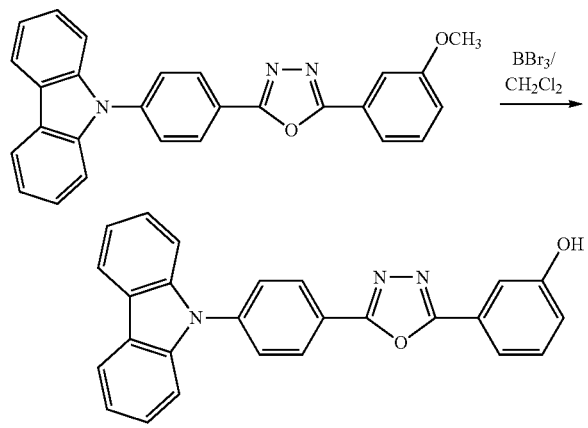

To a solution of 2-(4-carbazol-9-ylphenyl)-5-(3-methoxyphenyl)-1,3,4-oxadiazole (1.0 g, 2.40 mmol) in dichloromethane (10.0 ml) was dropwise added BBr$_3$ (10.0 ml, 1M in dichloromethane) at −78° C. (dry-ice/acetone) under nitrogen. After addition of BBr$_3$ solution, the reaction was taken to room temperature and kept at room temperature for 5 h. The reaction mixture was poured into ice-water (50.0 ml). Dichloromethane was evaporated under reduced pressure. The white solid was collected by filtration. After drying under vacuum, product as white solid was obtained in 0.97 g (100%) yield. $^1$H NMR (400 MHz, acetone-d$_6$, δ): 8.91 (s, 1H, OH), 8.48 (m, 2H), 8.24 (dt, J$_1$=8.0 Hz, J$_2$=1.2 Hz, 2H), 7.91 (m, 2H), 7.71 (t, J=1.2 Hz, 1H), 7.69 (t, J=1.6 Hz, 1H), 7.56 (d, J=0.8 Hz, 1H), 7.54 (t, J=0.8 Hz, 1H), 7.46 (m, 3H), 7.32 (m, 2H), 7.12 (m, 1H), 3.93 (s, 3H, OCH$_3$). $^{13}$C NMR (100 MHz, acetone-d$_6$, δ): 165.43, 164.72, 158.87, 141.48, 141.12, 131.44, 129.41, 128.23, 127.17, 126.04, 124.56, 123.65, 121.43, 121.26, 119.88, 118.89, 114.18, 110.62. MS-EI (m/z): [M]$^+$ calcd for C$_{26}$H$_{17}$N$_3$O$_2$, 403.1. found 403.1.

Synthesis of Methyl 3-iodobenzoate

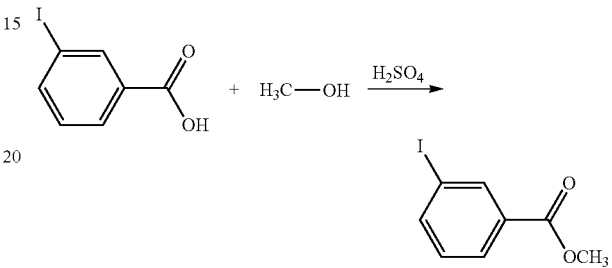

To a solution of 3-iodobenzoic acid (50.0 g, 0.202 mol) in methanol (300.0 ml) was added H$_2$SO$_4$ (1.0 ml). The reaction mixture was heated to reflux. After reflux 24 h, heating was stopped. The reaction mixture was cooled to room temperature. Water (400.0 ml) was added, the product was extracted with ethyl acetate (2×300.0 ml). The organic layer was washed with 20% of NaHCO$_3$ water solution and followed with water. After removal of ethyl acetate, the crude product was purified by recrystallization from ethanol/water. Final white pure product was obtained in 51.0 g (96.5%) after dry under vacuum. $^1$H NMR (400 MHz, CDCl$_3$, δ): 8.35 (t, J=1.6 Hz, 1H), 7.97 (dt, J$_1$=8.4 Hz, J$_2$=1.6 Hz, 1H), 7.85 (dt, J$_1$=8.4 Hz, J$_2$=1.6 Hz, 1H), 7.14 (t, J=8.4 Hz, 1H), 3.89 (s, 3H, OCH$_3$). $^{13}$C NMR (100 MHz, CDCl$_3$, δ): 165.56, 141.70, 138.42, 131.93, 130.03, 128.70, 93.76, 52.38.

Synthesis of 3-Iodobenzohydrazide

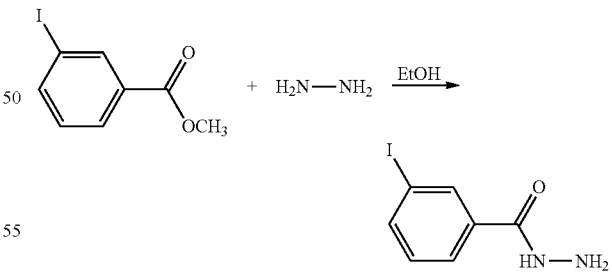

To Methyl 3-iodobenzoate (25.0 g, 95.41 mmol) in ethanol (120.0 ml) was added hydrazine hydrate (50.0 ml). The reaction mixture was reflux for 18 hours. Heating was stopped and then water (300.0 ml) was added. After cooling down to room temperature, white solid was appeared. The white product solid was collected by filtration. The product was washed with water and dried under vacuum. Final white pure product was obtained in 23.0 g (92.0%). $^1$H NMR (400 MHz, DMSO-d$_6$, δ): 9.85 (s, br, 1H, NH), 8.14 (t, J=1.6 Hz, 1H), 7.85 (m, 1H), 7.82 (m, 1H), 7.25 (t, J=8.0 Hz, 1H), 4.50 (s, 2H, NH$_2$). $^{13}$C NMR (100 MHz, CDCl$_3$) δ: 168.54, 155.38, 129.54, 126.72, 125.57, 34.90, 31.07.

Synthesis of 3-Iodo-N'-(3-methoxybenzoyl)benzohydrazide

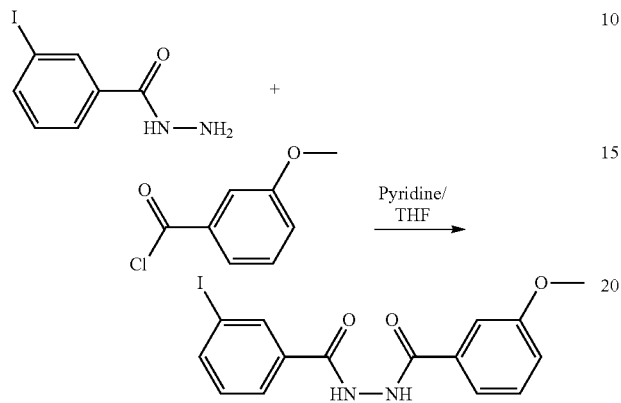

To a solution of 3-iodobenzohydrazide (10.0 g, 38.16 mmol) in dry THF/DMF (100.0 ml:10.0 ml) was slowly added 3-methoxybenzoyl chloride (7.0 g, 42.03 mmol) at 0° C. under nitrogen. During addition of 3-methoxybenzoyl chloride, white solid was appeared. After addition of 3-methoxybenzoyl chloride, the reaction was allowed to warm up to room temperature. The reaction mixture was stirred for 19 hours at room temperature and then pyridine (20.0 ml) was added and stirred for additional 45 min. Water (300.0 ml) was added to reaction mixture. The white solid was obtained and collected by filtration and washed with water. After dried under vacuum, product was obtained as white powder in 12.4 g (82.0%). $^1$H NMR (400 MHz, DMSO-d$_6$, δ): 10.62 (s, 1H, NH), 10.56 (s, 1H, NH), 8.25 (t, J=1.6 Hz, 1H), 7.96 (d, J=8.0 Hz, 1H), 7.91 (d, J=8.0 Hz, 1H), 7.49 (d, J=8.0 Hz, 1H), 7.45 (d, J=2.4 Hz, 1H), 7.41 (d, J=8.0 Hz, 1H), 7.34 (t, J=8.0 Hz, 1H), (dd, J$_1$=8.0 Hz, J$_2$=2.4 Hz, 1H), 3.81 (s, 3H, OCH$_3$).

Synthesis of 2-(3-Iodophenyl)-5-(3-methoxyphenyl)-1,3,4-oxadiazole

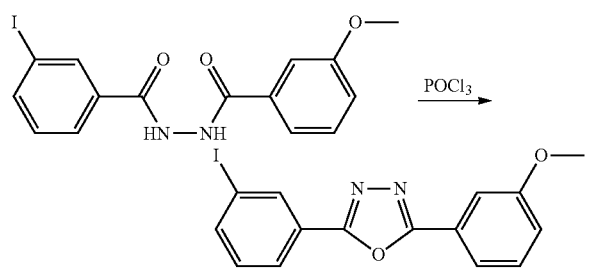

3-Iodo-N'-(3-methoxybenzoyl)benzohydrazide (11.0 g, 27.77 mmol) was suspended in POCl$_3$ (60.0 ml) and heating was started. During heating white solid of starting materials dissolved into a clear solution. The reaction was kept at 100° C. and the reaction was monitor by thin layer chromatography. After 2 h, the reaction mixture was brought to room temperature and was carefully dropped into ice-water (1000.0 ml). White solid precipitated out was collected by filtration and washed with water. After dried, the crude product was purified by silica gel column chromatography eluting with dichloromethane and ethyl acetate in 9.5:0.5 ratio. After evaporating solvent the white solid was recrystallized from acetone/water and finally dried under vacuum. Pure product was obtained as white solid in 6.4 g (61.0%) yield. $^1$H NMR (400 MHz, CDCl$_3$, δ): 8.47 (t, J=1.6 Hz, 2H), 8.12 (dt, J$_1$=8.0 Hz, J$_2$=1.6 Hz, 1H), 7.88 (m, 1H), 7.70 (dt, J$_1$=8.0 Hz, J$_2$=1.6 Hz, 1H), 7.67 (m, 1H), 7.45 (t, J=8.0 Hz, 1H), 7.28 (t, J=8.0 Hz, 1H), 7.10 (m, 1H), 3.92 (s, 3H, OCH$_3$). $^{33}$C NMR (100 MHz, CDCl$_3$, δ): 164.79, 163.07, 159.94, 140.58, 135.46, 130.68, 130.26, 126.03, 125.68, 124.69, 119.36, 118.36, 111.59, 94.39, 55.56.

Synthesis of 2-(3-Carbazol-9-ylphenyl)-5-(3-methoxyphenyl)-1,3,4-oxadiazole

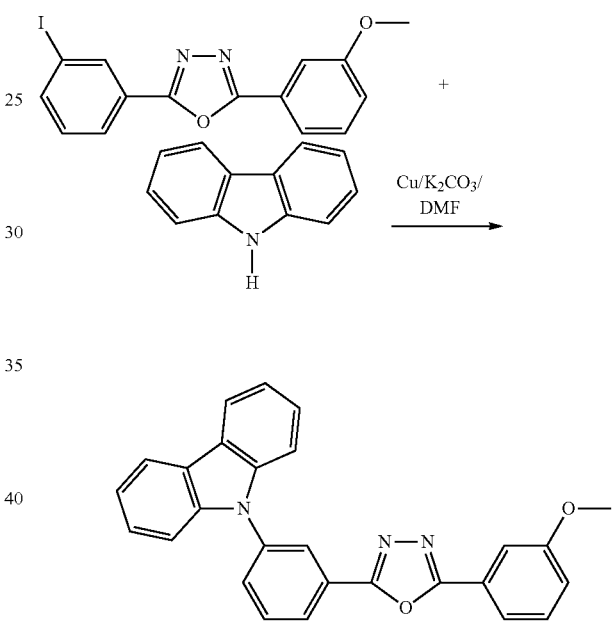

To a solution of 2-(3-iodophenyl)-5-(3-methoxyphenyl)-1,3,4-oxadiazole (3.0 g, 7.93 mmol), carbazole (1.5 g, 8.97 mmol), Cu (2.0 g, 31.47 mmol) in DMF (20.0 ml) was added potassium carbonate (4.0 g, 28.94 mmol) under nitrogen and stirring. Heating was started. The reaction was carried out at 150° C. for 5 h. After cooling, the reaction mixture was filtrated. The solid residues were carefully washed with THF. THF was evaporated from the combined filtration solution. Water (150.0 ml) was added, the brown solid product was obtained by filtration. The crude product was purified by silica gel column chromatography using dichloromethane/ethyl acetate (9.5:0.5) as eluent. After evaporating solvent, the white solid was recrystallized from acetone/methanol and finally dried under vacuum. Pure product was obtained as white solid in 3.15 g (95.4%) yield. $^1$H NMR (400 MHz, CDCl$_3$, δ): 8.34 (m, 1H), 8.27 (m, 1 Hz), 8.18 (m, 2H), 7.78 (m, 2H), 7.71-7.65 (m, 2H), 7.46-7.41 (m, 5H), 7.36-7.31 (m, 2H), 7.09 (m, 1H), 3.89 (s, 3H, OCH$_3$). $^{13}$C NMR (100 MHz, CDCl$_3$, δ): 164.85, 163.84, 159.96, 140.60, 138.70, 130.85, 130.32, 130.25, 126.19, 125.84, 125.40, 124.72, 123.55, 120.45, 120.37, 119.39, 118.44, 111.52, 109.55, 55.55. [M]+ calcd for C39H26N4O2, 417.2. found 417.1.

Synthesis of 3-(5-(3-carbazol-9-ylphenyl)-1,3,4-oxadiazol-2-yl)phenol

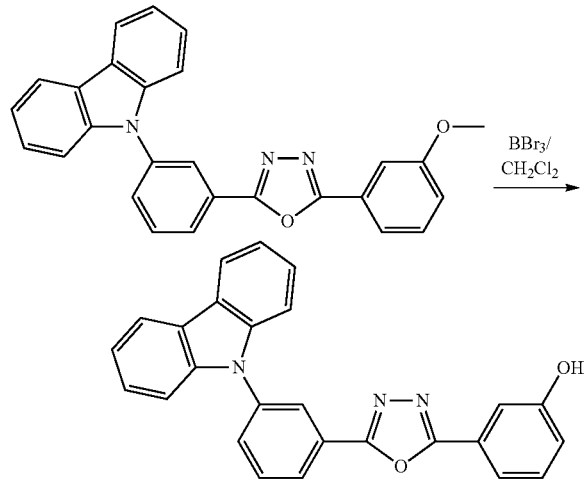

To a solution of 2-(3-carbazol-9-ylphenyl)-5-(3-methoxyphenyl)-1,3,4-oxadiazole (3.0 g, 72 mmol) in dichloromethane (20.0 ml) was dropwise added BBr₃ (30.0 ml, 1M in dichloromethane) at −78° C. (dry-ice/acetone) under nitrogen. After addition of BBr₃ solution, the reaction was taken to room temperature and kept at room temperature for 6 h. The reaction mixture was poured into ice-water (100.0 ml). Dichloromethane was evaporated under reduced pressure. The white solid was collected by filtration. After drying under vacuum, product as white solid was obtained in 2.9 g (100%) yield. $^1$H NMR (400 MHz, acetone-d$_6$, δ): 8.89 (s, br, 1H, OH), 8.41 (m, 1H), 8.34 (m, 1H), 8.26 (m, 2H), 7.92 (m, 2H), 7.66 (m, 2H), 7.53-7.41 (m, 5H), 7.33 (m, 2H), 7.10 (m, 1H). MS-EI (m/z): [M]+ calcd for C₂₆H₁₇N₃O₂, 403.1. found 403.1.

Synthesis of 3,5-Diiodobenzohydrazide

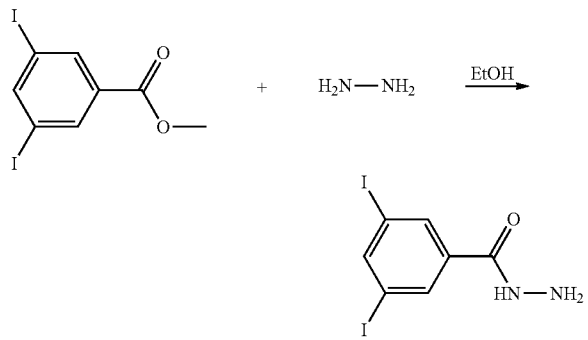

To Methyl 3,5-diiodobenzoate (5.0 g, 12.89 mmol) in ethanol (70.0 ml) was added hydrazine hydrate (20.0 ml) under stirring. During heating, white solid was appeared. The reaction was kept 50° C. for 1 h. Heating was stopped and then water (100.0 ml) was added. After cooling down to room temperature, the white product solid was collected by filtration. The product was washed with water and dried under vacuum. Final white product was obtained in 4.6 g (92.0%). $^1$H NMR (400 MHz, DMSO-d$_6$, δ): 9.92 (s, 1H, NH), 8.22 (t, J=1.6 Hz, 1H), 8.12 (d, J=1.6 Hz, 2H), 4.53 (s, 2H, NH₂).

3,5-diiodo-N'-(3-methoxybenzoyl)benzohydrazide

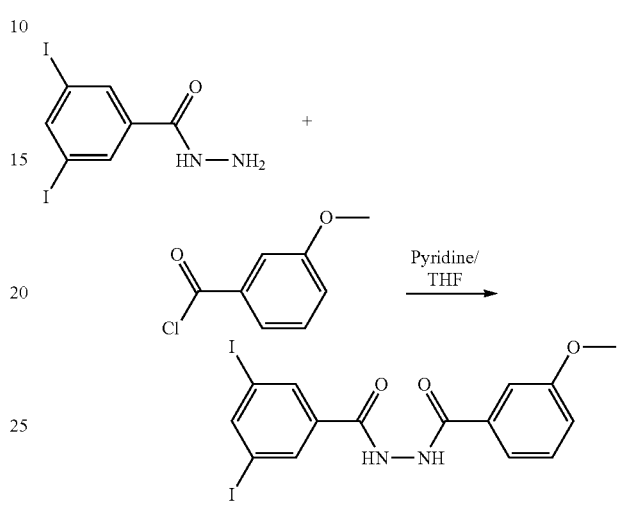

To a solution of 3,5-Diiodobenzohydrazide (4.5 g, 11.60 mmol) in dry THF/DMF (100.0 ml:24.0 ml) was slowly added 3-methoxybenzoyl chloride (2.2 g, 12.90 mmol) at 0° C. under nitrogen. After addition of 3-methoxybenzoyl chloride, the reaction was warmed up to room temperature. The reaction mixture was stirred for 19 hours at room temperature and then pyridine (5.0 ml) was added and stirred for additional 1 h. Water (300.0 ml) was added to reaction mixture. The white solid was obtained and collected by filtration. After dried under vacuum, product was obtained as white powder in 5.05 g (83.3%). $^1$H NMR (400 MHz, DMSO-d$_6$, δ): 10.72 (s, 1H, NH), 10.62 (s, br, 1H, NH), 8.33 (t, J=1.6 Hz, 1H), 8.23 (d, J=1.6 Hz, 2H), 7.50-7.41 (m, 3H), 7.15 (m, 1H), 3.81 (s, 3H, OCH₃).

Synthesis of 2-(3,5-Diiodophenyl)-5-(3-methoxyphenyl)-1,3,4-oxadiazole 3,5-Diiodo-N'-(3-methoxybenzoyl)benzohydrazide (5.0 g, 9.58 mmol) was suspended in POCl₃ (50.0 ml) and heating was started. During heating white solid of starting materials dissolved into a clear solution (130° C.). The reaction was kept at 100° C. and the reaction was monitor by thin layer chromatography. After 5 h, the reaction mixture was brought to room temperature and was carefully dropped into ice-water (1000.0 ml). White solid precipitated out was collected by filtration and washed with water. After dried, the crude product was purified by silica gel column chromatography eluting with dichloromethane and ethyl acetate in 9.5:0.5 ratio. After evaporating solvent the white solid was recrystallized from acetone/water and finally dried under vacuum. Pure product was obtained as white solid in 3.4 g (70.8%) yield. $^1$H NMR (400 MHz, CDCl$_3$, δ): 8.43 (dd, J$_1$=1.6 Hz, J$_2$=0.8 Hz, 2H), 8.23 (t, J=1.6 Hz, 1H), 7.71 (d, J=8.0 Hz, 1H), 7.66 (m, 1H), 7.46 (t, J=8.0 Hz, 1H), 7.12 (dd, J$_1$=8.0 Hz, J$_2$=2.4 Hz, 1H), 3.92 (s, 3H, OCH$_3$). $^{13}$C NMR (100 MHz, CDCl$_3$, δ): 165.06, 161.67, 159.98, 148.05, 134.63, 130.31, 126.95, 124.44, 119.44, 118.56, 111.66, 94.98, 55.59.

Synthesis of 2-(3,5-Dicarbazol-9-ylphenyl)-5-(3-methoxyphenyl)-1,3,4-oxadiazole

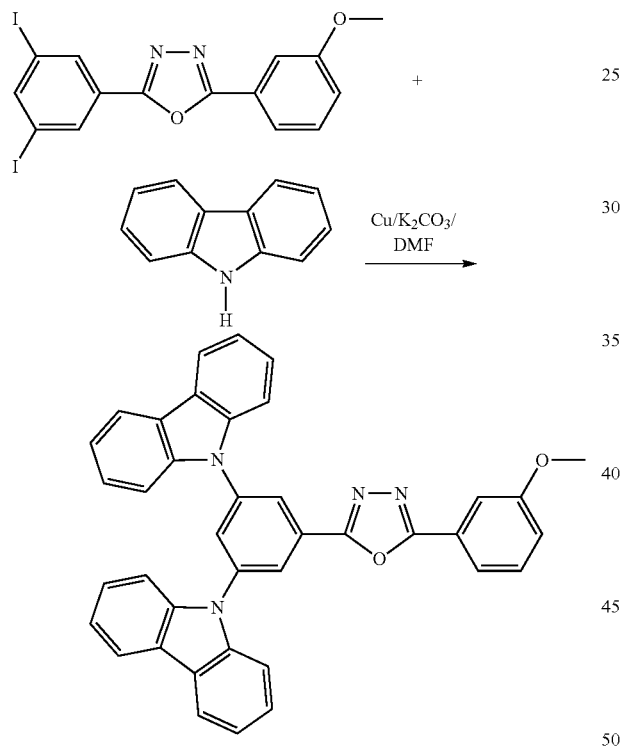

To a solution of 2-(3,5-diiodophenyl)-5-(3-methoxyphenyl)-1,3,4-oxadiazole (1.0 g, 1.98 mmol), carbazole (1.0 g, 5.98 mmol), Cu (4.0 g, 62.95 mmol) in DMF (20.0 ml) was added potassium carbonate (6.0 g, 43.41 mmol) under nitrogen and stirring. Heating was started. The reaction was carried out at 150° C. for 5 h. After cooling, the reaction mixture was filtrated. The solid residues were carefully washed with THF. THF was evaporated from the combined filtration solution. Water (150.0 ml) was added, the brown solid product was obtained by filtration. The crude product was purified by silica gel column chromatography using toluene/ethyl acetate (9.7:0.3) as eluent. After evaporating solvent, the white solid was recrystallized from THF/methanol and finally dried under vacuum. Pure product was obtained as white solid in 0.99 g (86.0%) yield. $^1$H NMR (399 MHz, CDCl$_3$, δ): 8.47 (d, J=2.4 Hz, 2H), 8.16 (d, J=8.0 Hz, 4 Hz), 8.01 (t, J=1.6 Hz, 1H), 7.69-7.64 (m, 2H), 7.58 (d, J=8.0 Hz, 4H), 7.45 (m, 4H), 7.41 (t, J=8.0 Hz, 1H), 7.34 (m, 4H), 7.08 (m, 1H), 3.87 (s, 3H, OCH$_3$). $^{13}$C NMR (100 MHz, CDCl$_3$, δ): 164.72, 164.02, 159.99, 140.90, 140.21, 130.28, 128.58, 127.21, 126.21, 124.88, 123.76, 122.40, 120.57, 120.48, 119.33, 118.29, 111.61, 109.68, 94.23, 55.55. [M]$^+$ calcd for C$_{39}$H$_{26}$N$_4$O$_2$, 582.2. found 582.2. Anal. Calcd for C$_{39}$H$_{26}$N$_4$O$_2$: C, 80.39; H, 4.50; N, 9.62. Found: C, 80.32; H, 4.41; N, 9.60.

Synthesis of 3-(5-(3,5-dicarbazol-9-ylphenyl)-1,3,4-oxadiazol-2-yl)phenol

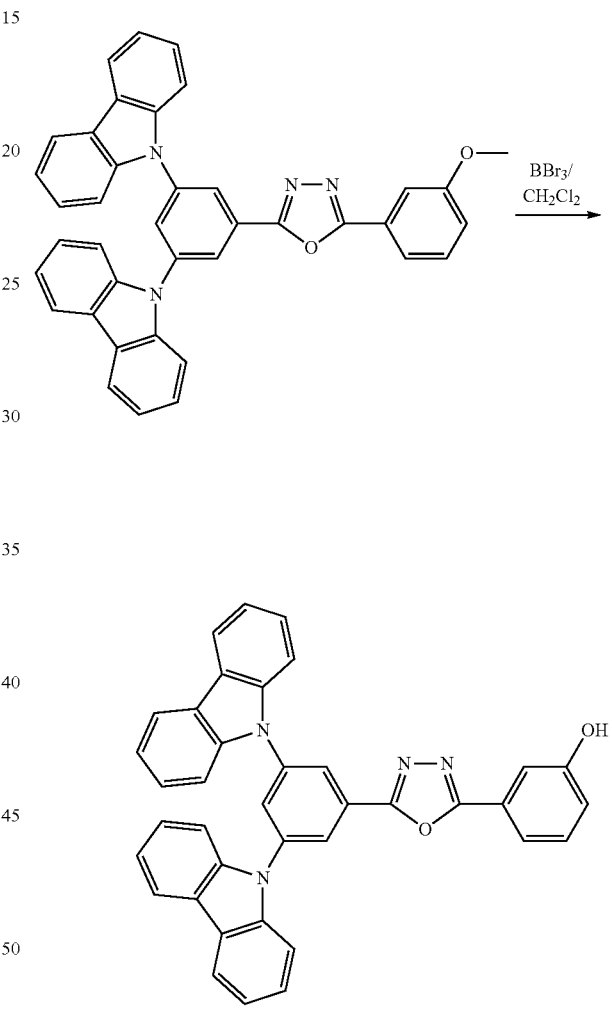

To a solution of 2-(3,5-dicarbazol-9-ylphenyl)-5-(3-methoxyphenyl)-1,3,4-oxadiazole (0.95 g, 1.63 mmol) in dichloromethane (20.0 ml) was dropwise added BBr$_3$ (7.0 ml, 1M in dichloromethane) at −78° C. (dry-ice/acetone) under nitrogen. After addition of BBr$_3$ solution, the reaction was taken to room temperature and kept at room temperature for 5.5 h. The reaction mixture was poured into ice-water (70.0 ml). Dichloromethane was evaporated under reduced pressure. The white solid was collected by filtration. After drying under vacuum, product as white solid was obtained in 0.92 g (98.9%) yield. $^1$H NMR (400 MHz, DMSO-d$_6$, δ): 10.01 (s, br, 1H, OH), 8.46 (d, J=1.6 Hz, 2H), 8.28 (d, J=8.0 Hz, 4H), 8.17 (t, J=1.6 Hz, 1H), 7.66 (d, J=8.0 Hz, 4H), 7.59 (d, J=8.0 Hz, 1H), 7.50

(m, 5H), 7.34 (m, 5H), 7.00 (dd, J$_1$=8.4 Hz, J$_2$=2.4 Hz, 1H). MS-EI (m/z): [M]$^+$ calcd for C$_{38}$H$_{24}$N$_4$O$_2$, 568.2. found 568.2.

Example 2

Figure 6:
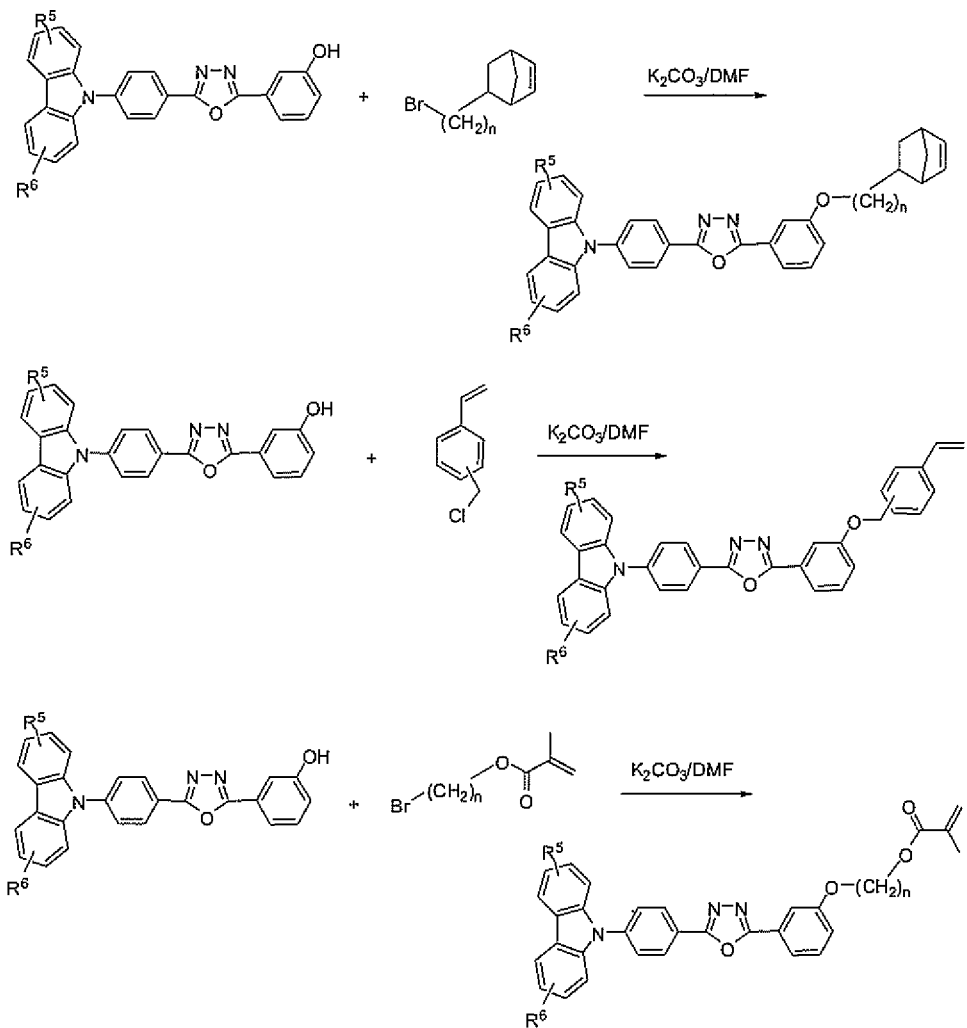
FIG. 6 schematically discloses a synthetic scheme for linking polymerizable norbornenyl, styrenyl, or methacrylyl groups to the ambipolar precursor compound from FIG. 3, to form compounds within generic formulas (Ia), (IIa), and (IIIa).
Figure 7:
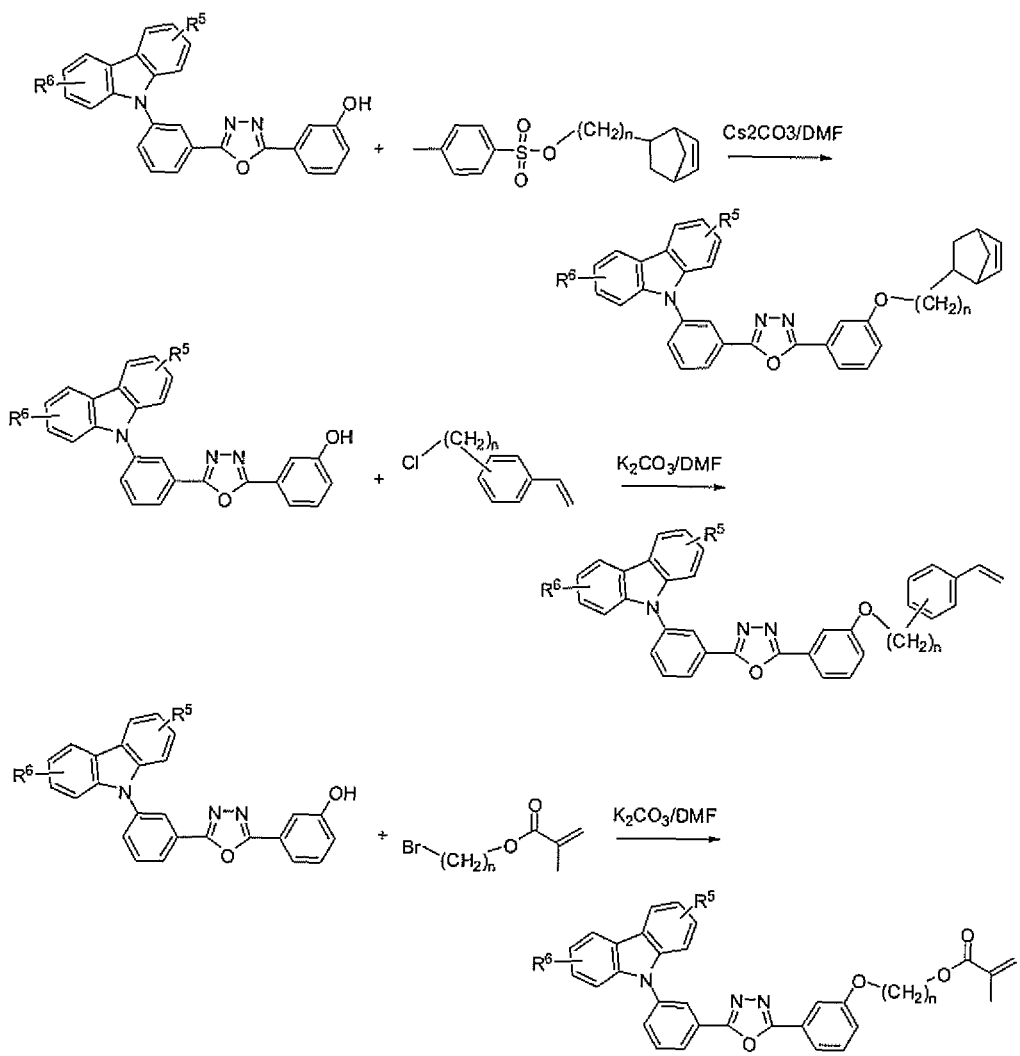
FIG. 7 schematically discloses a synthetic scheme for linking polymerizable norbornenyl, styrenyl, or methacrylyl groups to the ambipolar precursor compound from FIG. 4, to form compounds within generic formulas (Ia), (IIa), and (IIIa).
Figure 8:
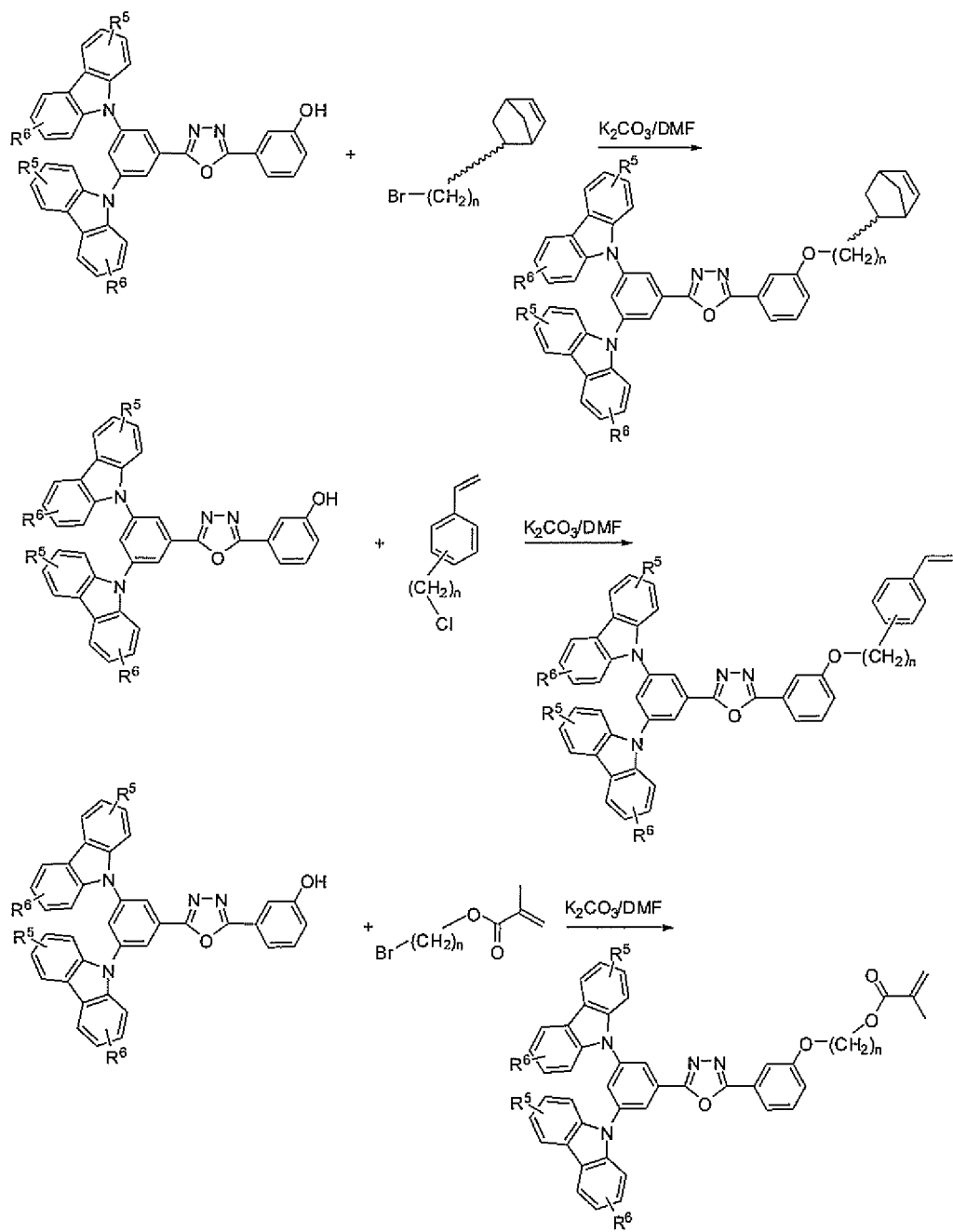
FIG. 8 schematically discloses a synthetic scheme for linking polymerizable norbornenyl, styrenyl, or methacrylyl groups to the ambipolar precursor compound from FIG. 5, to form compounds within generic formulas (Ia), (IIa), and (IIIa).

Synthesis of Ambipolar Monomers (See FIGS. 6-8)

Synthesis of 2-(4-carbazol-9-ylphenyl)-5-(3-(4-vinylbenzyloxy)phenyl)-1,3,4-oxadiazole mixed with 2-(4-carbazol-9-ylphenyl)-5-(3-(3-vinylbenzyloxyl) phenyl)-1,3,4-oxadiazole

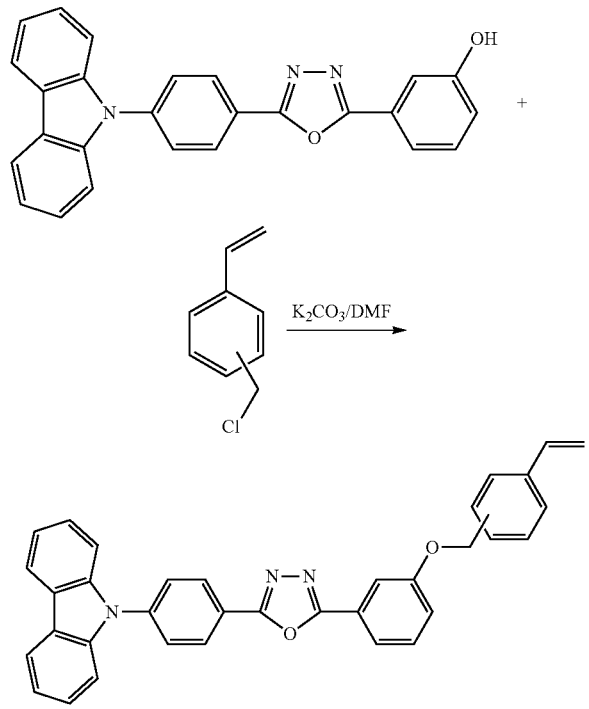

To a solution of 3-(5-(4-carbazol-9-ylphenyl)-1,3,4-oxadiazol-2-yl)phenol (1.0 g, 2.48 mmol) and 1-(chloromethyl)-4-vinylbenzene/1-(chloromethyl)-3-vinylbenzene (1:1) (0.4 g, 2.62 mmol) in DMF (20.0 ml) was added K$_2$CO$_3$ (4.0 g, 28.94 mmol) at room temperature under stirring. The reaction was carried out at room temperature for 23 h. Water (100.0 ml) was added. Brown solid product was obtained by filtration. The crude product was purified by silica gel column chromatography using dichloromethane as eluent. After removal of solvent, white solid product was recrystallized from THF/methanol/water. White pure solid product was obtained by filtration. After vacuum dry, the product as white solid in 1.16 g (89.9%) was obtained. $^1$H NMR (400 MHz, CDCl$_3$, δ): 8.36 (d, J=8.4 Hz, 2H), 8.14 (d, 3=8.0 Hz, 2H), 7.80-7.75 (m, 4H), 7.52-7.30 (m, 11H), 7.19 (m, 1H), 6.78-6.69 (m, 1H, C=C—H), 5.81-5.74 (m, 1H, C=C—H), 5.30-5.25 (m, 1H, C=C—H), 5.16 (s, 1H, 0.5×OCH$_2$), 5.15 (s, 1H, 0.5×OCH$_2$). $^{13}$C NMR (100 MHz, CDCl$_3$, δ): 164.76, 163.97, 159.54, 140.86, 140.20, 136.94, 132.34, 130.22, 128.55, 127.18, 126.20, 124.79, 123.75, 122.40, 120.55, 120.45, 119.10, 118.66, 112.26, 109.67, 68.31, 49.53, 45.37, 42.48, 38.65, 34.67, 32.38, 29.18, 28.37, 26.24. [M]$^+$ calcd for C$_{35}$H$_{25}$N$_3$O$_2$, 519.2. found 519.2. Anal. Calcd for C$_{35}$H$_{25}$N$_3$O$_2$: C, 80.90; H, 4.85; N, 8.09. Found: C, 80.61; H, 4.87; N, 8.05.

Synthesis of 2-(3-(5-(4-carbazol-9-ylphenyl)-1,3,4-oxadiazol-2-yl)phenoxy)ethyl methacrylate

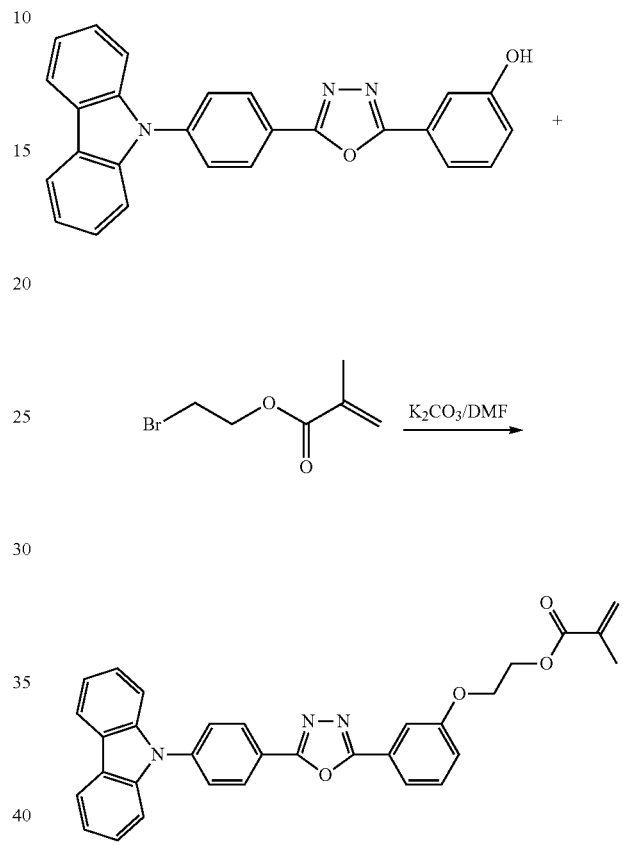

To a solution of 3-(5-(4-carbazol-9-ylphenyl)-1,3,4-oxadiazol-2-yl)phenol (1.0 g, 2.48 mmol) and 2-bromoethyl methacrylate (0.5 g, 2.59 mmol) in DMF (20.0 ml) was added K$_2$CO$_3$ (4.0 g, 28.94 mmol) at room temperature under stirring. The reaction was carried out at room temperature for 23.5 h. Water (100.0 ml) was added. Brown solid product was obtained by filtration. The crude product was purified by silica gel column chromatography using dichloromethane/ ethyl acetate (9.7:0.3) as eluent. After removal of solvent, white glass-like solid product was dissolved in acetone. The acetone solution was slowly dropped into methanol (60.0 ml) under stirring. After addition of acetone solution, water (30.0 ml) was added into this solution. White solid product was obtained and collected by filtration. After vacuum dry, the product as white solid in 0.98 g (76.6%) was obtained. $^1$H NMR (400 MHz, CDCl$_3$, δ): 8.37 (d, J=8.0 Hz, 2H), 8.14 (dd, J$_1$=8.0 Hz, J$_2$=0.8 Hz, 2 Hz), 7.78-7.72 (m, 4H), 7.50-7.41 (m, 5H), 7.31 (m, 2H), 7.12 (dd, J$_1$=8.0 Hz, J$_2$=2.4 Hz, 1H), 6.16 (d, J=0.4 Hz, 1H, C=C—H), 5.59 (t, J=0.8 Hz, 1H, C=C—H), 4.55 (t, J=4.8 Hz, 2H, OCH$_2$), 4.33 (t, J=4.8 Hz, 2H, OCH$_2$), 1.96 (s, 3H, CH$_3$). $^{13}$C NMR (100 MHz, CDCl$_3$, δ): 167.28, 164.57, 164.06, 140.94, 140.22, 135.89, 130.40, 128.59, 127.21, 126.21, 124.97, 123.78, 122.34, 120.58, 120.47, 119.79, 118.74, 112.47, 109.87, 66.22, 62.86, 18.30.

[M]+ calcd for $C_{32}H_{25}N_3O_4$, 515.2. found 515.2. Anal. Calcd for $C_{32}H_{25}N_3O_4$: C, 74.55; H, 4.89; N, 8.15. Found: C, 74.29; H, 4.79; N, 8.13.

Synthesis of 2-(3,5-Dicarbazol-9-ylphenyl)-5-(3-(5-(bicycle[2,2,1]hept-5-en-2-yl)pentyloxy)phenyl)-1,3,4-oxadiazole

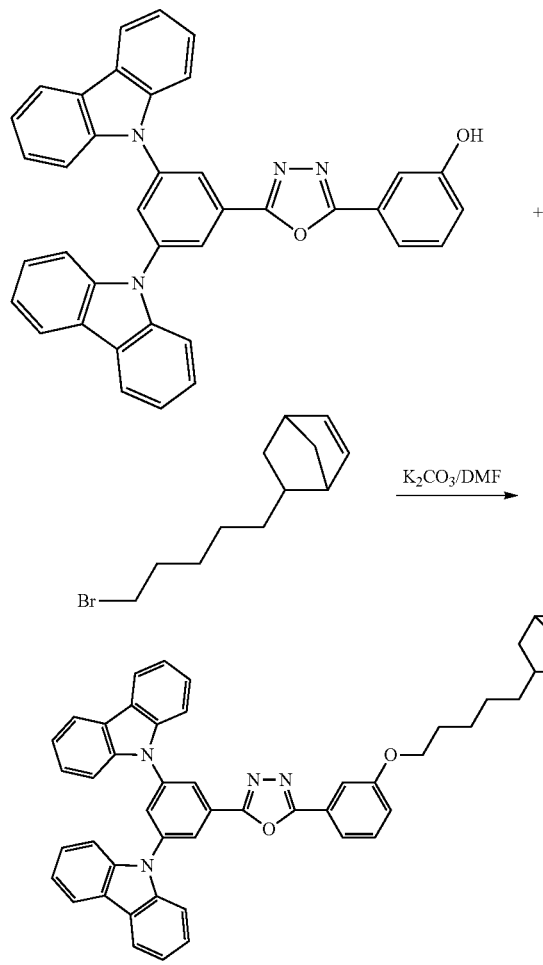

To a solution of 3-(5-(3,5-dicarbazol-9-ylphenyl)-1,3,4-oxadiazol-2-yl)phenol (0.90 g, 2.23 mmol) and 5-(bromomethyl)bicycle[2,2,1]hept-2-ene (0.74 g, 3.04 mmol) in DMF (10.0 ml) was added $K_2CO_3$ (5.0 g, 36.18 mmol) at room temperature under stirring. The reaction was carried out at room temperature for 24 h. Water (150.0 ml) was added. Brown semi-solid product was obtained by filtration. The crude product was purified by silica gel column chromatography using toluene/ethyl acetate (9.5:0.5) as eluent. After removal of solvents, glass-like solid was obtained. Acetone (3.0 ml) was added into this glass-like solid, at beginning solid was disappeared. However, after several min, white solid was appeared. The methanol (90%) in water was added into acetone solution under stirring. White solid product was obtained by filtration. After vacuum dry, the product as white solid in 0.99 g (78.6%) was obtained. $^1H$ NMR (400 MHz, $CDCl_3$, δ): 8.48 (d, J=1.6 Hz, 2H), 8.17 (d, $J_1$=8.0 Hz, 4H), 8.02 (t, J=1.6 Hz, 1H), 7.68-7.58 (m, 6H), 7.50-7.33 (m, 9H), 7.07 (dd, $J_1$=8.0 Hz, $J_2$=2.0 Hz, 1H), 6.09 (q, J=2.8 Hz, endo), 6.08 (q, J=2.8 Hz, 0.3H, exo), 6.00 (q, J=2.8 Hz, 0.3H, exo), 5.90 (q, J=2.8 Hz, 0.7H, endo), 4.00 (t, J=6.4 Hz, 2H, $OCH_2$), 2.74 (s, br, 1.7H), 2.49 (s, br, 0.3H), 1.96 (m, 1H), 1.81 (m, 2.5H), 1.46-1.03 (m, 7.5H), 0.47 (m, 1H). $^{13}C$ NMR (100 MHz, $CDCl_3$, δ): 165.24, 163.26, 159.58, 140.47, 140.31, 136.91, 132.33, 130.23, 128.02, 127.42, 126.42, 124.44, 123.81, 123.72, 120.79, 120.59, 119.25, 118.96, 112.29, 109.52, 68.34, 49.52, 45.37, 42.48, 38.64, 34.63, 32.37, 29.13, 28.34, 26.20. [M]+ calcd for $C_{50}H_{42}N_4O_2$, 730.3. found 730.4. Anal. Calcd for $C_{50}H_{42}N_4O_2$: C, 82.16; H, 5.79; N, 7.67. Found: C, 82.31; H, 5.77; N, 7.68.

Synthesis of 2-(3,5-Dicarbazol-9-ylphenyl)-5-(3-(4-vinylbenzyloxyl)phenyl)-1,3,4-oxadiazole mixed with 2-(3,5-dicarbazol-9-ylphenyl)-5-(3-(3-vinylbenzyloxyl)phenyl)-1,3,4-oxadiazole (1:1)

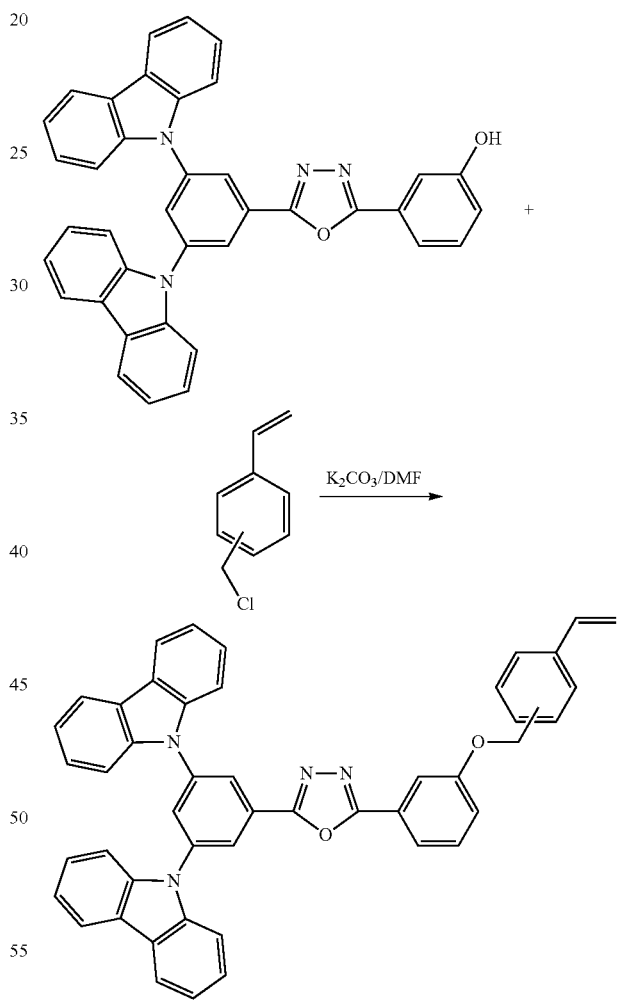

To a solution of 3-(5-(3,5-dicarbazol-9-ylphenyl)-1,3,4-oxadiazol-2-yl)phenol (0.7 g, 1.23 mmol) and 1-(chloromethyl)-4-vinylbenzene/1-(chloromethyl)-3-vinylbenzene (1:1) (0.2 g, 1.31 mmol) in DMF (20.0 ml) was added $K_2CO_3$ (2.0 g, 14.47 mmol) at room temperature under stirring. The reaction was carried out at room temperature for 21 h. Water (100.0 ml) was added. Brown solid product was obtained by filtration and washed with methanol. The crude product was purified by silica gel column chromatography using dichloromethane/hexanes (7:3) as eluent. After removal of solvent, white glass-like solid product was dissolved in dichloromethane. The solution was added into methanol (100.0 ml) under stirring. White solid product was obtained and collected by filtration. After vacuum dry, the product as white solid in 0.74 g (88.1%) was obtained. $^1$H NMR (400 MHz, CDCl$_3$, δ): 8.46 (d, J=2.0 Hz, 2H), 8.17 (dd, J$_1$=8.0 Hz, J$_2$=0.8 Hz, 4H), 8.01 (t, J=2.0 Hz, 1H), 7.73-7.69 (m, 2H), 7.58 (d, J=8.0 Hz, 4H), 7.49-7.28 (m, 13H), 7.16 (m, 1H), 6.71-6.62 (m, 1H, C=C—H), 5.75-5.68 (m, 1H, C=C—H), 5.24-5.20 (m, 1H, C=C—H), 5.11 (s, 1H, 0.5×OCH$_2$), 5.10 (s, 1H, 0.5×OCH$_2$). $^{13}$C NMR (100 MHz, CDCl$_3$, δ): 165.10, 163.28, 159.09, 140.49, 140.31, 137.97, 136.54, 136.42, 136.28, 135.74, 130.38, 128.82, 127.70, 127.38, 126.88, 126.43, 125.98, 125.32, 124.56, 123.83, 123.72, 120.81, 120.60, 119.79, 119.31, 114.38, 114.22, 112.73, 109.52, 70.19, 70.02. [M]$^+$ calcd for C$_{47}$H$_{32}$N$_4$O$_2$, 684.3. found 684.2. Anal. Calcd for C$_{47}$H$_{32}$N$_4$O$_2$: C, 82.44; H, 4.71; N, 8.18. Found: C, 82.18; H, 4.71; N, 8.20.

Synthesis of 2-(3-(5-(3,5-Dicarbazol-9-ylphenyl)-1,3,4-oxadiazol-2-yl)phenoxy)ethyl methacrylate To a solution of 3-(5-(3,5-dicarbazol-9-ylphenyl)-1,3,4-oxadiazol-2-yl)phenol (0.7 g, 1.23 mmol) and 2-bromoethyl methacrylate (0.25 g, 1.30 mmol) in DMF (20.0 ml) was added K$_2$CO$_3$ (2.0 g, 14.47 mmol) at room temperature under stirring. The reaction was carried out at room temperature for 21 h. Water (100.0 ml) was added. Brown solid product was obtained by filtration and washed with methanol. The crude product was purified by silica gel column chromatography using dichloromethane/ethyl acetate (9.5:0.5) as eluent. After removal of solvent, white glass-like solid product was dissolved in THF (10.0 ml). Methanol (120.0 ml) was added into THF solution. White solid product was obtained and collected by filtration. After vacuum dry, the product as white solid in 0.7 g (83.3%) was obtained. $^1$H NMR (400 MHz, CDCl$_3$, δ): 8.47 (d, 5=1.6 Hz, 2H), 8.16 (d, J=8.0 Hz, 4 Hz), 8.01 (d, J=1.6 Hz, 1H), 7.71 (dt, J$_1$=8.0 Hz, J$_2$=1.6 Hz, 1H), 7.67 (m, 1H), 7.57 (d, J=8.4 Hz, 4H), 7.49-7.40 (m, 5H), 7.34 (m, 4H), 7.10 (m, 1H), 6.11 (t, 5=1.2 Hz, 1H), 5.55 (m, 1H), 4.49 (t, J=4.4 Hz, 2H, OCH$_2$), 4.29 (t, J=4.4 Hz, 2H, OCH$_2$), 1.92 (t, J=1.2 Hz, 3H, CH$_3$). $^{13}$C NMR (100 MHz, CDCl$_3$, δ): 167.24, 165.05, 163.35, 159.01, 140.51, 140.32, 135.85, 130.43, 128.12, 127.36, 126.43, 126.16, 124.60, 123.84, 123.77, 120.82, 120.61, 119.95, 119.09, 112.50, 109.52, 66.24, 62.81, 18.26. [M]$^+$ calcd for C$_{44}$H$_{32}$N$_4$O$_4$, 680.2.2. found 680.2. Anal. Calcd for C$_{44}$H$_{32}$N$_4$O$_4$: C, 77.63; H, 4.74; N, 8.23. Found: C, 77.49; H, 4.69; N, 8.21.

Synthesis of 2-(3-Carbazol-9-ylphenyl)-5-(3-(4-vinylbenzyloxyl)phenyl)-1,3,4-oxadiazole mixed with 2-(3-carbazol-9-ylphenyl)-5-(3-(3-vinylbenzyloxyl)phenyl)-1,3,4-oxadiazole (1:1)

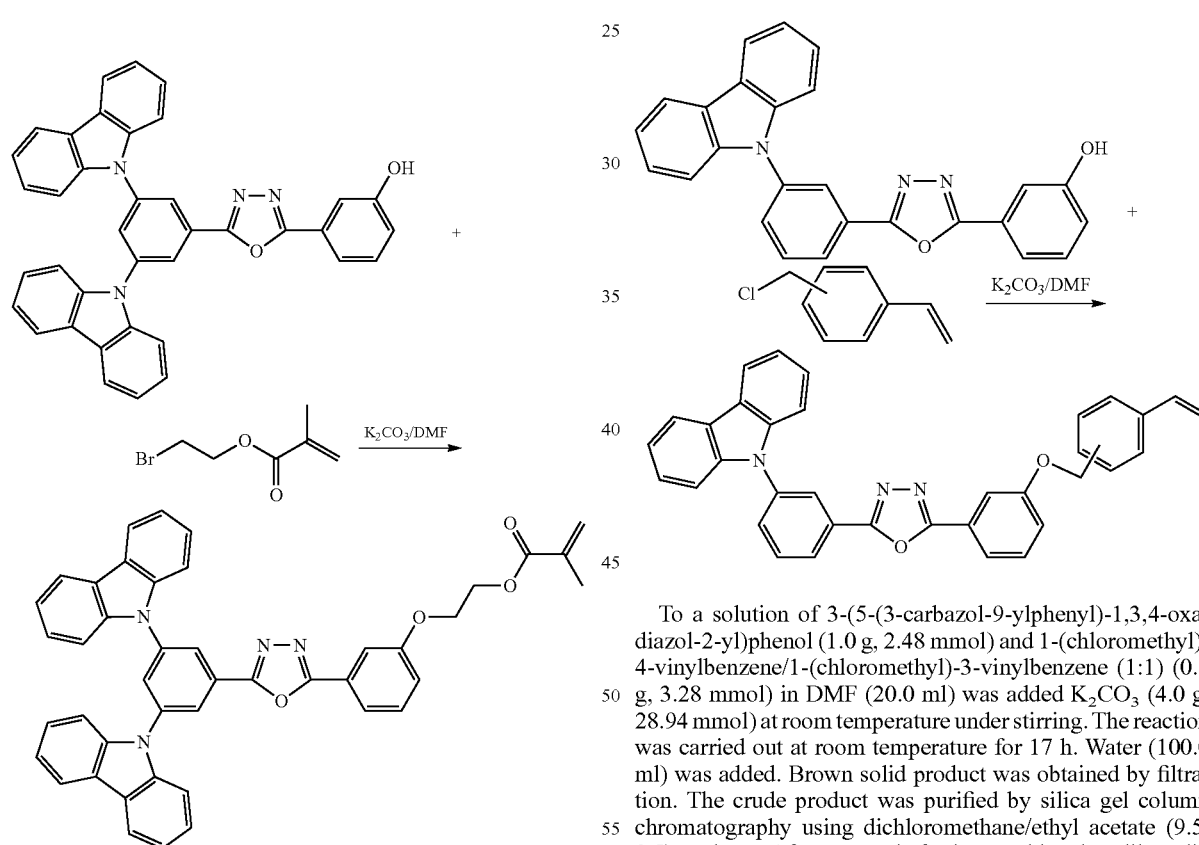

To a solution of 3-(5-(3-carbazol-9-ylphenyl)-1,3,4-oxadiazol-2-yl)phenol (1.0 g, 2.48 mmol) and 1-(chloromethyl)-4-vinylbenzene/1-(chloromethyl)-3-vinylbenzene (1:1) (0.5 g, 3.28 mmol) in DMF (20.0 ml) was added K$_2$CO$_3$ (4.0 g, 28.94 mmol) at room temperature under stirring. The reaction was carried out at room temperature for 17 h. Water (100.0 ml) was added. Brown solid product was obtained by filtration. The crude product was purified by silica gel column chromatography using dichloromethane/ethyl acetate (9.5:0.5) as eluent. After removal of solvent, white glass-like solid product was obtained. White solid product was obtained and collected from water by filtration. After vacuum dry, the product as white solid in 1.17 g (95.1%) was obtained. $^1$H NMR (400 MHz, CDCl$_3$, δ): 8.32 (m, 1H), 8.25 (m, 1H), 8.16 (dd, J$_1$=8.0 Hz, J$_2$=1.2 Hz, 2H), 7.80-7.69 (m, 4H), 7.47-7.25 (m, 11H), 7.12 (m, 1H), 6.73-6.64 (m, 1H, C=C—H), 5.77-5.70 (m, 1H, C=C—H), 5.23-5.22 (m, 1H, 5.12 (s, 1H, 0.5× OCH$_2$), 5.11 (s, 1H, 0.5×OCH$_2$). $^{13}$C NMR (100 MHz, CDCl$_3$, δ): 164.79, 163.85, 159.07, 140.61, 138.72, 137.97, 137.50, 136.58, 136.45, 136.30, 135.78, 130.85, 130.34, 128.83, 127.74, 126.92, 126.46, 126.20, 125.99, 125.83, 125.41, 125.35, 124.75, 123.56, 120.45, 120.38, 119.70, 119.66, 119.06, 114.40, 114.22, 112.69, 109.55, 70.17, 70.01. [M]$^+$ calcd for $C_{35}H_{25}N_3O_2$, 519.2. found 519.2. Anal. Calcd for $C_{35}H_{25}N_3O_2$: C, 80.90; H, 4.85; N, 8.09. Found: C, 80.69; H, 4.82; N, 8.02.

Synthesis of 2-(3-(5-(3-Carbazol-9-ylphenyl)-1,3,4-oxadiazol-2-yl)phenoxy)ethyl methacrylate

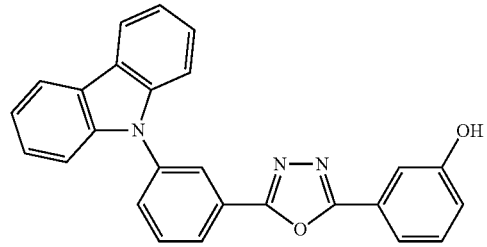

+

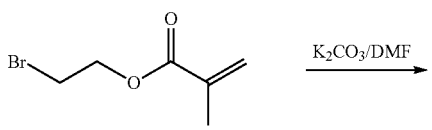

$\xrightarrow{K_2CO_3/DMF}$

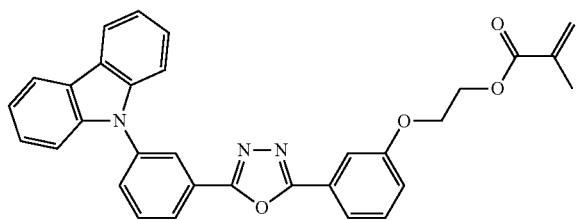

To a solution of 3-(5-(3-carbazol-9-ylphenyl)-1,3,4-oxadiazol-2-yl)phenol (0.80 g, 1.98 mmol) and 2-bromoethyl methacrylate (0.40 g, 2.07 mmol) in DMF (15.0 ml) was added $K_2CO_3$ (4.0 g, 28.94 mmol) at room temperature under stirring. The reaction was carried out at room temperature for 21 h. Water (100.0 ml) was added. Brown solid product was obtained by filtration. The crude product was purified by silica gel column chromatography using dichloromethane/ethyl acetate (9.5:0.5) as eluent. After removal of solvent, Methanol (120.0 ml) was added into this glass-like solid. After removal of methanol, White solid product was obtained and collected from water by filtration. After vacuum dry, the product as white solid in 038 g (76.4%) was obtained. $^1$H NMR (400 MHz, CDCl$_3$, δ): 8.34 (m, 1H), 8.26 (m, 1H), 8.15 (dd, $J_1$=8.0 Hz, $J_2$=0.8 Hz, 2H), 7.78-7.66 (m, 4H), 7.42 (m, 5H), 7.31 (m, 2H), 7.10 (m, 1H), 6.12 (t, J=1.2 Hz, 1H), 5.56 (m, 1H), 4.51 (m, 2H, OCH$_2$), 4.27 (m, 2H, OCH$_2$), 1.93 (t, 3=1.2 Hz, 3H, CH$_3$). $^{13}$C NMR (100 MHz, CDCl$_3$, δ): 167.25, 164.71, 163.88, 158.97, 140.61, 138.73, 135.86, 130.86, 130.37, 126.19, 125.85, 125.78, 125.43, 124.80, 123.56, 120.45, 120.37, 119.85, 118.88, 112.42, 109.54, 66.21, 62.84, 18.27. [M]$^+$ calcd for $C_{32}H_{25}N_3O_4$, 515.2. found 515.2. Anal. Calcd for $C_{32}H_{25}N_3O_4$: C, 74.55; H, 4.89; N, 8.15. Found: C, 74.26; H, 4.83; N, 8.03.

Synthesis of 2-(3-carbazol-9-ylphenyl)-5-(3-(5-(bicycle[2,2,1]hept-5-en-2-ylmethoxy)phenyl)-1,3,4-oxadiazole

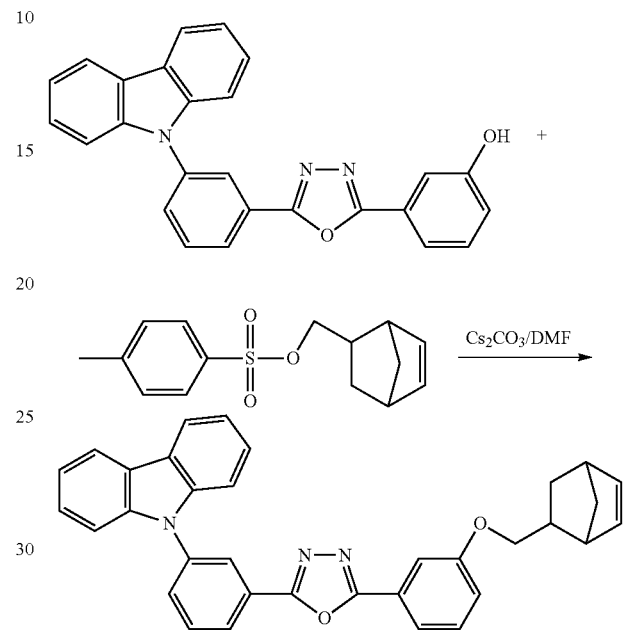

To a solution of 3-(5-(3-carbazol-9-ylphenyl)-1,3,4-oxadiazol-2-yl)phenol (1.0 g, 2.48 mmol) and bicycle[2,2,1]hept-5-en-2-ylmethyl 4-methylbenzenesulfonate (0.8 g, 2.93 mmol) in DMF (20.0 ml) was added Cs$_2$CO$_3$ (1.6 g, 4.91 mmol) at room temperature under stirring. The reaction was heated to 100° C. and carried out at this temperature for 3 h. Heating was stopped, the reaction mixture was cooled down to room temperature. Water (120.0 ml) was added. Brown solid product was obtained by filtration. The crude product was purified by silica gel column chromatography using toluene/ethyl acetate (9.5:0.5) as eluent. After removal of solvents, glass-like solid was obtained. Glass-like solid was dissolved in acetone and the acetone solution was added into methanol/water (100.0 ml) (75:25) under stirring White solid was obtained and collected by filtration. After vacuum dry, the product as white solid in 1.07 g (84.9%) was obtained. $^1$H NMR (400 MHz, CDCl$_3$, δ): 8.34 (t, J=1.2 Hz, 1H), 8.27 (in, 1 Hz), 8.17 (d, J=8.0 Hz, 2H), 7.81-7.76 (m, 2H), 7.70-7.61 (m, 2H), 7.46-7.31 (m, 7H), 7.07 (m, 1H), 6.19-5.95 (m, 2H, C=C—H), 4.10 (dd, $J_1$=8.8 Hz, $J_2$=6.0 Hz, 0.6H, 0.3×OCH$_2$), 3.92 (t, J=8.8 Hz, 0.4H, 0.2×OCH$_2$), 3.78 (dd, $J_1$=8.8 Hz, $J_2$=6.0 Hz, 0.4H, 0.2×OCH$_2$), 3.62 (t, J=8.8 Hz, 0.6H, 0.3×OCH$_2$), 3.05 (s, br, 0.4H), 2.86 (m, br, 1.6H), 2.57 (m, 1H), 1.92 (m, 1H), 1.50-1.24 (m, 3H), 0.65 (m, 1H). $^{13}$C NMR (100 MHz, CDCl$_3$, δ): 164.91, 163.81, 163.83, 159.55, 140.62, 138.71, 137.65, 136.88, 136.36, 132.26, 130.83, 130.31, 130.28, 130.21, 130.16, 126.19, 125.85, 125.42, 124.68, 124.63, 123.56, 120.45, 120.37, 119.23, 119.13, 118.84, 118.81, 112.28, 112.23, 109.55, 72.55, 71.75, 49.41, 45.04, 43.86, 43.68, 42.21, 41.58, 38.52, 38.30, 29.60, 28.98. [M]$^+$ calcd for $C_{34}H_{27}N_3O_2$, 509.2. found 509.2. Anal. Calcd for $C_{34}H_{27}N_3O_2$: C, 80.13; H, 5.35; N, 8.25. Found: C, 80.00; H, 5.33; N, 8.19.

Example 3

Synthesis of Ambipolar Homopolymers (See FIGS. 9-10)

Synthesis of Poly(2-(3-(5-(4-carbazol-9-ylphenyl)-1,3,4-oxadiazol-2-yl)phenoxy)ethyl methacrylate) ("Ambi-Polymer 1")

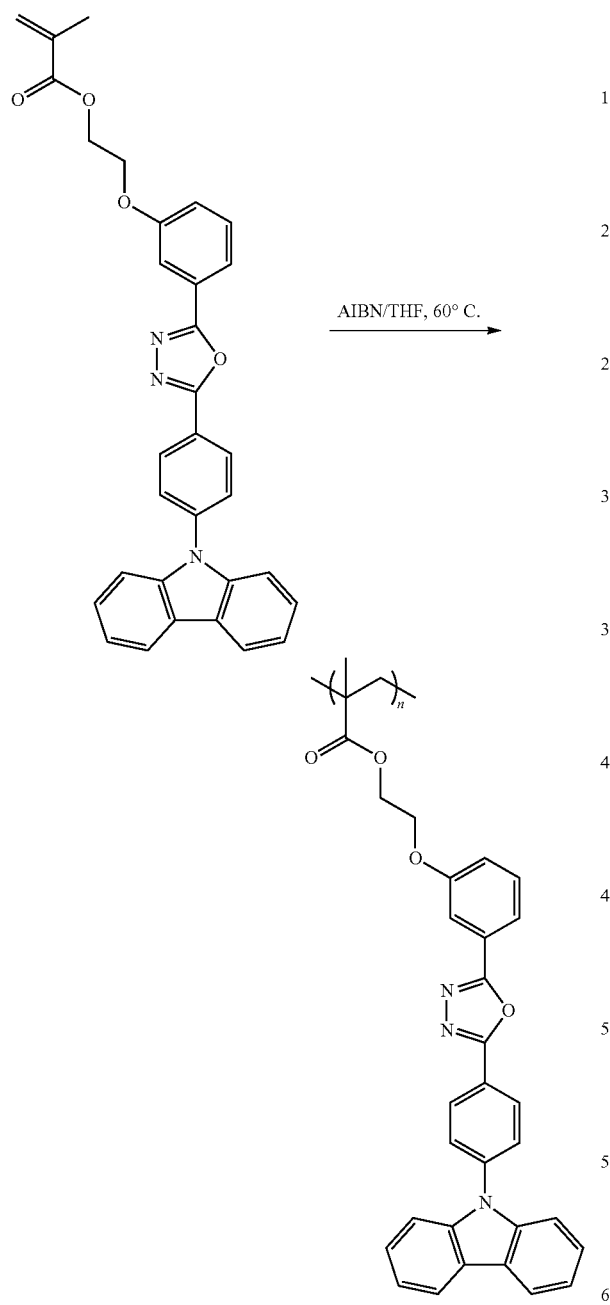

A Schlenk flask was charged with 2-(3-(5-(4-carbazol-9-ylphenyl)-1,3,4-oxadiazol-2-yl)phenoxy)ethyl methacrylate (0.5 g, 0.97 mmol), AIBN (2.5 mg, 0.015 mmol) and dry THF (4.0 ml). Polymerization mixture was purged with nitrogen (removal of oxygen), securely sealed under nitrogen, and heated to 60° C. The polymerization was carried out at 60° C. with stirring for 72 h. After cooling to room temperature, the polymer was precipitated with ethanol. The white polymer precipitate was collected by filtration, dissolved in dichloromethane, and precipitated with ethanol again. This dissolution/precipitation procedure was repeated three more times. The collected polymer was dried under vacuum. After vacuum dry, the polymer as white solid in 0.47 g (92.2%) was obtained. $^1$H-NMR (400 MHz, CDCl$_3$, δ): 8.01 (s, br), 7.94 (s, br), 7.43 (m, br), 7.23 (m, br), 7.13 (m, br), 6.89 (m, br), 4.12 (m, br), 1.97 (s, br), 1.00 (m, br). GPC (CHCl$_3$): M$_w$=150000, M$_n$=21000, PDI=7.1. Anal. Calcd for C$_{32}$H$_{25}$N$_3$O$_4$: C, 74.55; H, 4.89; N, 8.15. Found: C, 73.64; H, 4.80; N, 7.94.

Synthesis of Poly(2-(3-(5-(3-Carbazol-9-ylphenyl)-1,3,4-oxadiazol-2-yl)phenoxy)ethyl methacrylate) ("Ambi-Polymer 2")

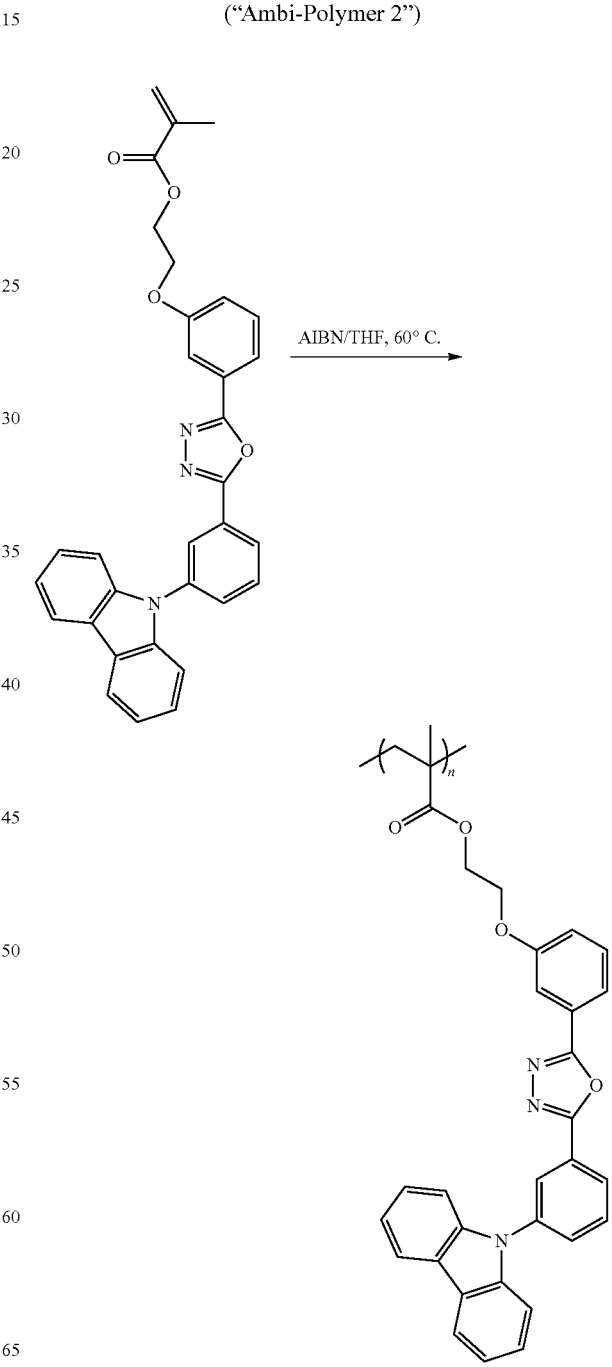

A Schlenk flask was charged with 2-(3-(5-(3-carbazol-9-ylphenyl)-1,3,4-oxadiazol-2-yl)phenoxy)ethyl methacrylate (0.5 g, 0.97 mmol), AIBN (2.5 mg, 0.015 mmol) and dry THF (6.0 ml). The polymerization mixture was purged with nitrogen (removal of oxygen), securely sealed under nitrogen, and heated to 60° C. The polymerization was carried out at 60° C. with stirring for 73 h. After cooling to room temperature, the polymer was precipitated with ethanol. The white polymer precipitate was collected by filtration, dissolved in dichloromethane, and precipitated with ethanol again. This dissolution/precipitation procedure was repeated three more times. The collected polymer was dried under vacuum. After vacuum dry, the polymer as white solid in 0.46 g (92.0%) was obtained. $^1$H-NMR (400 MHz, CDCl$_3$, δ): 8.06 (s, br), 7.93 (m, br), 7.44 (s, br), 7.22 (m, br), 7.10 (s, br), 6.81 (m, br), 4.04 (m, br), 1.82 (s, br), 1.00 (m, br). GPC (CHCl$_3$): $M_w$=103000, $M_n$=15000, PDI=6.9. Anal. Calcd for C$_{32}$H$_{25}$N$_3$O$_4$: C, 74.55; H, 4.89; N, 8.15. Found: C, 73.95; H, 4.72; N, 8.02.

Synthesis of Poly(2-(3-(5-(3,5-Dicarbazol-9-ylphenyl)-1,3,4-oxadiazol-2-yl)phenoxy)ethyl methacrylate) ("Ambi-Polymer 3")

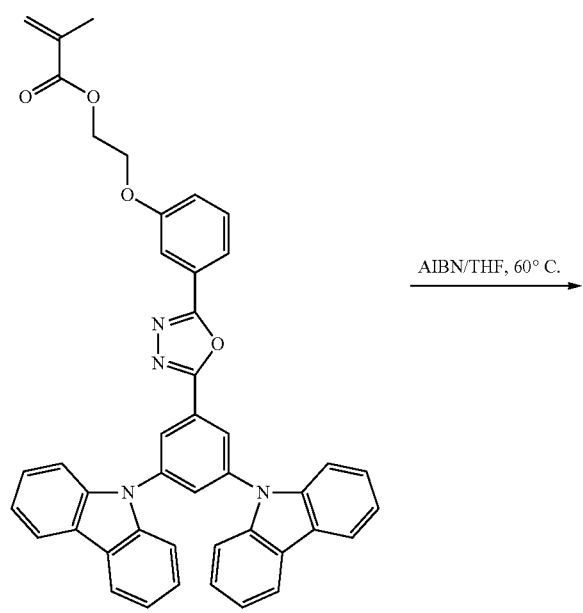

AIBN/THF, 60° C.

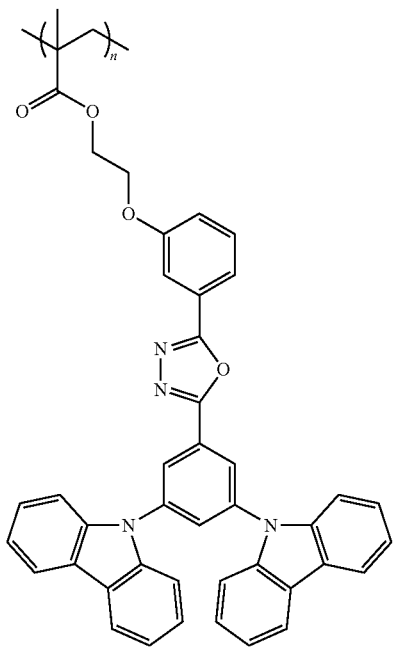

A Schlenk flask was charged with 2-(3-(5-(3,5-dicarbazol-9-ylphenyl)-1,3,4-oxadiazol-2-yl)phenoxy)ethyl methacrylate (0.5 g, 0.73 mmol), AIBN (2.0 mg, 0.012 mmol) and dry THF (5.0 ml). The polymerization mixture was purged with nitrogen (removal of oxygen), securely sealed under nitrogen, and heated to 60° C. The polymerization was carried out at 60° C. with stirring for 72 h. After cooling to room temperature, the polymer was precipitated with ethanol. The white polymer precipitate was collected by filtration, dissolved in dichloromethane, and precipitated with ethanol again. This dissolution/precipitation procedure was repeated three more times. The collected polymer was dried under vacuum. After vacuum dry, the polymer as white solid in 0.46 g (92.0%) was obtained. $^1$H-NMR (400 MHz, CDCl$_3$, δ): 8.10 (s, br), 7.82 (s, br), 7.62 (s, br), 7.31 (m, br), 7.23 (m, br), 7.17 (s, br), 7.04 (s, br), 6.78 (m, br), 3.90 (m, br), 1.73 (m, br), 0.81 (m, br). GPC (CHCl$_3$): $M_w$=140000, $M_n$=19000, PDI=7.4. Anal. Calcd for C$_{44}$H$_{32}$N$_4$O$_4$: C, 77.63; H, 4.74; N, 8.23. Found: C, 77.12; H, 4.63; N, 8.16.

Synthesis of Poly(2-(4-carbazol-9-ylphenyl)-5-(3-(4-vinylbenzyloxy)phenyl)-1,3,4-oxadiazole-2-(4-carbazol-9-ylphenyl)-5-(3-(3-vinylbenzyloxyl)phenyl)-1,3,4-oxadiazole (1:1))

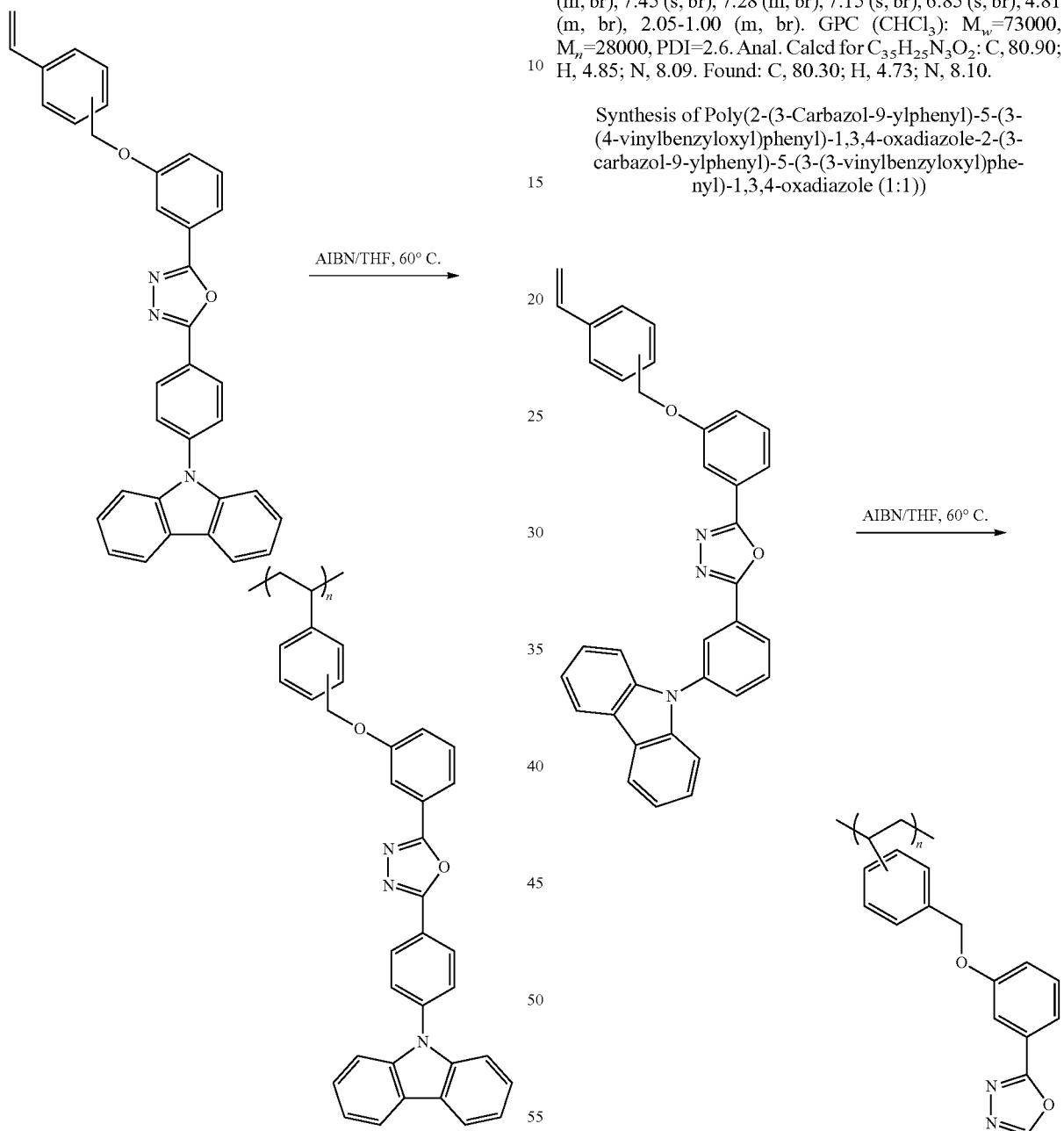

Schlenk flask was charged with 2-(4-carbazol-9-ylphenyl)-5-(3-(4-vinylbenzyloxyl)phenyl)-1,3,4-oxadiazole mixed with 2-(4-carbazol-9-ylphenyl)-5-(3-(3-vinylbenzyloxyl)phenyl)-1,3,4-oxadiazole (1:1) (0.5 g, 0.96 mmol), AIBN (3.95 mg, 0.024 mmol) and dry THF (12.0 ml). The polymerization mixture was purged with nitrogen (removal of oxygen), securely sealed under nitrogen, and heated to 60° C. The polymerization was carried out at 60° C. with stirring for 72 h. After cooling to room temperature, the polymer was precipitated with ethanol. The white polymer precipitate was collected by filtration, dissolved in dichloromethane, and precipitated with acetone again. This dissolution/precipitation (dichloromethane/acetone) procedure was repeated three more times. The collected polymer was dried under vacuum. After vacuum dry, the polymer as white solid in 0.23 g (46.0%) was obtained. $^1$H-NMR (400 MHz, CDCl$_3$, δ): 8.00 (m, br), 7.45 (s, br), 7.28 (m, br), 7.15 (s, br), 6.85 (s, br), 4.81 (m, br), 2.05-1.00 (m, br). GPC (CHCl$_3$): M$_w$=73000, M$_n$=28000, PDI=2.6. Anal. Calcd for C$_{35}$H$_{25}$N$_3$O$_2$: C, 80.90; H, 4.85; N, 8.09. Found: C, 80.30; H, 4.73; N, 8.10.

Synthesis of Poly(2-(3-Carbazol-9-ylphenyl)-5-(3-(4-vinylbenzyloxyl)phenyl)-1,3,4-oxadiazole-2-(3-carbazol-9-ylphenyl)-5-(3-(3-vinylbenzyloxyl)phenyl)-1,3,4-oxadiazole (1:1))

A Schlenk flask was charged with 2-(3-Carbazol-9-ylphenyl)-5-(3-(4-vinylbenzyloxyl)phenyl)-1,3,4-oxadiazole mixed with 2-(3-carbazol-9-ylphenyl)-5-(3-(3-vinylbenzyloxyl)phenyl)-1,3,4-oxadiazole (1:1) (0.5 g, 0.96 mmol), AIBN (3.95 mg, 0.024 mmol) and dry THF (7.0 ml). The polymerization mixture was purged with nitrogen (removal of oxygen), securely sealed under nitrogen, and heated to 60° C. The polymerization was carried out at 60° C. with stirring for 7 days. After cooling to room temperature, the polymer was precipitated with acetone. The white polymer precipitate was collected by filtration, dissolved in dichloromethane, and precipitated with acetone again. This dissolution/precipitation procedure was repeated three more times. The collected polymer was dried under vacuum. After vacuum dry, the polymer as white solid in 0.44 g (88.0%) was obtained. $^1$H-NMR (400 MHz, CDCl$_3$, δ): 8.09 (s, br), 7.96 (s, br), 7.46 (m, br), 7.25 (m, br), 7.14 (s, br), 7.03 (m, br), 6.81 (m, br), 6.42 (m, br), 4.71 (m, br), 2.00-1.00 (m, br). GPC (CHCl$_3$): M$_w$=81000, M$_n$=21000, PDI=4.0. Anal. Calcd for C$_{35}$H$_{25}$N$_3$O$_2$: C, 80.90; H, 4.85; N, 8.09. Found: C, 80.66; H, 4.76; N, 8.06

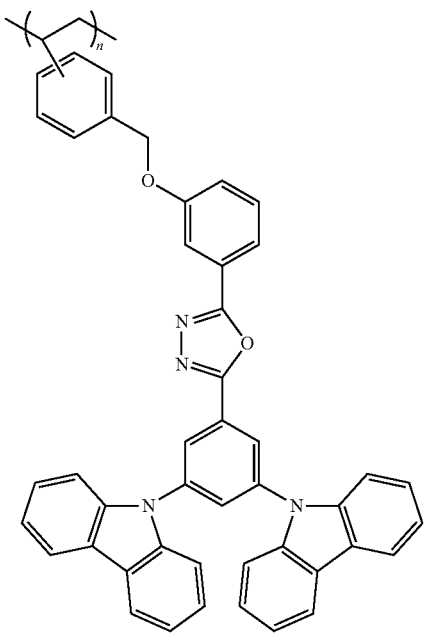

Synthesis of Poly(2-(3,5-Dicarbazol-9-ylphenyl)-5-(3-(4-vinylbenzyloxyl)phenyl)-1,3,4-oxadiazole-2-(3,5-dicarbazol-9-ylphenyl)-5-(3-(3-vinylbenzyloxyl)phenyl)-1,3,4-oxadiazole (1:1))

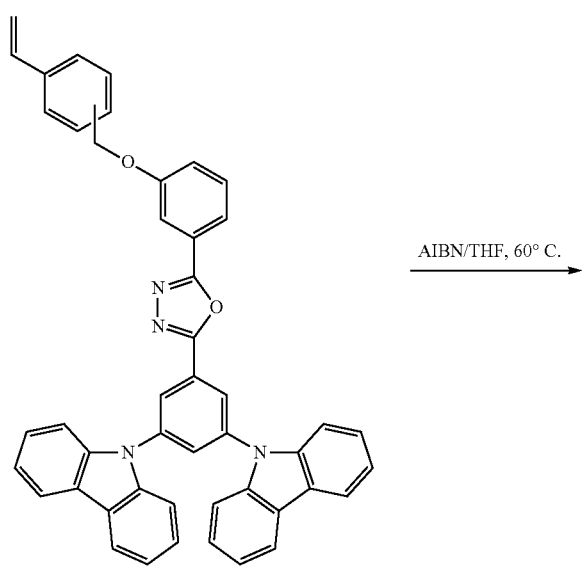

AIBN/THF, 60° C.

A Schlenk flask was charged with 2-(3,5-Dicarbazol-9-ylphenyl)-5-(3-(4-vinylbenzyloxyl)phenyl)-1,3,4-oxadiazole mixed with 2-(3,5-dicarbazol-9-ylphenyl)-5-(3-(3-vinylbenzyloxyl)phenyl)-1,3,4-oxadiazole (1:1) (0.5 g, 0.73 mmol), AIBN (3.0 mg, 0.018 mmol) and dry THF (7.0 ml). The polymerization mixture was purged with nitrogen (removal of oxygen), securely sealed under nitrogen, and heated to 60° C. The polymerization was carried out at 60° C. with stirring for 7 days. After cooling to room temperature, the polymer was precipitated with acetone. The white polymer precipitate was collected by filtration, dissolved in dichloromethane, and precipitated with acetone again. This dissolution/precipitation procedure was repeated three more times. The collected polymer was dried under vacuum. After vacuum dry, the polymer as white solid in 0.42 g (84.0%) was obtained. $^1$H-NMR (400 MHz, CDCl$_3$, 8.10 (s, br), 7.86 (s, br), 7.67 (s, br), 7.35 (s, br), 7.21 (m, br), 7.08-6.60 (m, br), 6.30 (m, br), 4.62 (m, br), 2.00-1.00 (m, br). GPC (CHCl$_3$): M$_w$=68000, PDI=4.0. Anal. Calcd for C$_{47}$H$_{32}$N$_4$O$_2$: C, 82.44; H, 4.71; N, 8.19. Found: C, 82.29; H, 4.63; N, 8.19.

Synthesis of Poly(2-(4-carbazol-9-ylphenyl)-5-(3-(5-(bicycle[2,2,1]hept-5-en-2-yl)pentyloxy)phenyl)-1,3,4-oxadiazole)

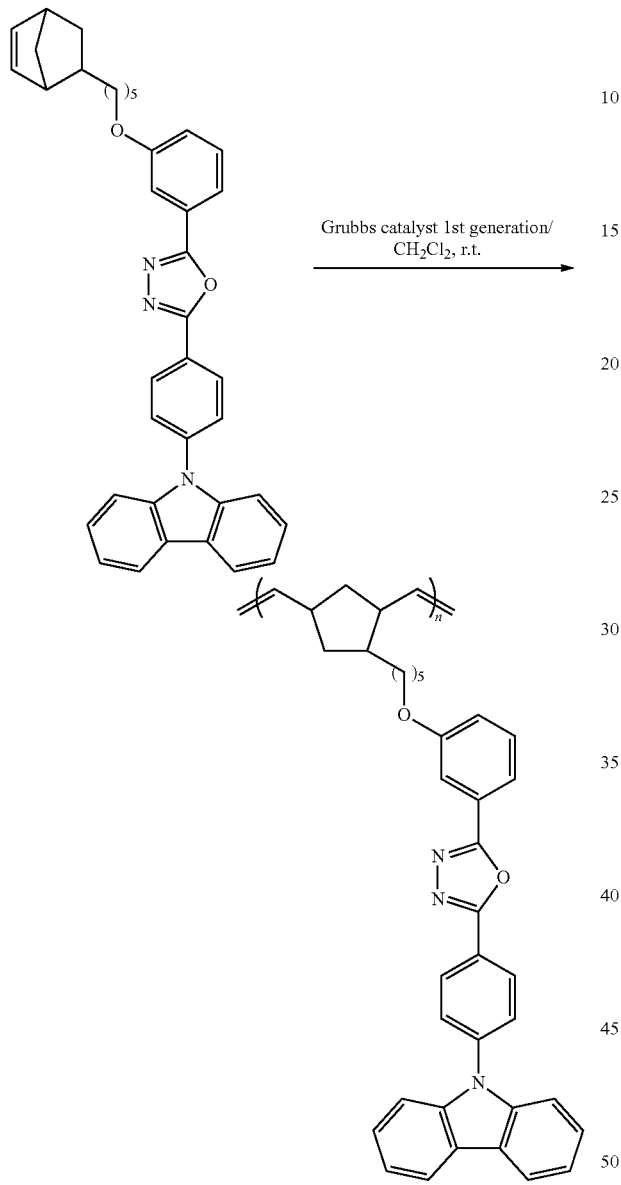

To a solution of 2-(4-carbazol-9-ylphenyl)-5-(3-(5-(bicycle[2,2,1]hept-5-en-2-yl)pentyloxy)phenyl)-1,3,4-oxadiazole (0.5 g, 0.883 mmol) in dichloromethane (8.0 ml) was added Grubbs catalyst 1$^{st}$ generation (7.2 mg, 0.0088 mmol) in dichloromethane (1.0 ml) at room temperature under stirring in glove-box. The polymerization was carried out at room temperature for 22 h. The polymerization mixture was taken out from glove-box. Ethylvinyl ether (2.0 ml) was added under stirring. After stirring 60 min, the polymer was precipitated with ethanol (100.0 ml). The off-white polymer precipitate was collected by filtration, dissolved in dichloromethane, and precipitated with ethanol again. This dissolution/precipitation procedure was repeated two more times. The final collected polymer was dried under vacuum. After vacuum dry, the polymer as off-white solid in 0.41 g (82.0%) was obtained. $^1$H-NMR (400 MHz, CDCl$_3$, δ): 8.28 (s, br), 8.08 (m, br), 7.68 (m, br), 7.38 (m, br), 7.28 (m, br), 7.02 (m, br), 5.26 (m, br), 3.96 (m, br), 2.87 (m, br), 2.72 (m, br), 2.51 (m, br), 2.37 (m, br), 1.85 (m, br), 1.75 (m, br), 1.41 (m, br), 1.26 m, br), 1.12 (m, br). GPC (CHCl$_3$): M$_w$=150000, M$_n$=52000, PDI=2.9. Anal. Calcd for C$_{38}$H$_{35}$N$_3$O$_2$: C, 80.68; H, 6.24; N, 7.43. Found: C, 79.87; H, 6.16; N, 7.30.

Synthesis of Poly(2-(3-carbazol-9-ylphenyl)-5-(3-(5-(bicycle[2,2,1]hept-5-en-2-ylmethoxy)phenyl)-1,3,4-oxadiazole)

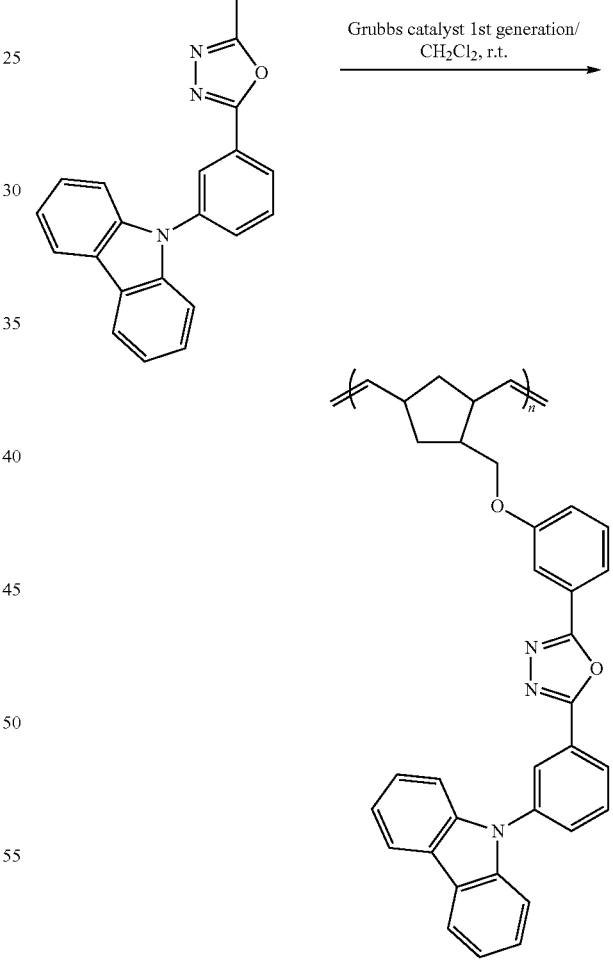

To a solution of 2-(3-carbazol-9-ylphenyl)-5-(3-(5-(bicycle[2,2,1]hept-5-en-2-ylmethoxy)phenyl)-1,3,4-oxadiazole (0.5 g, 0.981 mmol) in dichloromethane (9.0 ml) was added Grubbs catalyst 1$^{st}$ generation (8.05 mg, 0.0098 mmol) in dichloromethane (1.0 ml) at room temperature under stirring in glove-box. The polymerization was carried out at room temperature for 22 h. The polymerization mixture was taken out from glove-box. Ethylvinyl ether (2.0 ml) was added under stirring. After stirring 30 min, the polymer was precipitated with ethanol. The off-white polymer precipitate was collected by filtration, dissolved in dichloromethane, and precipitated with ethanol again. This dissolution/precipitation procedure was repeated two more times. The final collected polymer was dried under vacuum. After vacuum dry, the polymer as off-white solid in 0.38 g (76.0%) was obtained. $^1$H-NMR (400 MHz, CDCl$_3$, δ): 8.26 (s, br), 8.08 (s, br), 7.66 (s, br), 7.57 (m, br), 7.36 (s, br), 7.26 (s, br), 6.96 (m, br), 5.34 (m, br), 3.74 (m, br), 2.65 (m, br), 2.42 (m, br), 1.90 (m, br), 1.20 (m, br). GPC (CHCl$_3$): M$_w$=190000, M$_n$=73000, PDI=2.6. Anal. Calcd for C$_{34}$H$_{27}$N$_3$O$_2$: C, 80.13; H, 5.34; N, 8.11. Found: C, 79.55; H, 5.22; N, 8.11.

Synthesis of Poly(2-(3,5-Dicarbazol-9-ylphenyl)-5-(3-(5-(bicycle[2,2,1]hept-5-en-2-yl)pentyloxy)phenyl)-1,3,4-oxadiazole)

To a solution of 2-(3,5-Dicarbazol-9-ylphenyl)-5-(3-(5-(bicycle[2,2,1]hept-5-en-2-yl)pentyloxy)phenyl)-1,3,4-oxadiazole (0.5 g, 0.684 mmol) in dichloromethane (6.0 ml) was added Grubbs catalyst 1$^{st}$ generation (5.6 mg, 0.0068 mmol) in dichloromethane (1.0 ml) at room temperature under stirring in glove-box. The polymerization was carried out at room temperature for 22 h. The polymerization mixture was taken out from glove-box. Ethylvinyl ether (2.0 ml) was added under stirring. After stirring 30 min, the polymer was precipitated with ethanol. The off-white polymer precipitate was collected by filtration, dissolved in dichloromethane, and precipitated with ethanol again. This dissolution/precipitation procedure was repeated two more times. The final collected polymer was dried under vacuum. After vacuum dry, the polymer as off-white solid in 0.38 g (76.0%) was obtained. $^1$H-NMR (400 MHz, CDCl$_3$, δ): 8.39 (s, br), 8.07 (s, br), 7.91 (s, br), 7.53 (d, br), 7.39 (s, br), 7.25 (s, br), 6.94 (m, br), 5.21 (m, br), 3.87 (m, br), 2.85 (m, br), 2.69 (m, br), 2.47 (m, br), 2.32 (m, br), 1.80 (m, br), 1.66 (m, br), 1.25 (m, br),

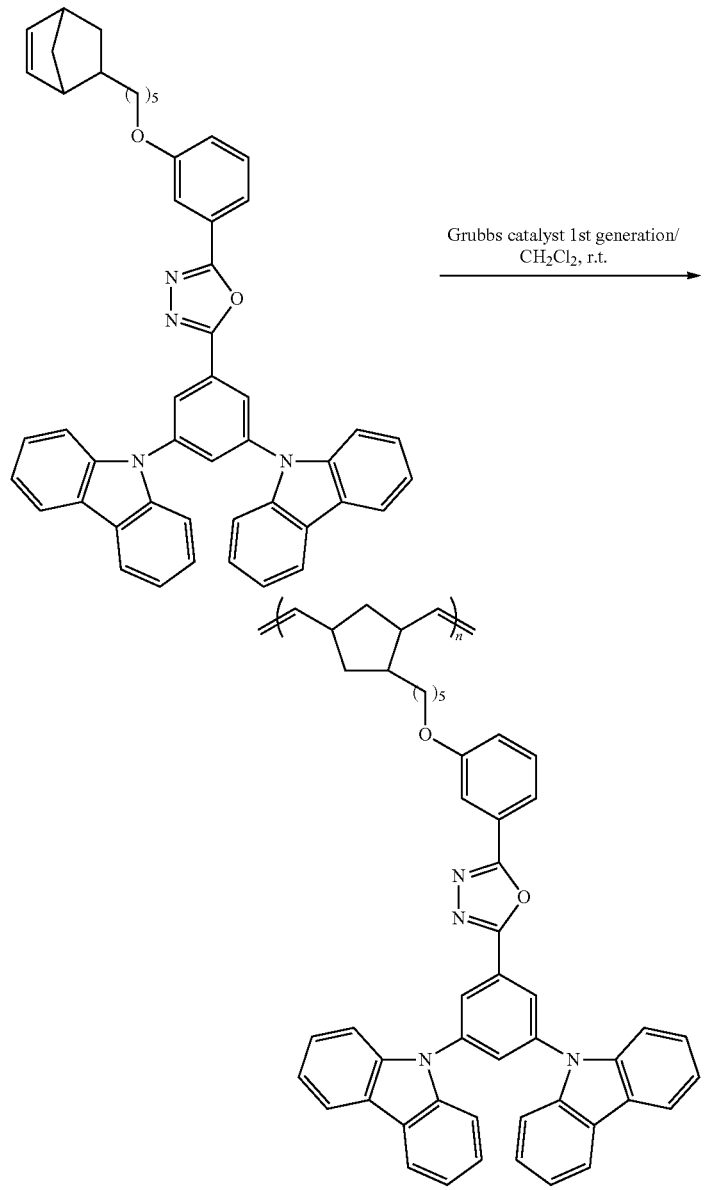

1.06 (m, br). GPC (CHCl$_3$): M$_w$=160000, M$_n$=61000, PDI=2.6. Anal. Calcd for C$_{50}$H$_{42}$N$_4$O$_2$: C, 82.16; H, 5.79; N, 7.67. Found: C, 81.17; H, 5.74; N, 7.58.

Example 4

Synthesis of Ambipolar Copolymers of Type (IV)

Synthesis of Poly[11-(6-(9H-carbazol-9-yl)-9H-3,9'-bicarbazol-9-yl)undecyl bicyclo[2.2.1]hept-5-ene-2-carboxylate]

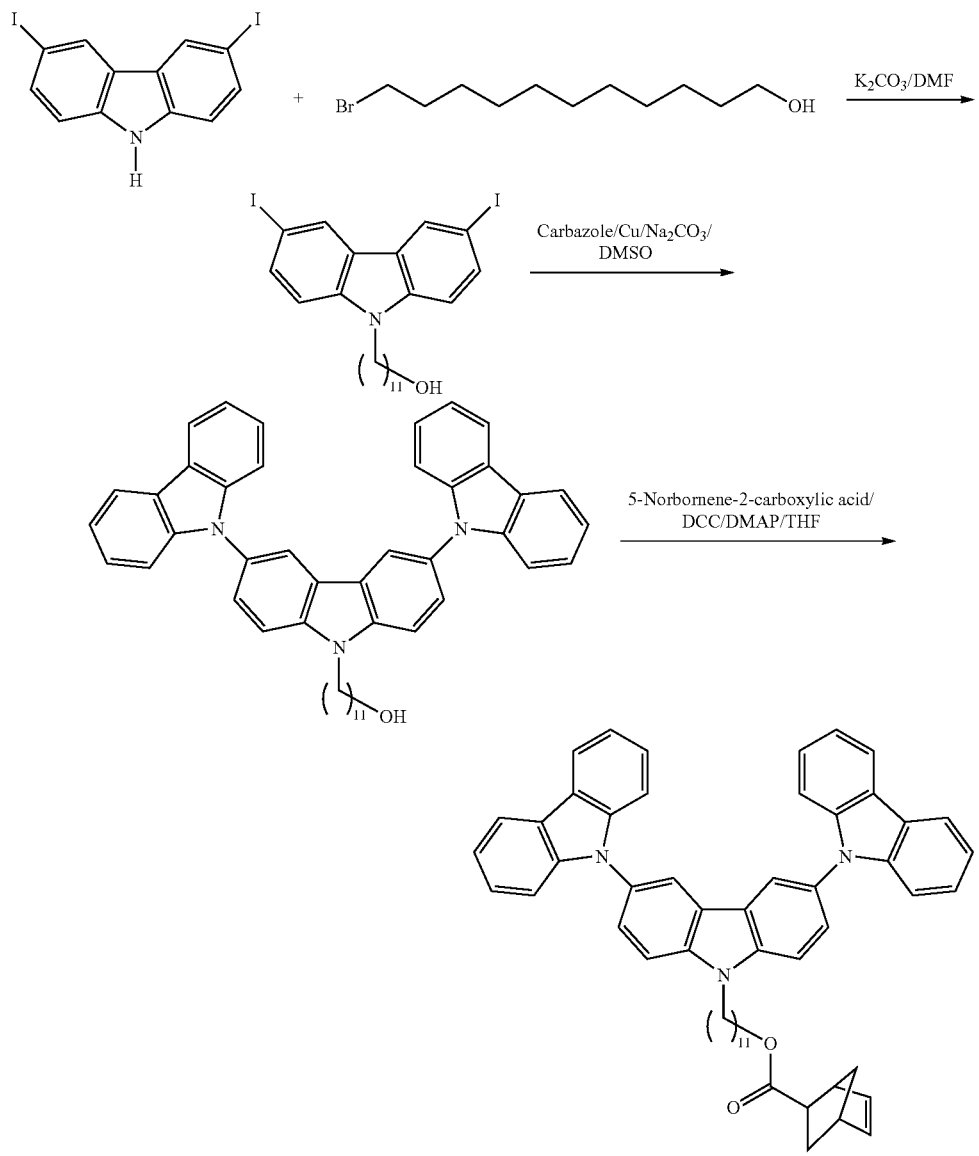

Step 1: 11-(3,6-Diiodo-9H-carbazol-9-yl)undecan-1-ol: To a solution of 3,6-diiodocarbazole (10.0 g, 23.87 mmol) and 11-bromo-1-undecanol (7.0 g, 27.87 mmol) in DMF (100.0 ml) was added K$_2$CO$_3$ (32.0 g, 231.33 mmol). The reaction was carried out at room temperature for 24 h. Water (300 ml) was added. The precipitate was filtered. The crude product was purified by silica gel column using Hexane/ethyl acetate (7:3) as solvent. 12.4 g (87.9%) of pure product as white solid was obtained. $^1$H-NMR (CDCl$_3$, TMS, 500 MHZ): δ=8.32 (d, 2H$_{arom}$, J=1.5 Hz), 7.71 (dd, 2H$_{arom}$, J$_1$=1.5 Hz, J$_2$=8.5 Hz), 7.16 (dd, 2H$_{arom}$, J$_1$=1.5 Hz, J$_2$=8.5 Hz), 4.21 (t, 2H, NCH$_2$), 3.64 (m, 2H, OCH$_2$), 3.41 (t, 1H, OH), 1.81 (m, 4H, 2×CH$_2$), 1.54 (m, 4H, 2×CH$_2$), 1.30 (m, 10H, 5×CH$_2$) ppm.

Step 2: 11-(6-(9H-Carbazol-9-yl)-9H-3,9'-bicarbazol-9-yl)undecan-1-ol: To a solution of 11-(3,6-Diiodo-9H-carbazol-9-yl)undecan-1-ol (8.0 g, 13.6 mmol), carbazole (6.8 g, 40.7 mmol) in DMSO (50.0 ml) were added Cu (10.0 g, 157.38 mmol) and Na$_2$CO$_3$ (30.0 g, 283.05 mmol). The reaction was stirred at 180° C. for 12 h. Insoluble inorganic salts were removed by filtration and washed with THF. After removal of THF, water (250.0 ml) was added. The precipitate was collected by filtration and purified by silica gel column using toluene/ethyl acetate (7:3) as solvent. 8.1 g (91.0%) of product was obtained as white solid. $^1$H (300 MHz, CDCl$_3$): δ8.13-8.24 (m, 5H), 7.63-7.71 (m, 4H), 7.22-7.43 (m, 13H), 4.49 (t, J=6.98 Hz, 2H), 3.62 (t, J=6.34 Hz, 2H), 2.05 (p, J=7.28 Hz, 2H), 1.23-1.77 (m, 18H), 1.18 (s, 1H). $^{13}$C{$^1$H}

(75 MHz, CDCl$_3$): δ142.09, 140.42, 129.54, 126.19, 126.08, 123.62, 123.35, 123.33, 120.51, 120.07, 119.85, 110.34, 109.97, 63.31, 43.94, 33.02, 29.82, 29.79, 29.71, 29.66, 29.43, 27.66, 25.98. ELMS (m/z): M' calcd for C$_{47}$H$_{45}$N$_3$O, 667.36. found 667.4. Elemental Analysis Calculated for C$_{47}$H$_{45}$N$_3$O: C, 84.52; H, 6.79; N, 6.29. Found: C, 84.37; H, 6.74; N, 6.29.

Step 3: 11-(6-(9H-carbazol-9-yl)-9H-3,9'-bicarbazol-9-yl) undecyl bicyclo[2.2.1]hept-5-ene-2-carboxylate: The purified product of prepared in step 2, (0.501 g, 0.75 mmol), 5-norbornene-2-carboxylic acid (0.235 g, 1.70 mmol) and 10 mL of dry THF were combined in a round bottom flask (with stirring) and cooled in an ice bath for 20 minutes. DCC (0.17 g, 0.82 mmol) and DMAP (0.02 g, 0.16 mmol) were weighed (on weighing paper) and added to the reaction flask. The flask was subsequently removed from the ice bath and allowed to warm to room temperature. The reaction proceeded overnight for 18 hours. The TLC showed the presence of starting material the next day, therefore more DCC (0.10 g, 0.48 mmol) was added to the reaction flask. After about 4 hours, TLC still showed the presence of the starting material. Additional 5-norbornene-2-carboxylic acid (0.02 g, 0.14 mmol) and DCC (0.04 g, 0.19 mmol) was added to the flask and the reaction was allowed to proceed overnight for 18 hours. TLC still showed the presence of starting material the next day so the reaction was stopped. The reaction mixture was filtered to remove the insoluble DCC by-product and the filtrate was rotovapped to give white precipitate. The precipitate was recrystallized (2 times) from acetone with methanol but the starting material impurity remained (as observed by TLC). Column chromatography (silica gel, hexanes:ethyl acetate=8:2) was used to purify the product followed by recrystallization from acetone with methanol and vacuum drying overnight. Solvent contamination (as observed by $^1$H NMR) required additional recrystallization from dichloromethane with methanol. The purified product was collected by vacuum filtration and dried overnight at 60° C. in a vacuum oven (for 16 hours) to give a white powder (0.42 g, 71.2%). $^1$H (300 MHz, CDCl$_3$): δ1.22-1.69 (m, 18H), 1.83-1.96 (m, 1H), 2.05 (p, J=7.4 Hz, 2H), 2.17-2.25 (m, 1H), 2.86-2.98 (m, 1H), 3.03 (s, 1H), 3.19 (s, 1H), 5.88-5.94 (m, 1H), 6.07-6.22 (m, 1H), 7.16-7.50 (m, 13H), 7.66 (m, 4H), 8.13-8.24 (m, 5H). $^{13}$C {$^1$H} (75 MHz, CDCl$_3$): δ 175.11, 142.10, 138.29, 137.99, 132.59, 129.53, 126.20, 126.08, 126.06, 123.35, 123.33, 120.54, 120.52, 119.85, 110.34, 109.94, 64.55, 49.86, 45.96, 43.60, 42.77, 29.80, 29.76, 29.74, 29.48, 29.46, 29.44, 29.40, 28.91, 27.69, 26.19. EI-MS (m/z): M$^+$ calcd for C$_{55}$H$_{53}$N$_3$O$_2$, 787.41. found 787.4. Elemental analysis calculated. for C$_{55}$H$_{53}$N$_3$O$_2$: C, 83.83; H, 6.78; N, 5.33. Found: C, 83.70; H, 6.72; N, 5.28.

Synthesis of di-Oxadiazole Monomer 243-(Bicyclo [2,2,1]hept-5en-2-ylmethoxy)phenyl)-5-(3-(5-(4-tert-butylphenyl)-1,3,4-oxadiazol-2-yl)phenyl)-1,3,4-oxadiazole The following synthesis and similar syntheses of similar monomers comprising oxadiazole groups linked to norbornenyl groups has been previously reported in PCT Application Serial No. PCT/EP/2008 068119 filed 19 Dec. 2008, the disclosures of which are hereby incorporated herein by reference.

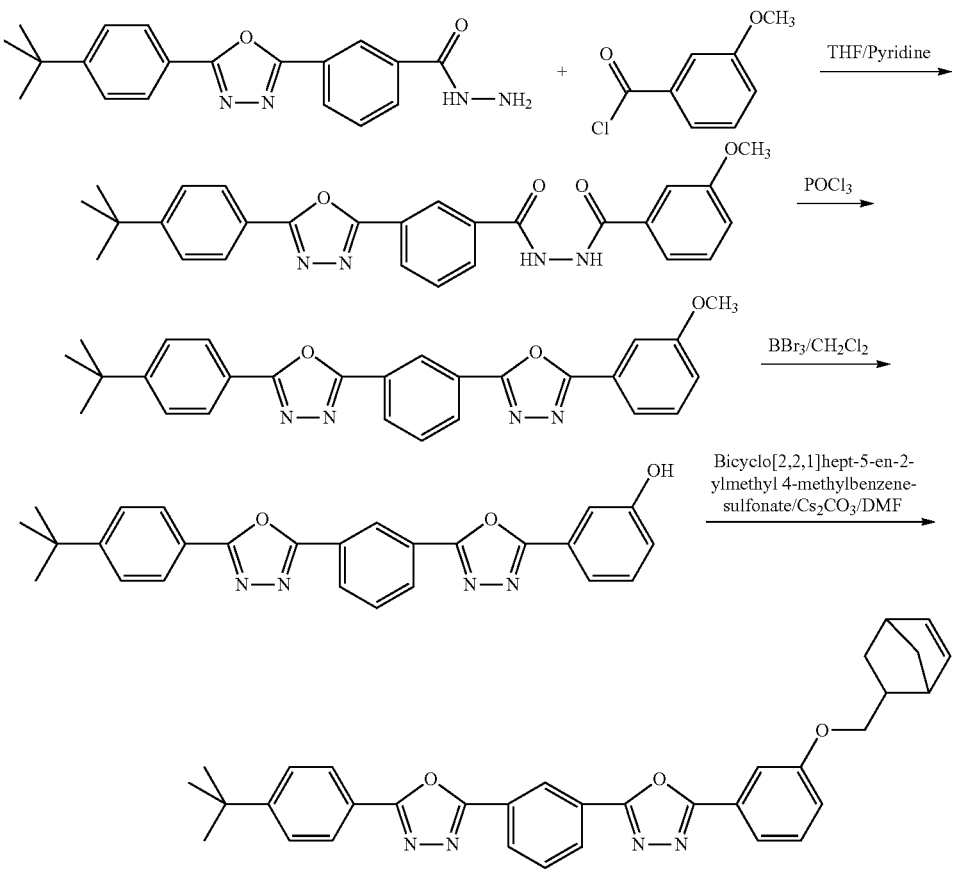

Step 1: 3-(5-(4-tert-butylphenyl)-1,3,4-oxadiazol-2-yl)-N'-(3-methyoxybenzoyl)benzohydrazine: To a solution of 3-(5-(4-tert-butylphenyl)-1,3,4-oxadiazol-2-yl)benzohydrazine (1.5 g, 4.46 mmol) in dry tetrahydrofuran (50.0 ml) and DMF (5.0 ml), was slowly added 3-methoxybenzoyl chloride (0.8 g, 4.69 mmol) at room temperature under nitrogen. During addition of 3-methoxybenzoyl chloride, white solids appeared. The reaction mixture was stirred at room temperature for 21 hours and then pyridine (10.0 ml) was added and stirred for another hour. Then, water (300.0 ml) was added into the reaction mixture. The white solid was collected by filtration and dried overnight under vacuum and provided 1.9 g (90.4%) yield. $^1$H NMR (400 MHz, DMSO-$d_6$) δ: 10.83 (s, br, 1H, NH), 10.64 (s, br, NH), 8.66 (s, 1H), 8.34 (d, 1H, J=7.6 Hz), 8.17 (d, 1H, J=7.6 Hz), 8.07 (d, 2H, J=8.0 Hz), 7.80 (t, 1H, J=7.6 Hz), 7.65 (d, 2H, J=8.0 Hz), 7.54-7.43 (m, 3H), 7.17 (d, 1H, J=8.0 Hz), 3.83 (s, 3H, OCH$_3$), 1.33 (s, 9H, 3×CH$_3$) ppm.

Step 2: 2-(4-tert-Butylphenyl)-5-(3-(5-(3-methoxyphenyl)-1,3,4-oxadiazol-2-yl)phenyl)-1,3,4-oxadiazole: 3-(5-(4-tert-Butylphenyl)-1,3,4-oxadiazol-2-yl)-N'-(3-methyoxybenzoyl)benzohydrazine (1.75 g, 3.72 mmol) was added in POCl$_3$ (15.0 ml). The reaction was heated to 90° C. and kept at this temperature for 4 hours. After cooling down to room temperature, the reaction mixture was slowly dropped into ice-water (300.0 ml). The white solid formed was collected by vacuum filtration. The crude product was dried and purified by a silica gel column using dichloromethane/ethyl acetate, ratio (9:1), as the eluent. After the removal of the solvents, a pure white solid product was obtained in 1.18 g (70.2%) yield, $^1$H NMR (400 MHz, CDCl$_3$) δ: 8.86 (t, 1H, J=1.6 Hz), 8.34 (dt, 2H, $J_1$=7.6 Hz, $J_2$=1.6 Hz), 8.11 (d, 2H, J=8.4 Hz), 7.73 (m, 3H), 7.57 (d, 2H, J=8.4 Hz), 7.47 (t, 1H, J=7.6 Hz), 7.32 (dd, 1H, $J_1$=7.6 Hz, $J_2$=1.6 Hz), 3.93 (s, 3H, OCH$_3$), 1.39 (s, 911, 3×CH$_3$) ppm. $^{13}$C NMR (100 MHz, CDCl$_3$) δ: 165.11, 164.94, 163.62, 163.34, 159.95, 155.64, 130.26, 129.97, 129.74, 126.89, 126.10, 125.10, 124.92, 124.90, 124.65, 120.70, 119.42, 118.42, 111.60, 55.56, 35.10, 31.08 ppm. MS-EI (m/z): [M]$^+$ calcd for C$_{28}$H$_{24}$N$_4$O$_4$ 452.2. found 452.2.

Step 3: 3-(5-(3-(5-(4-tert-Butylphenyl)-1,3,4-oxadiazol-2-yl)phenyl)-1,3,4-oxadiazol-2-yl)phenol (YZ-I-269): To a solution of 2-(4-tert-Butylphenyl)-5-(3-(5-(3-methoxyphenyl)-1,3,4-oxadiazol-2-yl)phenyl)-1,3,4-oxadiazole (1.0 g, 2.21 mmol) in dichloromethane (30.0 ml), was dropwise added BBr$_3$ (16.0 ml, 1M in dichloromethane) at -78° C. (dry-ice/acetone) under nitrogen. After the addition of the BBr$_3$ solution, the reaction was taken to room temperature and kept at room temperature for 7 hours. The reaction mixture was poured into ice-water (150.0 ml). Dichloromethane was evaporated under reduced pressure. The white solid was collected by filtration. After drying under vacuum, a white solid product was obtained in 0.98 g (100%) yield. δ: 10.02 (s, 1H), 8.68 (s, 1H), 8.31 (m, 2H), 8.07 (d, 2H, J=8.4 Hz), 7.86 (t, 1H, J=8.0 Hz), 7.63 (d, 2H, J=8.4 Hz), 7.58 (d, 1H, J=7.6 Hz), 7.53 (s, 1H), 7.42 (t, 1H, J=7.6 Hz), 7.03 (dd, 1H, $J_1$=7.6 Hz, $J_2$=1.6 Hz), 1.32 (s, 9H, 3×CH$_3$) ppm.

Step 4: 2-(3-(Bicyclo[2,2,1]hept-5en-2-ylmethoxy)phenyl)-5-(3-(5-(4-tert-butylphenyl)-1,3,4-oxadiazol-2-yl)phenyl)-1,3,4-oxadiazole: To a solution of 3-(5-(3-(5-(4-tert-butylphenyl)-1,3,4-oxadiazol-2-yl)phenyl)-1,3,4-oxadiazol-2-yl)phenol (0.92 g, 2.10 mmol) and bicyclo[2,2,1]hept-5-en-2-ylmethyl 4-methylbenzenesulfonate (1.6 g, 5.75 mmol) in DMF (45.0 ml), was added Cs$_2$CO$_3$ (4.5 g, 13.81 mmol) at room temperature under nitrogen. The reaction was carried out at 100° C. for 2 hours. After cooling down to room temperature, water (100.0 ml) was added into the reaction mixture. A brown solid precipitate was collected by filtration and washed with methanol and then dried under vacuum. The crude product was purified by a silica gel column using dichloromethane/ethyl acetate, ratio (9.3:0.7), as the eluent. After removal of the solvents, a pure white solid product was obtained in 0.97 g (85.1%) yield by recrystallization from dichloromethane/methanol. $^1$H NMR (400 MHz, CDCl$_3$) δ: 8.86 (m, 1H), 8.34 (dd, 2H, $J_1$=8.0 Hz, $J_2$=1.6 Hz), 8.11 (d, 2H, J=8.4 Hz), 7.73 (m, 2H), 7.67 (m, 1H), 7.58 (d, 2H, J=8.4 Hz), 7.45 (m, 1H), 7.12 (m, 1H), 6.22-5.99 (m, 2H, C=C—H, endo and exo), 4.17-3.64 (m, 2H, OCH$_2$, endo and exo), 3.09 (s, br), 2.91 (m, br), 2.61 (m, br), 1.95 (m), 1.52 (m), 1.39 (s, 9H, 3×CH$_3$), 1.40-1.23 (m), 0.68 (m) ppm. $^{13}$C NMR (100 MHz, CDCl$_3$) δ: 165.14, 163.65, 163.38, 159.57, 155.67, 137.68, 136.90, 136.38, 132.29, 130.26, 129.99, 129.77, 129.71, 126.92, 126.13, 125.13, 124.98, 124.94, 124.61, 120.73, 119.31, 119.22, 118.90, 112.29, 72.57, 71.78, 49.42, 45.06, 43.87, 43.69, 42.23, 41.60, 38.54, 38.32, 35.12, 31.10, 29.62, 28.99 ppm. MS (m/z): [M+1]$^+$ calcd for C$_{34}$H$_{32}$N$_4$O$_3$ 545.3. found 545.2. Anal. Calcd for C$_{34}$H$_{32}$N$_4$O$_3$: C, 74.98; H, 5.92; N, 10.29. Found: C, 74.77; H, 6.02; N, 10.27.

Copolymerization of Norbornenyl Tricarbazole and Norbornenyl Dioxadiazole Monomers to Form Class (IV) Copolymer—

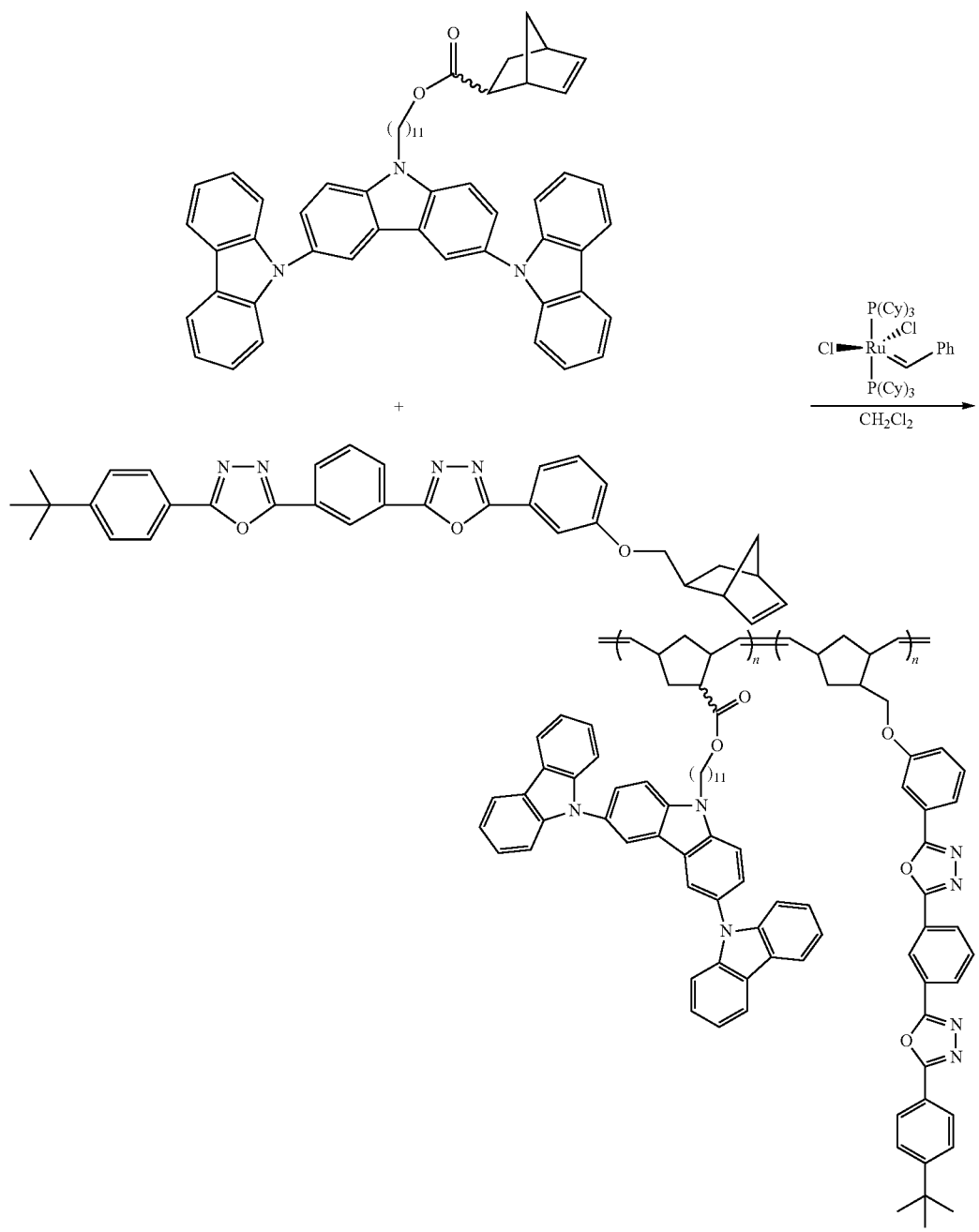

2-(3-(Bicyclo[2,2,1]hept-5en-2-ylmethoxy)phenyl)-5-(3-(5-(4-tert-butylphenyl)-1,3,4-oxadiazol-2-yl)phenyl)-1,3,4-oxadiazole monomer (0.201 g, 0.37 mmol) and 11-(6-(9H-carbazol-9-yl)-9H-3,9'-bicarbazol-9-yl)undecyl bicyclo[2.2.1]hept-5-ene-2-carboxylate monomer (0.288 g, 0.37 mmol) were weighed into a bottle. Grubbs' first generation catalyst (0.0076 g, 9.2×10$^{-3}$ mmol) was weighed out into separate vial. The bottle and vial were placed into a glovebox. 6.0 mL of dry $CH_2Cl_2$ was added to the bottle containing the monomers. 1.0 mL of dry $CH_2Cl_2$ was added to vial containing Grubbs' first generation catalyst and solution was quickly added to monomer solution. An additional 1.0 mL of $CH_2Cl_2$ was added to catalyst vial (for washing) and solution was transferred into the monomer bottle. The polymerization was allowed to proceed overnight for 20 hours. The reaction mixture was concentrated (under vacuum) and quenched (out of glovebox) with 3.0 mL of ethyl vinyl ether and then transferred (dropwise) into 40.0 mL of methanol to precipitate polymer. The polymer was then vacuum filtered and re-dissolved with minimal (<3.0 mL) $CH_2Cl_2$. The solution was then added (dropwise) to 30.0 mL of methanol to precipitate polymer. Process of isolating, dissolving, and vacuum filtering polymer repeated three more repetitions in order to purify polymer. Final product was dried under vacuum to give a white/off-white powder (0.261 g, 53.4%). $^1H$ (300 MHz, $CDCl_3$): δ8.66-8.83 (br, 1H), 7.94-8.29 (br, 6H), 7.44-7.74 (br, 6H), 6.91-7.44 (br, 13H), 5.08-5.47 (br, 2H), 4.24-4.51 (br, 2H), 3.67-4.08 (br, 4H), 1.82-3.23 (br, 7H), 1.00-1.82 (br, 27H). Elemental anal. calcd., 79.41; H, 6.35; N, 7.81. Found: C, 78.74; H, 6.43; N, 7.24. Gel Permeation Chromatography (THF): $M_w$=261,000; $M_n$=68,000; PDI=3.813.

Example 5

OLED Devices Comprising Homopolymers of Ambipolar Monomers

Multi-layer OLED devices were prepared as generally described below, using solutions of the ambiopolar homopolymers described herein and a known monomeric phosphorescent Iridium complex to form the emission layer of the OLED devices, as further described below.

In examples employing ambipolar homopolers of class (I), (II), or (III), 35 nm thick hole injection and hole transporting layer of Poly-TPD-F was typically formed by spin coating on a pre-cleaned ITO substrate, then, this hole transporting layer was photo-crosslinked. On the top of crosslinked hole transporting layer, a 40 nm thick emission layer of one of the ambipolar polymers described herein was doped with 10 wt % Ir(ppy)$_3$ and coated by spin coating. Then, the emitting layer was capped with a 40 nm thick layer of BCP used as hole blocking and electron transporting layer by thermally evaporated. Finally, 2.5 nm of LiF as an electron-injection layer and a 200 nm-thick aluminum cathode were vacuum deposited on the top of BCP.

For the hole-transport layer, 10 mg of Poly-TPD-F was dissolved in 1.0 ml of distilled and degassed toluene. For the emissive layer, three individual solutions of the ambipolar methacrylate homopolymers Poly(2-(3-(5-(4-carbazol-9-ylphenyl)-1,3,4-oxadiazol-2-yl)phenoxy)ethyl methacrylate), i.e. "Ambi-Polymer 1"; Poly(2-(3-(5-(3-Carbazol-9-ylphenyl)-1,3,4-oxadiazol-2-yl)phenoxy)ethyl methacrylate), i.e. "Ambi-Polymer 2"; and Poly(2-(3-(5-(3,5-Dicarbazol-9-ylphenyl)-1,3,4-oxadiazol-2-yl)phenoxy) ethyl methacrylate)), i.e. "Ambi-Polymer 3"; were prepared by dissolving 9.4 mg of the polymers and 0.6 mg of fac tris(2-phenylpyridinato-N,C2') iridium [Ir(ppy)$_3$] in 1.0 ml of distilled and degassed chlorobenzene. All solutions were made under inert atmosphere and were stirred overnight.

35 nm thick films of the hole-transport material were spin coated (60 s at 1500 rpm, acceleration 10,000) onto air plasma treated indium tin oxide (ITO) coated glass substrates with a sheet resistance of 20Ω/□ (Colorado Concept Coatings, L.L.C.). Films were photo-crosslinked with a standard broadband UV light with a 0.7 mW/cm$^2$ power density for 1.0 minute. Subsequently, a 40 nm-thick film of ambipolar polymer doped 6.0% (ratio in weight) of green phosphorescent compound (Ir(ppy)$_3$) was spin coated from its solution on top of the crosslinked hole-transport layer (60 s at 1000 rpm, acceleration 10,000). For the hole-blocking layer, bathocuproine (2,9-dimethyl-4,7-diphenyl-1,10-phenanthroline, BCP) was first purified using gradient zone sublimation, and a film of 40 nm was then thermally evaporated at a rate of 0.4 Å/s and at a pressure below 1×10$^{-7}$ Torr on top of the emissive layer.

Finally, 2.5 nm of lithium fluoride (LiF) as an electron-injection layer and a 200 nm-thick aluminum cathode were vacuum deposited at a pressure below 1×10$^{-6}$ Ton and at rates of 0.1 Å/s and 2 Å/s, respectively. A shadow mask was used for the evaporation of the metal to form five devices with an area of 0.1 cm$^2$ per substrate. At no point during fabrication were the devices exposed to atmospheric conditions. The testing was done right after the deposition of the metal cathode in inert atmosphere without exposing the devices to air.

Figure 12:
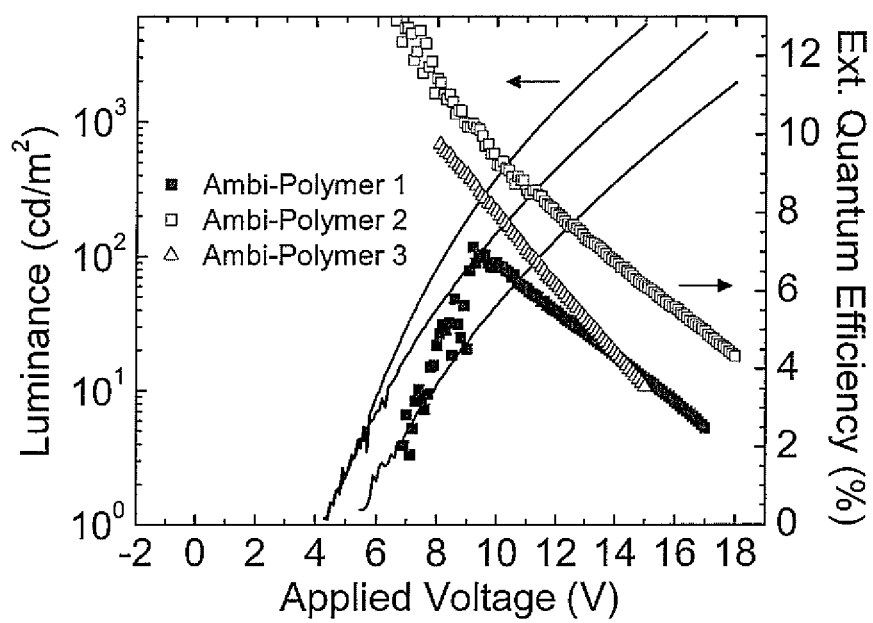
FIG. 12 shows the luminescence and external quantum efficiency versus voltage performance of OLED devices having emissive layers comprising three ambipolar polymers of class (II) as a host material and a phosphorescent Iridium complex as a guest. See Example 5.

Comparison of Ambipolar Homopolymers as Hosts:

FIG. 12 shows the luminance vs. applied voltage and external quantum efficiency vs. applied voltage characteristics for three ambipolar polymers, Ambi-Polymer 1, Ambi-Polymer 2, and Ambi-Polymer 3. Devices with Ambi-Polymer 1 and Ambi-Polymer 1 show low turn-on voltage ~4.5 V, and device with Ambi-Polymer 2 has turn-on voltage ~5.5 V. The external quantum efficiency obtained in the devices were ~10% for Ambi-Polymer 3 at 100 cd/m$^2$, ~9% for Ambi-Polymer 2 at 100 cd/m$^2$ and ~7% for Ambi-Polymer 1 at 100 cd/m$^2$. The luminance of the all devices can achieved over several thousand cd/m$^2$. Based on turn-on voltage, luminance and external quantum efficiency data, Ambi-Polymer 3 arguably gave the best performance among these three host polymers.

Comparison of OLED Devices Comprising Ambi-Polymer 3 with Known Mixed Hole Carrying and Electron Carrying Hosts:

Our previous best OLED devices employed emissive layer host materials comprising the PVK polycarbazole hole carrier, doped with 30% or more of PBD or OXD-7 as small molecule electron carriers, as well as small molecule 3rd row transition metal complexes as phosphorescent guests.

Figure 13:
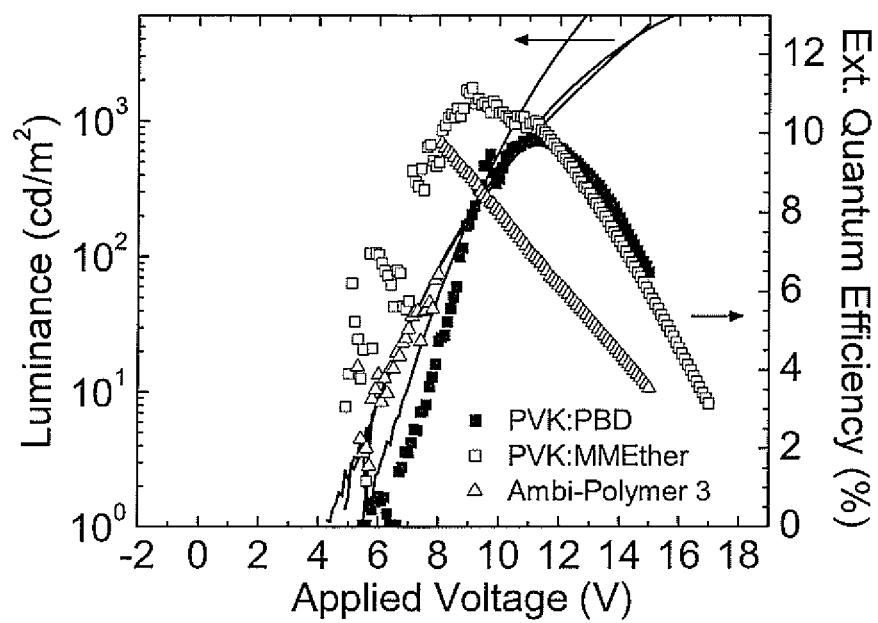
FIG. 13 compares the luminescence and external quantum efficiency versus voltage performance of OLED devices having emissive layers comprising an ambipolar polymer of class (II) as a host material with OLED devices with two alternative host materials comprising mixtures of hole and electron carrying materials. See Example 5.

FIG. 13 compares the results of the OLED device comprising the results of a comparison of the results obtained using the Ambi-Polymer 3 with devices employing a mixture of PVK:PBD, or a mixture of PVK:MMEther, where MMEther is polyoxadiazole having the structure shown below:

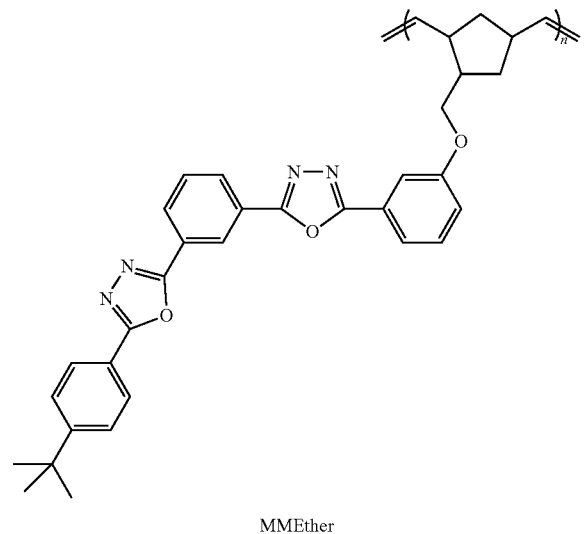

MMEther

The OLED device employing Ambi-Polymer 3 gave results comparable to the two devices based on mixed host materials, but is likely to be much more stable under heating and/or long-term use.

Figure 14:
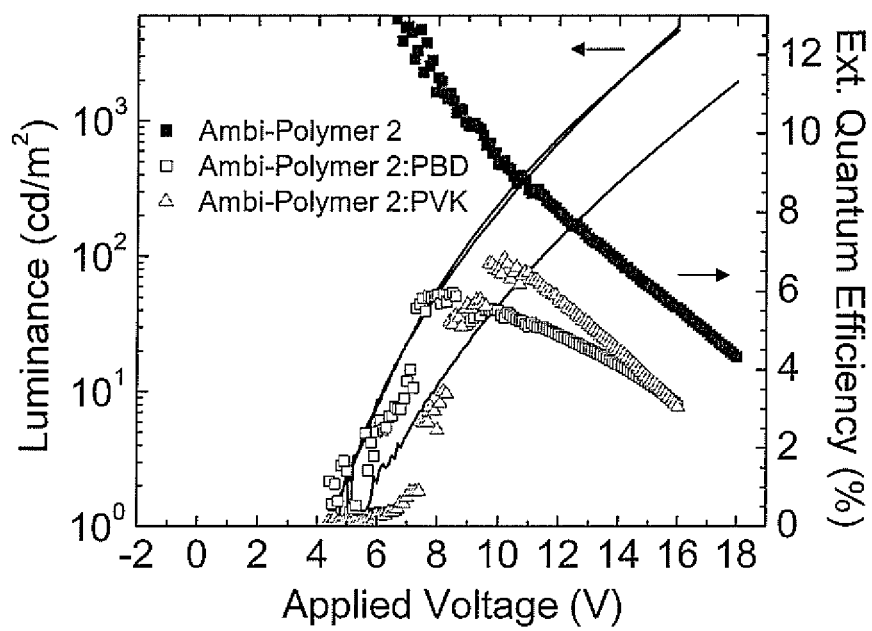
FIG. 14 shows compares the luminescence and external quantum efficiency versus voltage performance of OLED devices having emissive layers comprising one of the ambipolar polymers of class (II) described herein as a host material with OLED devices employing two alternative host materials that also comprise added hole or electron carrying materials. See Example 5.

Effect of Addition of Additional Hole or Electron Carriers on OLED Devices Comprising Ambi-Polymer 2:

FIG. 14 shows that addition of additional hole carrier materials (PVK) or electron carrier materials (PBD) decreased the performance of OLED devices comprising Ambi-Polymer 2.

Example 6

OLED Device Comprising an Ambipolar Copolymer of Class (IV)

An OLED device was fabricated using an ambipolar copolymer host of class (IV) having the structure shown below, to form the emission layer.

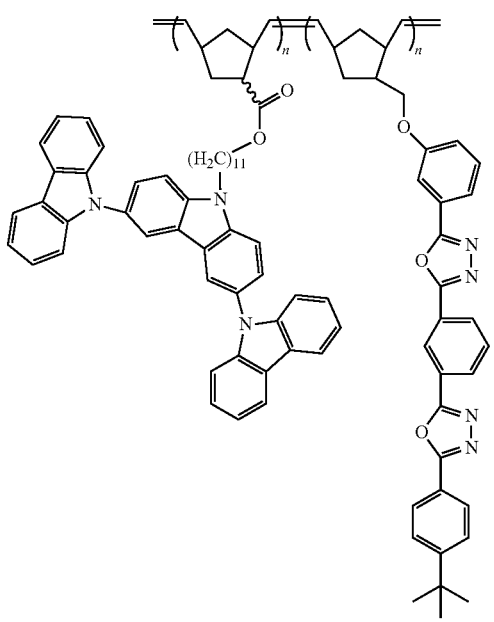

The general experimental details for the device fabrication were described earlier above. For the emissive layer, a 50 nm layer was spin coated from a solution of chlorobenzene (10 mg/ml) using the ambipolar host copolymer indicated above and the previously known F—Pt emitter complex (structure shown below) in a weight ratio of 9:1.

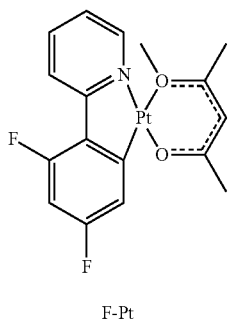

F-Pt

Figure 15A:
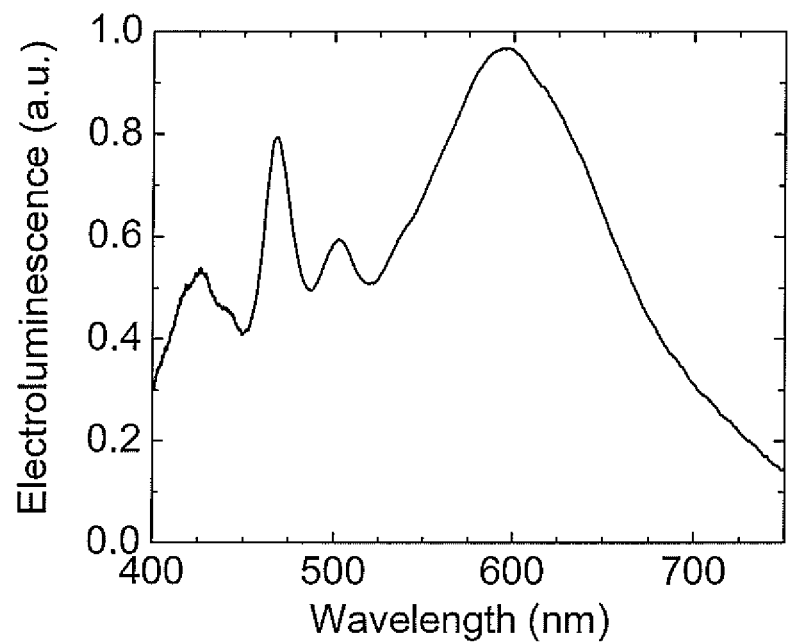
FIG. 15a shows the electroluminescence spectrum of an OLED device comprising an ambipolar copolymer of class (1V) as described in Example 4.
Figure 15B:
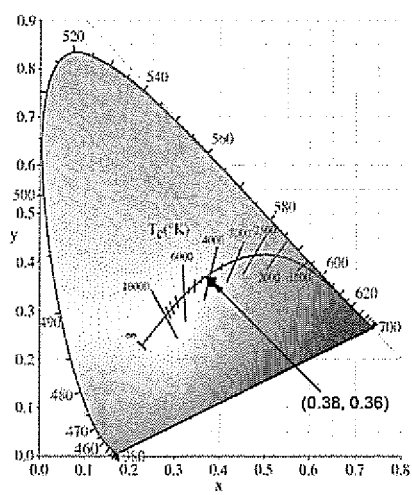
FIG. 15b shows a CIE diagram of the emission from the OLED device of FIG. 15a that shows that the light emitted from the OLED is almost white. See Example 6.

The Electroluminescence spectrum of the OLED device utilizing the ambipolar polymer is shown in FIG. 15a. The EL spectrum of the OLED showed the emissions across the entire visible spectrum, which gave CIE coordinates in the near-white region and a high CRI of 90. The CIE coordinates for the WOLED device are shown in FIG. 15b, as indicated by the arrow on the color coordinate diagram. It can be seen that the observed CIE coordinate of (0.38, 0.36) is close to a white color coordinate (0.33, 0.33). It is also worth noting here that this level of white emission was achieved using less FPt dopant, 10% (by weight percent), than earlier devices employing only hole transport homopolymers requiring around 18% doping levels for near white emission.

Figure 16A:
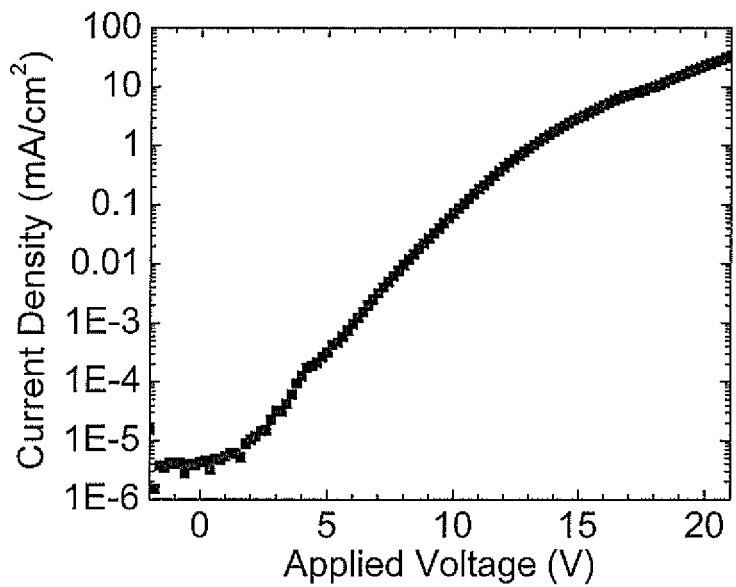
FIG. 16a shows the luminescence and external quantum efficiency versus voltage performance of OLED devices having emissive layers comprising an ambipolar copolymer of class (IV) as a host material and a phosphorescent platinum complex as a guest. See Example 6.
Figure 16B:
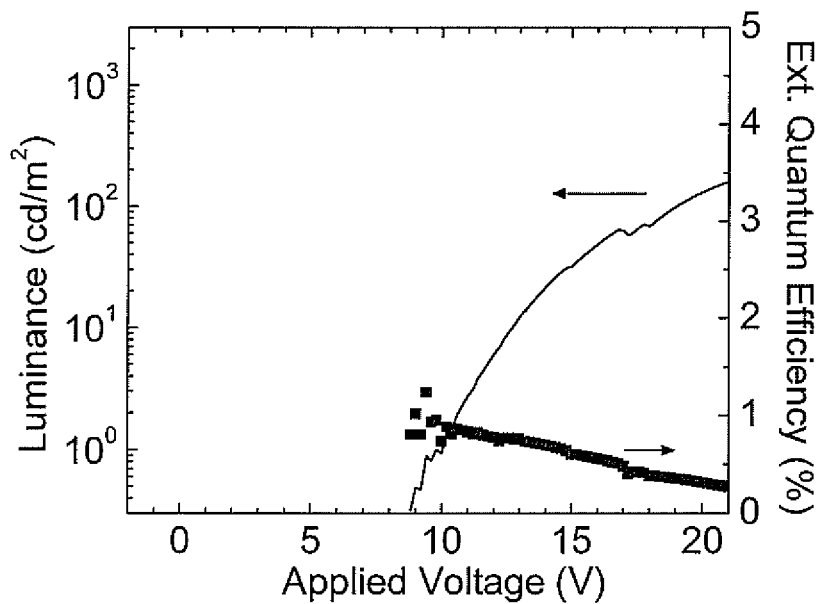

The current density-voltage (J-V) characteristics for the WOLEDs with the ambipolar host are shown in FIG. 16a. The luminance and EQE curves for the respective devices are shown in FIG. 16b. With respect to efficiency, the WOLED device showed an EQE of 0.3±0.1% (1±1 cd/A)

Example 7

OLED Device Comprising an Ambipolar Small Molecule Hole and Electron Carrier

An OLED device was fabricated using the small molecule ambipolar compound 2-(3,5-Dicarbazol-9-ylphenyl)-5-(3-methoxyphenyl)-1,3,4-oxadiazole, whose synthesis is detailed in Example 1, and the known phosphorescent Iridium complex Ir(ppy)$_3$ (to form the emission layer).

For the hole-transport layer, 10 mg of PVK were dissolved in 1 ml of distilled and degassed toluene. 35 nm thick films of the hole-transport material were spin coated (60 s@1500 rpm, acceleration 10,000) onto air plasma treated indium tin oxide (ITO) coated glass substrates with a sheet resistance of 20 Ω/square (Colorado Concept Coatings, L.L.C.). For the emitting layer, a concentration of 6% Ir(ppy)$_3$ was coevaporated into a 20-nm-thick film of 2-(3,5-Dicarbazol-9-ylphenyl)-5-(3-methoxyphenyl)-1,3,4-oxadiazole. For the hole-blocking and electron transport layer, BCP was vacuum deposited at a pressure below $1 \times 10^{-6}$ Torr and at rates of 0.4 Å/s, respectively. Finally, 2.5 nm of lithium fluoride (LiF) as an electron-injection layer and a 200 nm-thick aluminum cathode were vacuum deposited at a pressure below $1 \times 10^{-6}$ Torr and at rates of 0.1 Å/s and 2 Å/s, respectively. A shadow mask was used for the evaporation of the metal to form five devices with an area of 0.1 cm$^2$ per substrate. The testing was done right after the deposition of the metal cathode in inert atmosphere without exposing the devices to air.

Figure 17A:
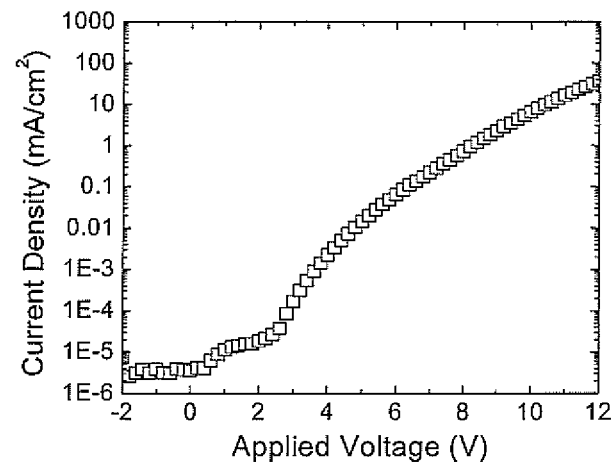
FIG. 17a shows the current density versus voltage characteristics of an OLED device comprising an emissive layer comprising 2-(3,5-Dicarbazol-9-ylphenyl)-5-(3-methoxyphenyl)-1,3,4-oxadiazole as a hole and electron carrying host and Ir(ppy)$_3$ as an emissive guest, as described in Example 7.
Figure 17B:
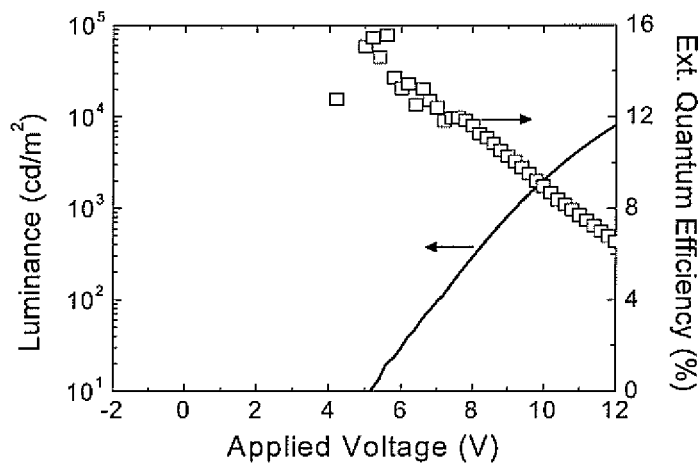
FIG. 17b shows the luminescence and external quantum efficiency versus voltage performance of the OLED device.

The current-voltage characteristic of the above referenced device is shown in FIG. 17a. The light output and external quantum efficiency as a function of voltage are shown in FIG. 17b. The device referenced above exhibits an external quantum efficiency of 12.4% and 10.1% at a light output level of 100 cd/m$^2$ and 1,000 cd/m$^2$, respectively.

Figure 18A:
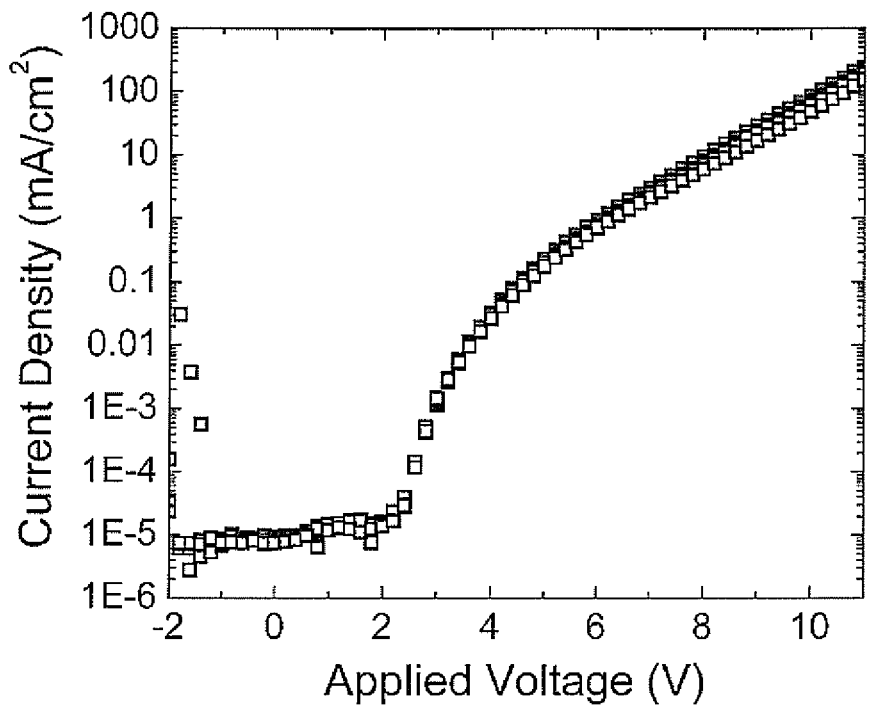
Figure 18B:
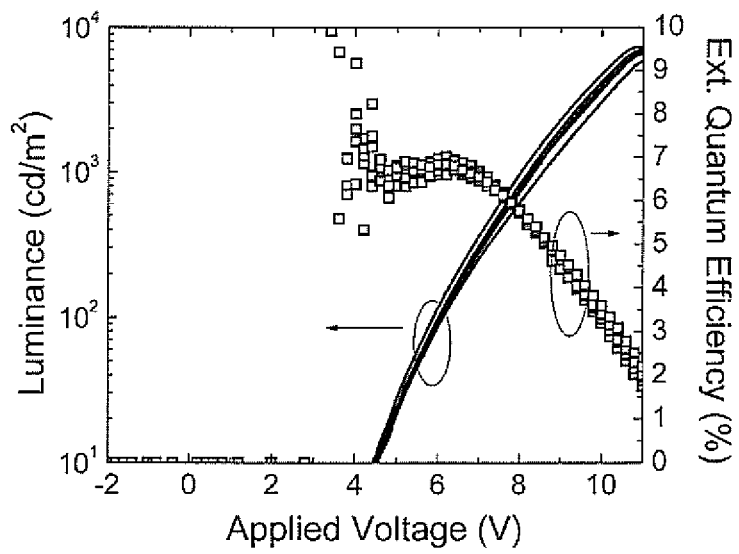
FIG. 18b shows the luminescence and external quantum efficiency versus voltage performance of the OLED device.
Figure 20:
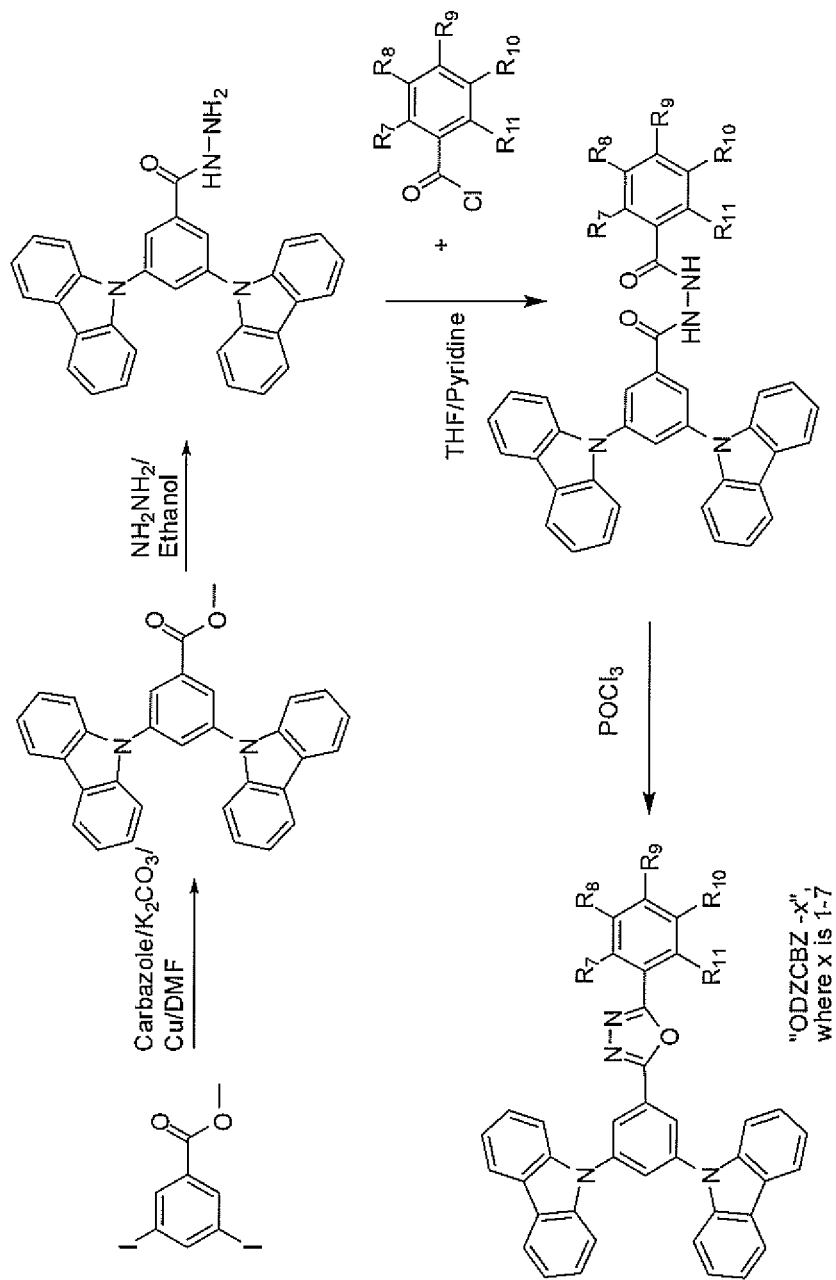

Additional otherwise similar OLED devices, instead utilizing a 6% dispersion of the well known blue-green emitter iridium (III)bis[(4,6-di-fluorophenyl)-pyridinato-N,C2']picolinate (FIrpic), coevaporated into 2-(3,5-Dicarbazol-9-ylphenyl)-5-(3-methoxyphenyl)-1,3,4-oxadiazole, to supply the emitting layer, together with either PVK or TCZ as hole transport layers were also constructed (five devices each) and tested as already described. The current-voltage characteristic of the PVK devices are shown in FIG. 18a, and the light output and external quantum efficiency as a function of voltage are shown in FIG. 18b. The current-voltage characteristic of the PVK devices are shown in FIG. 19a, and the light output and external quantum efficiency as a function of voltage are shown in FIG. 19b Example 7a Synthesis and Characterization of a Series of 2-(3,5-Dicarbazol-9-ylphenyl)-5-(substituted-phenyl)-1,3,4-oxadiazoles In order to serve as a suitable host material for various emitter complexes with a variety of emission wavelengths, the energies of the lowest triplet states LUMO orbitals of the oxadiazolecarbazoles ("ODZCBZs") disclosed herein, as already exemplified by 2-(3,5-Dicarbazol-9-ylphenyl)-5-(3-methoxyphenyl)-1,3,4-oxadiazole as described in Example 7 above, should be rationally tunable, so as to properly match with the energies of the various emitter complexes. Accordingly, Applicants synthesized a series of seven variously substituted analogs of 2-(3,5-Dicarbazol-9-ylphenyl)-5-(3-methoxyphenyl)-1,3,4-oxadiazole (i.e. "ODZCBZ-x" compounds, where x is 1-7), as shown in the drawing below, FIG. 20, and in Table 1, shown below.

TABLE 1

The Reduction Potentials of "ODZCBZ-x" Ambipolar Small Molecules

"ODZCBZ-x", where x is 1-7

| No. | $R_7$ | $R_8$ | $R_9$ | $R_{10}$ | $R_{11}$ | $E_{1/2}^{0/-1}$ |
|---|---|---|---|---|---|---|
| ODZCBZ-1 | —F | —F | —F | —F | —F | −2.05 V |
| ODZCBZ-2 | —H | —H | —F | —H | —H | −2.38 V |
| ODZCBZ-3 | —H | —H | —H | —H | —H | −2.37 V |
| ODZCBZ-4 | —H | —H | —CF$_3$ | —H | —H | −1.50 V |
| ODZCBZ-5 | —H | —H | —CH$_3$ | —H | —H | −2.41 V |
| ODZCBZ-6 | —H | —H | —H | —H | —CF$_3$ | −2.25 V |
| ODZCBZ-7 | —H | —H | —H | —CF$_3$ | —H | −2.29 V |

Cyclic voltammetry (CV) measurements for each of the ODZCBZ-x compounds was done in THF with 0.1 M of (n-Bu)$_4$NPF$_6$, with Pt wire counter electrode; Ag/AgCl reference electrode; and 50 mV/s scanning rate, using Ferrocene as an internal standard. The ODZCBZ-x compounds showed reversible reductions at between about −1.5 and −2.5 volts vs ferrocene, at the experimental potentials indicated in Table 1. The presence of strong electron withdrawing substituents (F, CF3) at the para "R$^9$" position seemed to noticeably lower the reduction potentials.

Example 8

Synthesis and Characterization of 2-(3-(6-(9H-carbazol-9-yl)-9H-3,9'-bicarbazol-9-yl)phenyl)-5-(3-methoxyphenyl)-1,3,4-oxadiazole

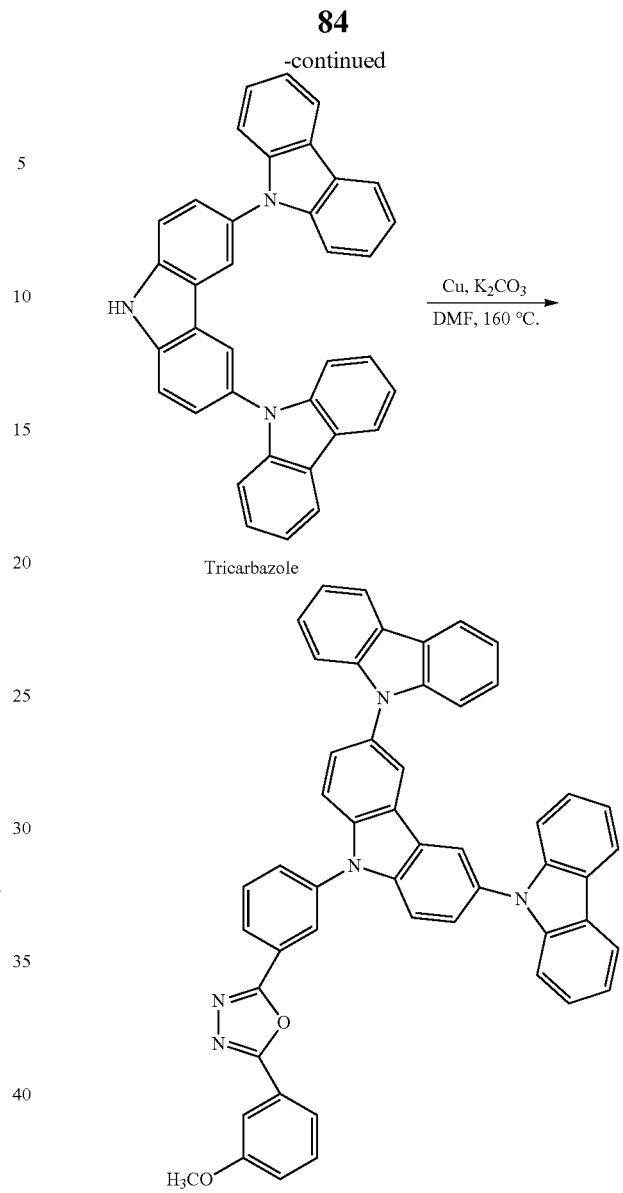

2-(3-iodophenyl)-5-(3-methoxyphenyl)-1,3,4-oxadiazole (1.023 g, 2.82 mmol, see Example 1 for preparation) and Tricarbazole (1.386 g, 2.79 mmol, see Xing et al, Sensors and Actuatord, B 114 (2006) 28-31 for preparation) were added to DMF (25 mL) under N$_2$. Then Cu (1.790 g, 28.17 mmol) and K$_2$CO$_3$ (3.870 g, 28.00 mmol) were added and the reaction mixture heated to 160° C. for 24 hours. The reaction mixture was cooled to room temperature and then poured into THF (150 mL), stirring for 1 h. After filtering off all solids, the filtrate was concentrated by rotary evaporation. Water (100 mL) was then added in to the concentrated filtrate and the crude product precipitated and was collected by filtration. The crude product was then dried and purified by silica gel chromatography (toluene, then toluene:ethyl acetate=9:1). After the chromatography solvents were removed, the product was redissolved and reprecipitated in acetone to give a white solid (0.870 g, 42%), 2-(3-(6-(9H-carbazol-9-yl)-9H-3,9'-bicarbazol-9-yl)phenyl)-5-(3-methoxyphenyl)-1,3,4-oxadiazole.

$^1$H NMR (400 MHz, CDCl$_3$): δ (ppm): 8.52 (t, J=1.6 Hz, br, 1H), 8.35 (dt, J=7.2 Hz, J$_2$=1.6 Hz, br, 1H), 8.29 (d, J=2.0 Hz, 2H), 8.15 (d, J=7.6 Hz, 4H), 7.94 (dt, $J_1$=8.0 Hz, $J_2$=1.6 Hz, br, 1H), 7.91 (q, J=7.6 Hz, 1H), 7.73 (d, J=8.0 Hz, br, 1H), 7.67 (t, J=8.8 Hz, br, 4H), 7.64 (dd, $J_1$=8.8 Hz, $J_2$=2.0 Hz, 1H), 7.45 (t, J=8.0 Hz, 1H), 7.40 (d, J=7.6 Hz, 8H), 7.27 (septet, J=4.0 Hz, 4H), 7.11 (dd, $J_1$=8.0 Hz, $J_2$=2.4 Hz, 1H), 3.90 (s, 3H). $^{13}$C NMR (100 MHz, CDCl$_3$): δ (ppm): 165.03, 163.70, 160.02, 141.68, 140.44, 138.21, 131.26, 130.82, 130.40, 130.34, 126.52, 126.27, 125.92, 125.59, 124.70, 124.21, 123.17, 120.31, 119.86, 119.75, 119.42, 118.37, 111.83, 111.15, 109.65, 99.96. Anal. Calcd. for $C_{51}H_{33}N_5O_2$: C, 81.91; H, 4.45; N, 9.36. Found: C, 81.61; H, 4.25; N, 9.30. ESI-Accurate Mass (m/z): [M$^+$] calcd. for $C_{51}H_{33}N_5O_2$: 747.26, 748.27. found: 748.2759.

UV-Vis (CH$_2$Cl$_2$, r.t.): 342 nm, 293 nm, 238 nm=1.39×10$^5$ mol$^{-1}$·L·cm$^{-1}$), DSC: $T_g$=154° C. TGA: 5% Mass lost at 467° C. CV (vs. Ferrocene): $E_{1/2}^{0/-1}$=−2.5 V (THF, r.t.), $E_{1/2}^{0/+1}$=0.53 V (CH$_2$Cl$_2$, r.t.), $E_{1/2}^{+1/+2}$=0.77 V (CH$_2$Cl$_2$, r.t.)

OLED devices comprising emissive layers comprising 6% Ir(ppy) co-deposited with the 2-(3-(6-(9H-carbazol-9-yl)-9H-3,9'-bicarbazol-9-yl)phenyl)-5-(3-methoxyphenyl)-1,3,4-oxadiazole were made via the same procedures already described to make OLED devices having the configuration ITO/PVK (40 nm)/[6% Ir(ppy)/3-2-(3-(6-(9H-carbazol-9-yl)-9H-3,9'-bicarbazol-9-yl)phenyl)-5-(3-methoxyphenyl)-1,3,4-oxadiazole (20 nm)/BCP (40 nm)/LiF/Al.

Figure 21A:
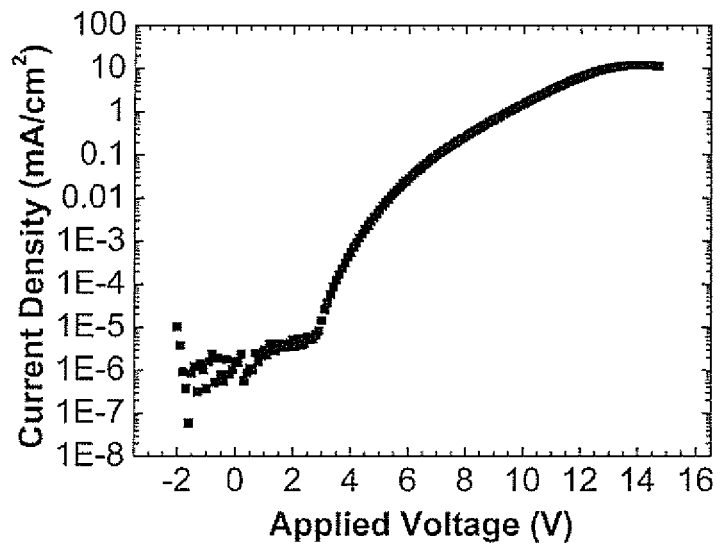
FIG. 21a shows the current density versus voltage characteristics of an OLED device comprising an emissive layer comprising 24346-(9H-carbazol-9-yl)-9H-3,9'-bicarbazol-9-yl)phenyl)-5-(3-methoxyphenyl)-1,3,4-oxadiazole, and 6% FIrpic as an emissive guest, and PVK as a hole-transmission layer, as described in Example 8.
Figure 21B:
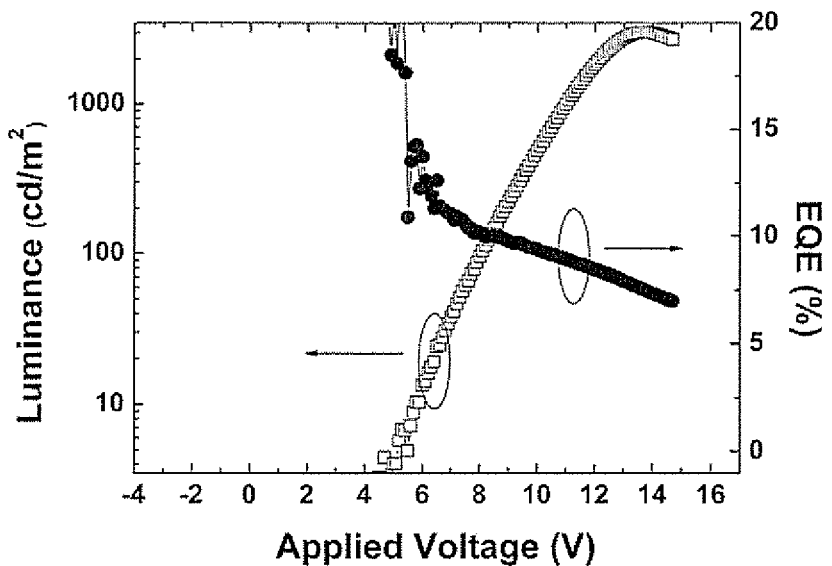
FIG. 21b shows the luminescence and external quantum efficiency versus voltage performance of the OLED device.

The current-voltage characteristic of the above referenced devices are shown in FIG. 21a The light output and external quantum efficiency as a function of voltage are shown in FIG. 21b. The device referenced above exhibits an external quantum efficiency of 10.5% and 9.5% at a light output level of 100 cd/m$^2$ and 1,000 cd/m$^2$, respectively.

CONCLUSIONS

The above specification, examples and data provide exemplary description of the manufacture and use of the various compositions and devices of the inventions, and methods for their manufacture and use. In view of those disclosures, one of ordinary skill in the art will be able to envision many additional embodiments or sub-embodiments of the inventions disclosed and claimed herein to be obvious, and that they can be made without departing from the spirit and scope of the inventions disclosed herein. The claims hereinafter appended define some of those embodiments.

What is claimed is:

1. A compound comprising an optionally substituted aryl or heteroaryl group bonded to a 1,3,4-oxadiazole group, the compound having the formula:

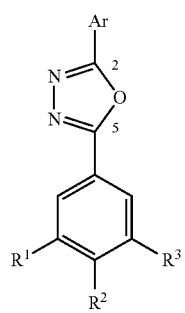

wherein a) Ar is a $C_5$-$C_{20}$ aryl or heteroaryl group optionally comprising one to five substituent groups independently selected from the group consisting of hydrogen, hydroxyl, fluorine, cyano, a $C_1$-$C_{20}$ alkyl, perfluoroalkyl, alkoxide, and perfluoroalkoxide groups; and b) at least two of the $R^1$, $R^2$ and $R^3$ groups is an optionally substituted carbazole group having the structure

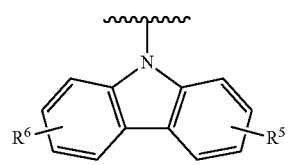

wherein $R^5$ and $R^6$ are independently selected from the group consisting of hydrogen, fluorine, cyano, and a $C_1$-$C_6$ organic group selected from alkyls, perfluoroalkyls, alkoxides, and perfluoroalkoxides, and the remaining $R^1$, $R^2$ or $R^3$ groups are independently selected from the group consisting of hydrogen, fluorine, cyano, or a $C_1$-$C_{20}$ alkyl, perfluoroalkyl, alkoxide, and perfluoroalkoxide groups; or one of the $R^1$, $R^2$, and $R^3$ groups is an optionally substituted carbazole group having the structure

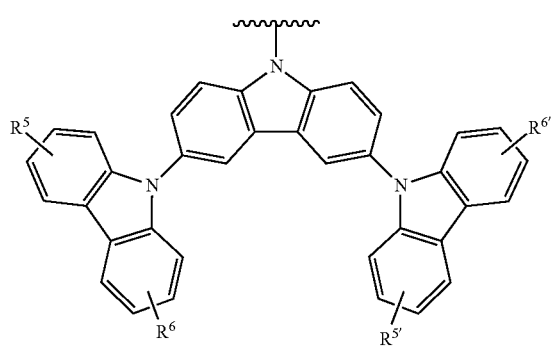

wherein $R^5$, $R^{5'}$, $R^6$ and $R^{6'}$ are independently selected from the group consisting of hydrogen, fluorine, cyano, and a $C_1$-$C_6$ organic group selected from the group consisting of alkyls, perfluoroalkyls, alkoxides, and perfluoroalkoxides, and the remaining $R^1$, $R^2$, or $R^3$ groups are independently selected from the group consisting of hydrogen, fluorine, cyano, and a $C_1$-$C_6$ organic group selected from the group consisting of alkyls, perfluoroalkyls, alkoxides, and perfluoroalkoxides.

2. The compounds of claim 1 having the structure

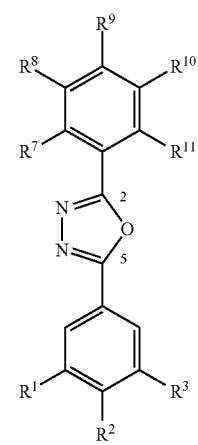

wherein $R^7$-$R^{11}$ are independently selected from the group consisting of hydrogen, fluorine, cyano, and a $C_1$-$C_{20}$ alkyl, perfluoroalkyl, alkoxide, and perfluoroalkoxide group.

3. The compounds of claim 1 wherein Ar comprises an optionally substituted phenyl, naphthyl, fluorenyl, anthracenyl, pyridyl, bipyridyl, thiophenyl, furanyl, or pyrolyl group.

4. The compounds of claim 1 wherein both the $R^1$ and $R^3$ groups have the structure

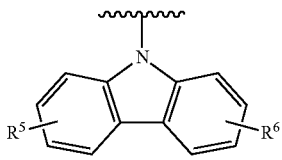

wherein $R^5$ and $R^6$ are independently selected from the group consisting of hydrogen, fluorine, cyano, and a $C_1$-$C_6$ organic group selected from the group consisting of alkyls, perfluoroalkyls, alkoxides, and perfluoroalkoxides, and $R^2$ is hydrogen.

5. The compounds of claim 1 wherein one of the $R^1$, $R^2$, and $R^3$ is an optionally substituted carbazole group having the structure

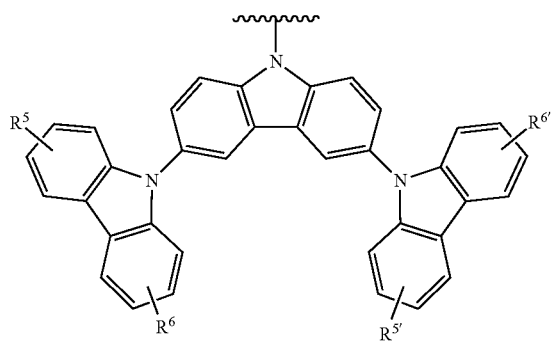

wherein $R^5$, $R^{5'}$, $R^6$ and $R^{6'}$ are independently selected from the group consisting of hydrogen, fluorine, cyano, and a $C_1$-$C_6$ organic group selected from the group consisting of alkyls, perfluoroalkyls, alkoxides, and perfluoroalkoxides, and the remaining $R^1$, $R^2$, or $R^3$ groups are hydrogen.

6. The compounds of claim 1 having the structure

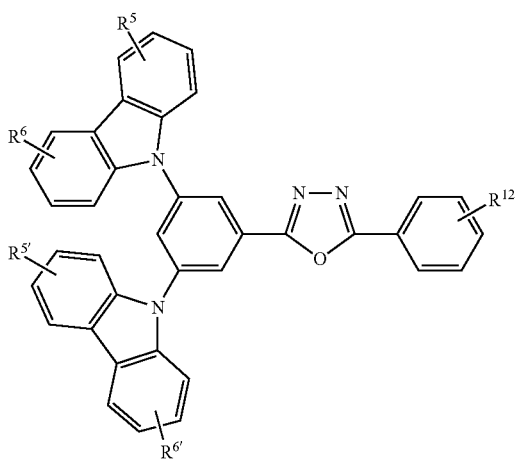

wherein $R^5$, $R^{5'}$, $R^6$, $R^{6'}$, and $R^{12}$ are independently selected from the group consisting of hydrogen, fluorine, cyano, and a $C_1$-$C_6$ organic group selected from the group consisting of alkyls, perfluoroalkyls, alkoxides, and perfluoroalkoxides.

7. The compounds of claim 1 having the structure

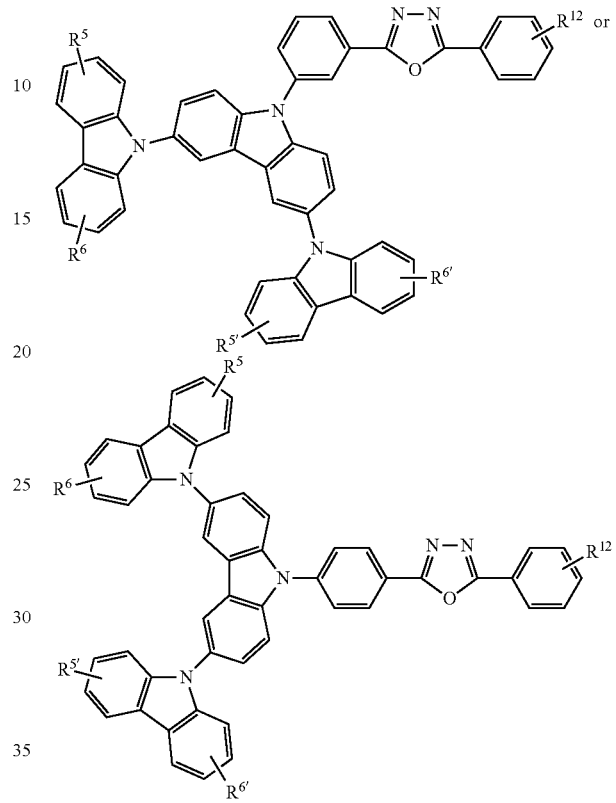

wherein $R^5$, $R^{5'}$, $R^6$, $R^{6'}$, and $R^{12}$ are independently selected from the group consisting of hydrogen, fluorine, cyano, and a $C_1$-$C_6$ organic group selected from the group consisting of alkyls, perfluoroalkyls, alkoxides, and perfluoroalkoxides.

8. The compounds of claim 1, wherein $R^5$, $R^{5'}$, $R^6$, and $R^{6'}$ are hydrogen or t-butyl.

9. The compounds of claim 1 having the structure

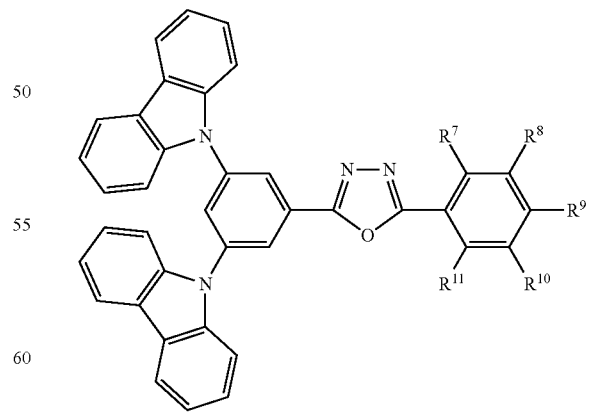

wherein $R^7$-$R^{11}$ are independently selected from the group consisting of hydrogen, fluorine, cyano, and a $C_1$-$C_6$ organic group selected from the group consisting of alkyls, perfluoroalkyls, alkoxides, and perfluoroalkoxides.

10. A composition comprising at least one compound of claim 1.

11. A device comprising at least one compound of claim 1.

12. The device of claim 11, wherein the device is a light emitting diode.

13. The device of claim 12 wherein the compound is used as a hole transporting material, an electron transporting material, or both.

14. The device of claim 12 comprising an emission layer comprising the compound of claim 1 as a host material to at least one phosphor.

15. The compound of claim 1 having the structure

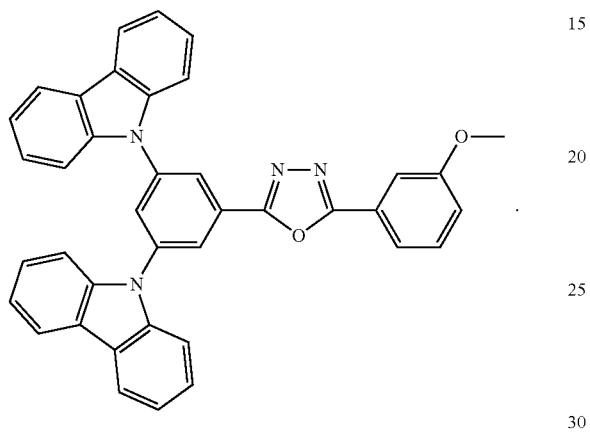

* * * * *